(12) United States Patent
Takayama et al.

(10) Patent No.: US 8,648,090 B2
(45) Date of Patent: Feb. 11, 2014

(54) INDOLE ALKALOID DERIVATIVES HAVING OPIOID RECEPTOR AGONISTIC EFFECT, AND THERAPEUTIC COMPOSITIONS AND METHODS RELATING TO SAME

(75) Inventors: Hiromitsu Takayama, Chiba (JP); Mariko Kitajima, Chiba (JP); Kenjiro Matsumoto, Togane (JP); Syunji Horie, Togane (JP)

(73) Assignees: National University Corporation Chiba University, Chiba (JP); Josai University Corporation, Tokyo (JP)

( * ) Notice: Subject to any disclaimer, the term of this patent is extended or adjusted under 35 U.S.C. 154(b) by 0 days.

(21) Appl. No.: 13/549,564

(22) Filed: Jul. 16, 2012

(65) Prior Publication Data

US 2012/0276195 A1    Nov. 1, 2012

Related U.S. Application Data

(63) Continuation of application No. 12/266,579, filed on Nov. 7, 2008, now Pat. No. 8,247,428.

(60) Provisional application No. 60/986,370, filed on Nov. 8, 2007.

(51) Int. Cl.
*A61K 31/439* (2006.01)
*C07D 491/22* (2006.01)

(52) U.S. Cl.
USPC .......................................... 514/280; 546/48

(58) Field of Classification Search
USPC ................................ 514/285, 280; 546/70, 48
See application file for complete search history.

(56) References Cited

U.S. PATENT DOCUMENTS 8,247,428 B2 *    8/2012    Takayama et al. ............ 514/285

FOREIGN PATENT DOCUMENTS

JP    9-291091    11/1997

OTHER PUBLICATIONS

Matsumoto, K. et al.: Antinociceptive effect of 7-hydroxymitragynine in mice: Discovery of an orally active opioid analgesic from the Thai medicinal herb *Mitragyna speciosa*. Life Sciences, vol. 74, pp. 2143-2155, 2004.*

Takayama, H. et al.: Discovery of anti-influenza A virus activity of a Corynanthe-type indole alkaloid, Hirsutine, in vitro and the structure-activity relationship of natural and synthetic analogs. Bioorg. & Medicin. Chem. Lett., vol. 7, pp. 3145-3148, 1997.*

Takayama et al., "Studies on the Synthesis and Opioid Agonistic Activities of Mitragynine-Related Indole Alkaloids: Discovery of Opoid Agonists Structurally Different from Other Opioid Ligands," Journal of Medicinal Chemistry, vol. 45, No. 9, 2002 pp. 1949-1956 (9 pages).

Takayama, H., et al., "New Procedure to Mask the 2,3-π Bond of the Indole Nucleus and Its Application to the Preparation of Potent Opioid Receptor Agonists with a Corynanthe Skeleton," Organic Letters, vol. 8, pp. 5705-5708, 2006.

* cited by examiner

*Primary Examiner* — Charanjit Aulakh
(74) *Attorney, Agent, or Firm* — Kilyk & Bowersox, P.L.L.C.

(57) ABSTRACT

Indole alkaloid derivatives having an opioid receptor agonistic effect, their synthesis, and therapeutic compositions containing these derivatives, and methods of treating conditions with these compounds and therapeutic compositions, are provided.

13 Claims, 10 Drawing Sheets

A) Compound 11

B) Compound 26

C) Compound 27

FIG. 4a
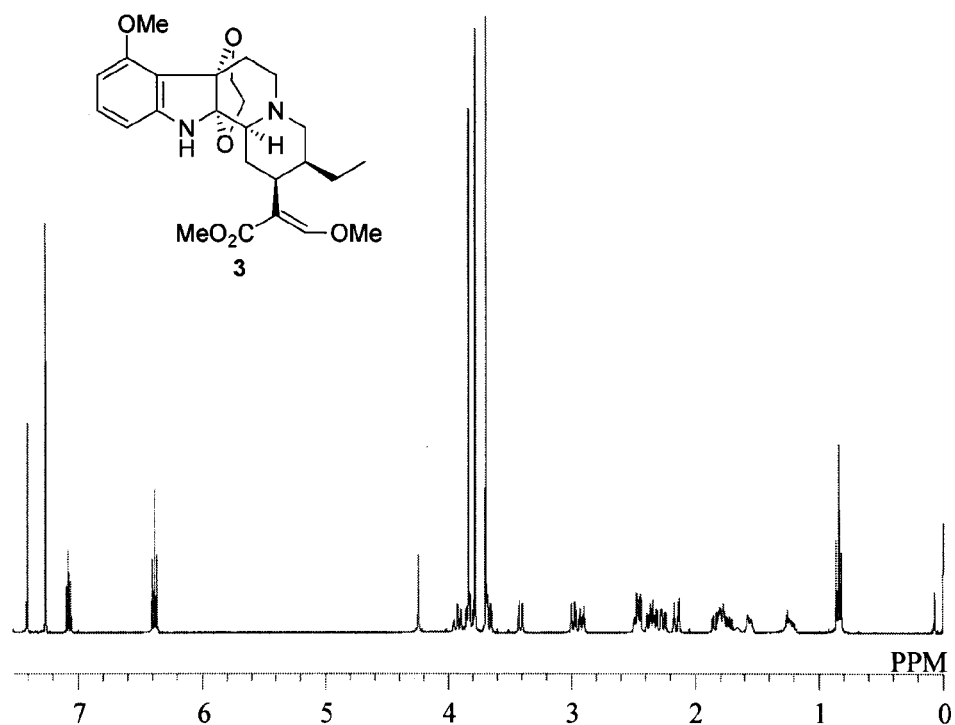
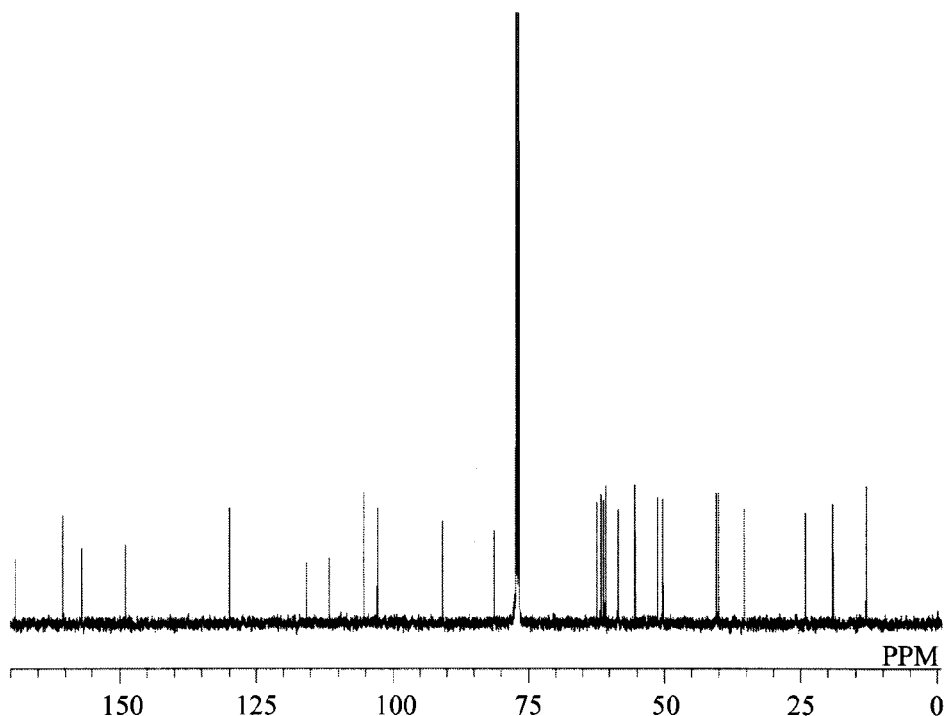
FIG. 4b

FIG. 6a
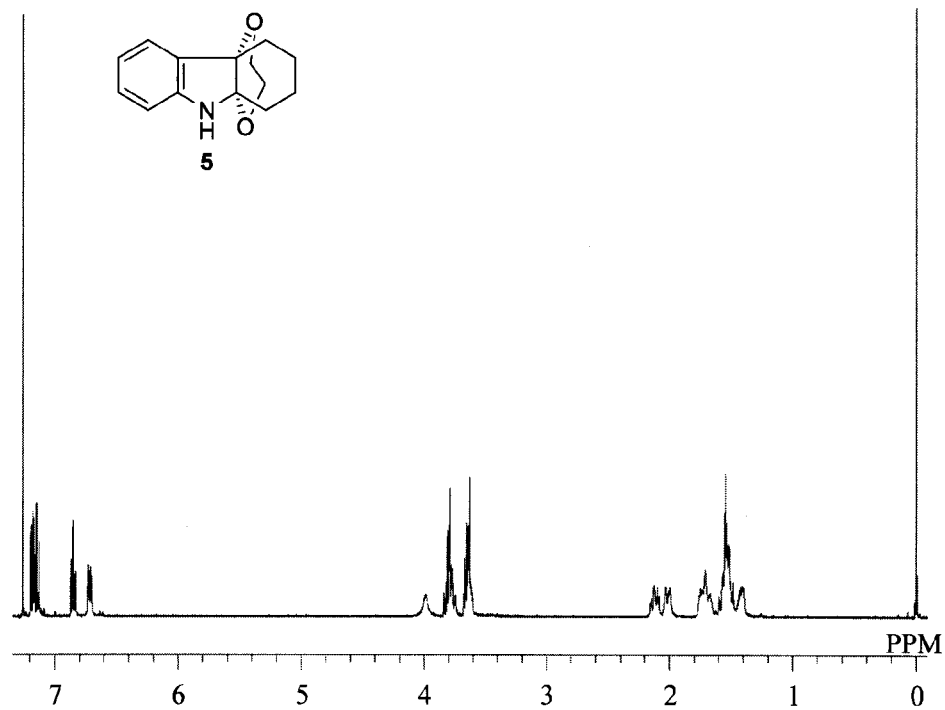
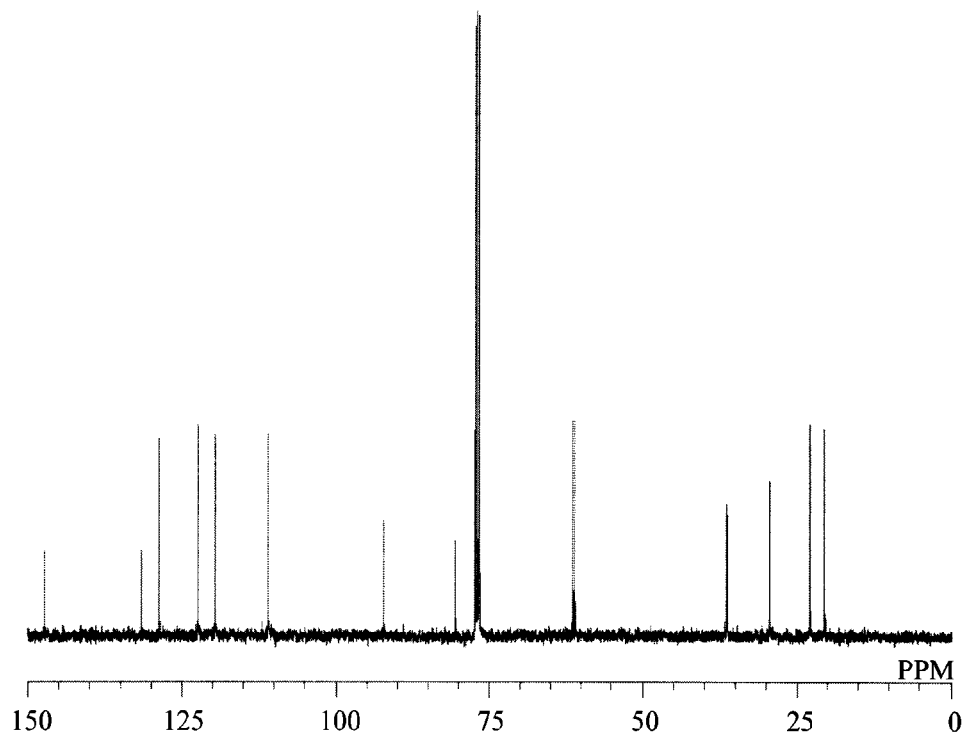
FIG. 6b

FIG. 7a
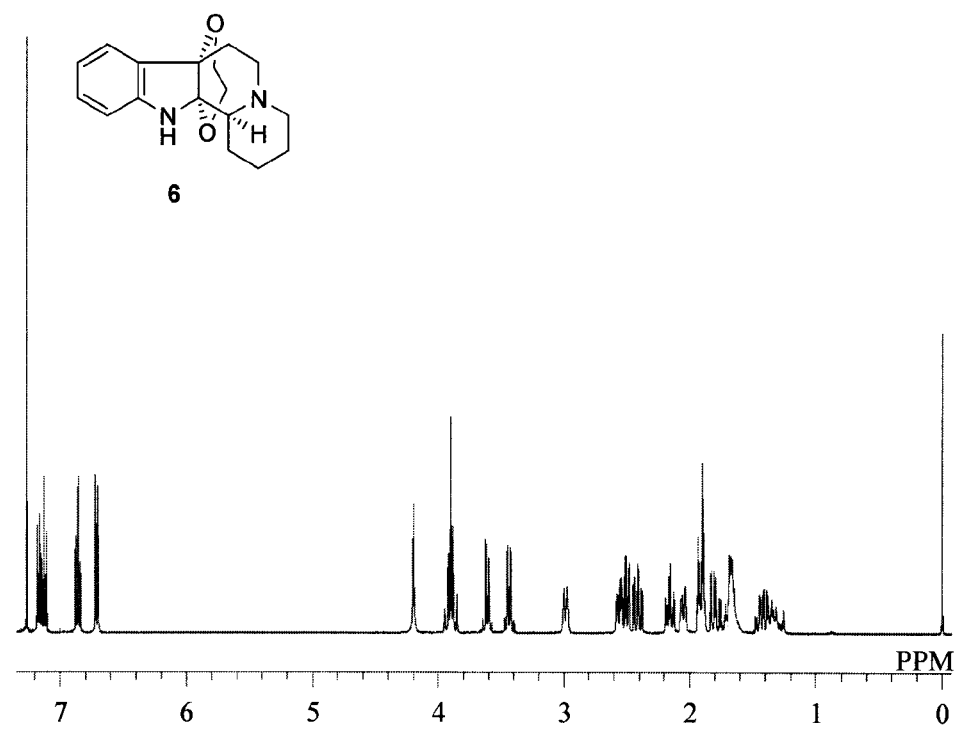
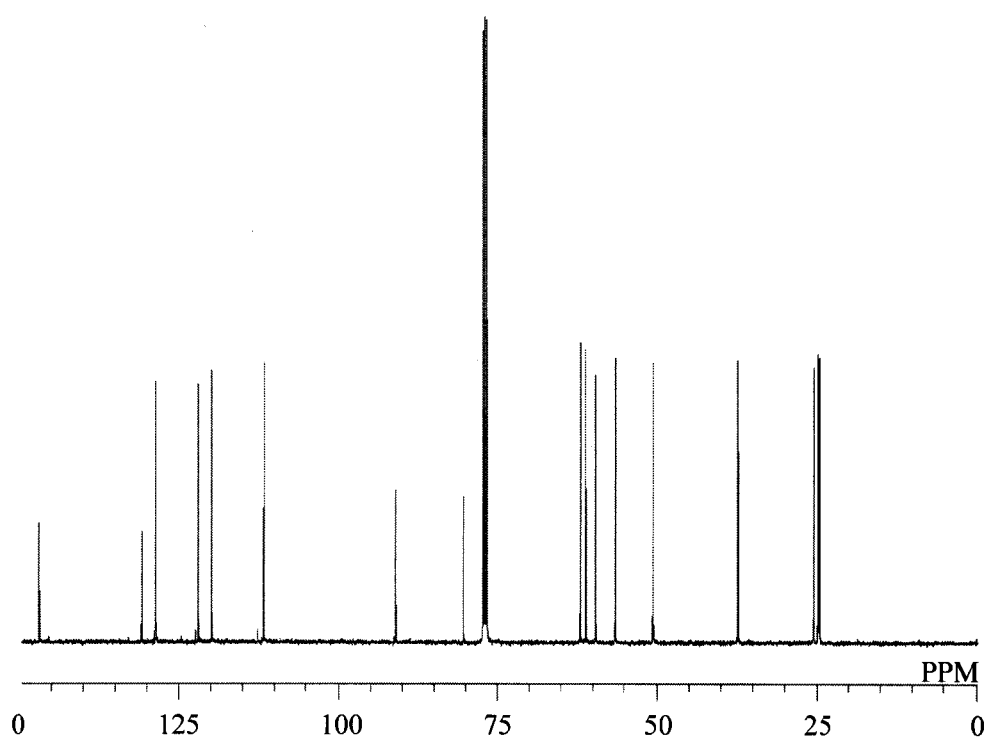
FIG. 7b

FIG. 8a
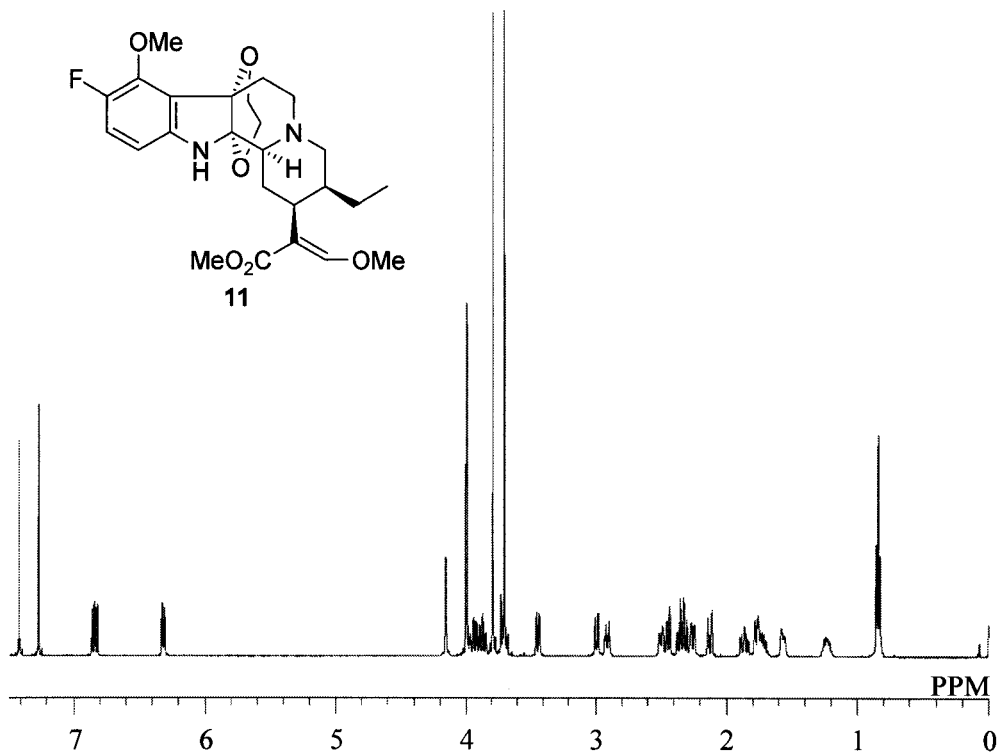
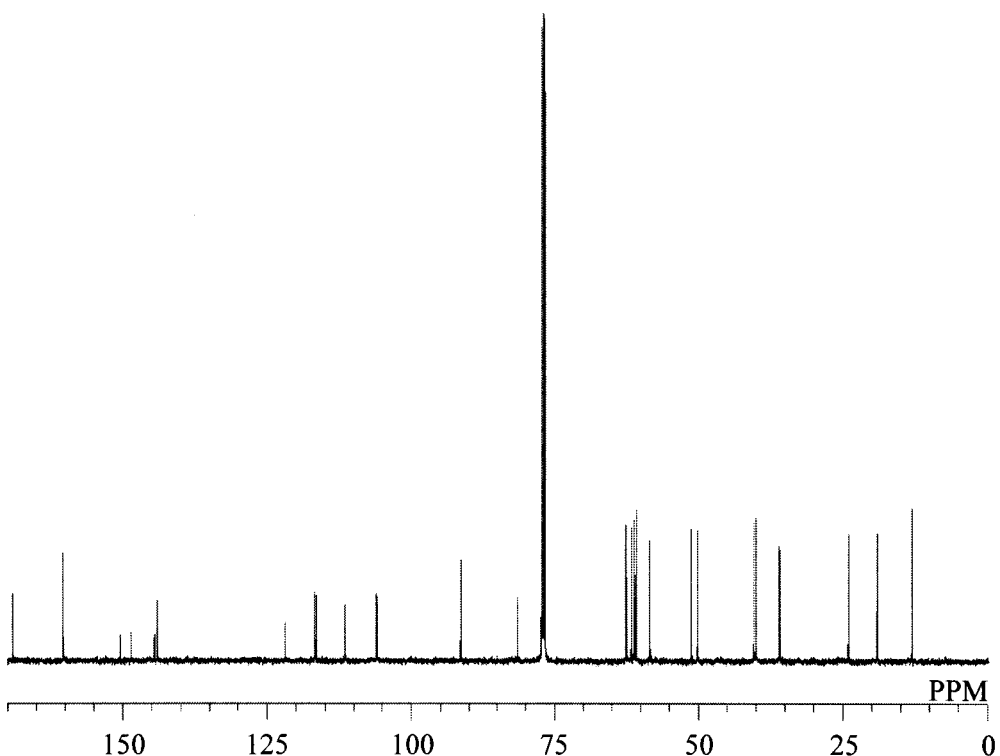
FIG. 8b

INDOLE ALKALOID DERIVATIVES HAVING OPIOID RECEPTOR AGONISTIC EFFECT, AND THERAPEUTIC COMPOSITIONS AND METHODS RELATING TO SAME

This application is a continuation of U.S. patent application Ser. No. 12/266,579, filed Nov. 7, 2008, which, in turn, claims the benefit under 35 U.S.C. §119(e) of prior U.S. Provisional Patent Application No. 60/986,370, filed Nov. 8, 2007, which is incorporated in its entirety by reference herein.

INTRODUCTION

The section headings used herein are solely for organization purposes and are not to be construed as limiting the subject matter described in any way.

The present invention pertains to indole alkaloid derivatives having an opioid receptor agonistic effect, their synthesis, and therapeutic compositions containing these derivatives, and additionally methods of treating conditions with these compounds and therapeutic compositions are also provided.

BACKGROUND

For the clinical treatment of acute and chronic severe pain, morphine is utilized as a standard analgesic. Morphine-related derivatives have been synthesized by simplification and introduction of substituents into the morphine structure in order to develop powerful analgesics without side effects (Corbett et al., 2006). Analgesics such as fentanyl and buprenorphine have been consequently derived from morphine. Most of them have μ-receptor agonist profiles and are used clinically. Despite their profound utility in the management of pain, they have undesirable side effects such as constipation, respiratory, depression, and development of dependence. It is known that μ-opioids such as morphine induce not only potent antinociception but also undesired rewarding effects following chronic administration in mice. The activation of dopaminergic systems after systemic administration of a μ-opioid agonist induces development of hyperlocomotion and place preference in mice (Matthes et al., 1999). Inhibitory effects on gastrointestinal transit (IGIT), such as constipation, tend to be a significant problem during administration of a chronic opioid such as morphine. The dose required for morphine's analgesic effect is much higher than that required for its constipating effect; thus, when morphine is used for analgesia, constipation is not a negligible issue (Megens et al., 1998).

The traditional Thai herbal medicine *Mitragyna speciosa* has long been used in Thailand for its opium- (Burkill, 1935) and coca-like effects and as a replacement for opium (Grewal, 1932; Suwanlert, 1975). The leaves of *Mitragyna speciosa* have been used, and are effective when taken orally. This medicinal herb contains many indole alkaloids (Takayama 2004). Mitragynine, illustrated below, a main constituent of this plant, is an indole alkaloid and structurally different from morphine, also illustrated below.

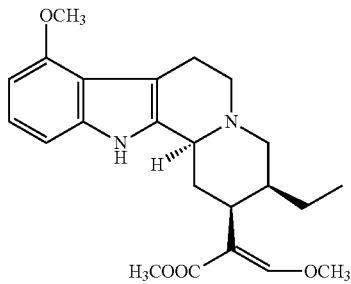
Mitragynine

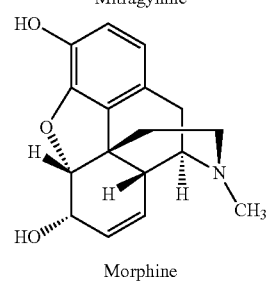
Morphine

Studies have been done on the pharmacological activities of mitragynine (Watanabe et al., 1997; Matsumoto et al., 2005) and related alkaloids (Yamamoto et al., 1999; Takayama et al., 2002; Takayama, 2004; Matsumoto et al., 2006a), which have found that these compounds have agonistic effects on opioid receptors. Recently, studies have been done on the opioid agonistic effects of the constituents of *Mitragyna speciosa* using in vitro assays. Among them, 7-hydroxymitragynine, illustrated below, which has a hydroxyl group at the C7 position of mitragynine, produced the most potent effect, suggesting that the opioid effect of *Mitragyna speciosa* is mostly based on the activity of 7-hydroxymitragynine (Horie et al., 2005).

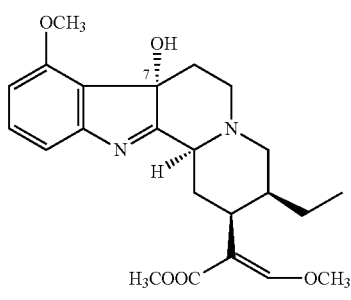
7-Hydroxymitragynine

7-Hydroxymitragynine induced a potent antinociceptive effect in mice, and its effect was more potent than those of morphine when subcutaneously or orally administered and mediated by the μ-opioid receptor mechanism (Matsumoto et al., 2004; Matsumoto et al., 2006). Furthermore, 7-hydroxymitragynine inhibited gastrointestinal transit less potently than morphine at each equi-antinociceptive dose (Matsumoto et al., 2006). The structural similarities between morphine and 7-hydroxymitragynine have been investigated using molecular modeling techniques (Matsumoto et al., 2005), but could not superimpose all three functional groups, i.e., a nitrogen atom, a benzene residue, and an oxygen atom on the benzene ring in the structures of morphine and 7-hydroxymitragynine. These functional groups have been considered to play an important role in producing analgesic activity (Dhawan et al., 1996).

A need has been recognized and solved by the present inventors for developing unique and potent analgesic compounds that can provide pain relief and/or prevention with reduced side effects.

SUMMARY

Uniquely structured indole alkaloid compounds are presented that are useful for pain treatment and other therapeutic effects with reduced adverse side effects compared to prior alkaloid analgesics such as morphine and morphine derivatives.

According to various embodiments, indole alkaloid derivatives are provided having an opioid receptor agonistic effect. The indole alkaloid compounds of the present teachings have a useful pharmacological profile for producing potent antinociceptive effects with fewer rewarding effects compared with μ-agonists in general, and weaker adverse side effects, such as in terms of IGIT, than morphine in particular.

According to various embodiments, indole alkaloid compound having an opioid receptor agonistic effect is provided having the formula (a):

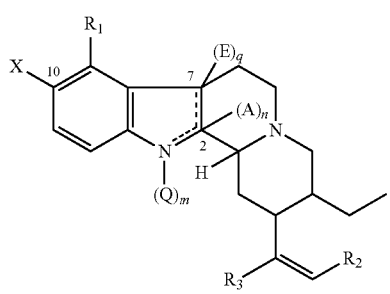

(a)

wherein X represents hydrogen nor a halogen atom, Q and A each independently represents hydrogen, alkyl, or aryl, E represents a hydrogen or a hydroxyl group, m is 0 or 1, n is 0 or 1, q is 0 or 1, $R_1$ and $R_2$ independently are hydrogen, hydroxy, alkoxy, aryloxy, alkyl, aryl, aralkyl, alkaryl, alkyl amide, amino, alkylamino, halogen, fluorinated alkyl, fluorinated alkoxy, nitro group, or cyano group, $R_3$ represents an ester group or carboxyl group, wherein the dashed lines each indicates an optional double bond with the provisos that when q is 0 and X is halogen then a 2,7 double bond is present and when m is 0, q is 1 and X is halogen then a 1,2 double bond is present. In another embodiment, when m, q and n each are 1, then no 1,2 or 2,7 position double bond is present in the indole moiety of the compound. In a further embodiment of formula (a), $R_1$ and $R_2$ independently are $C_1$-$C_6$ alkoxy, and $R_3$ represents a $C_1$-$C_6$ alkyl carboxylic acid ester group, and Q and A (if present) are hydrogen, and the other groups and mentioned bonds are the same as previously defined.

According to other various embodiments, a C10-halogenated indole alkaloid compound having an opioid receptor agonistic effect is provided that is selected from the formulae:

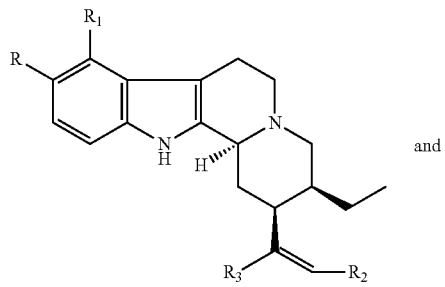

1

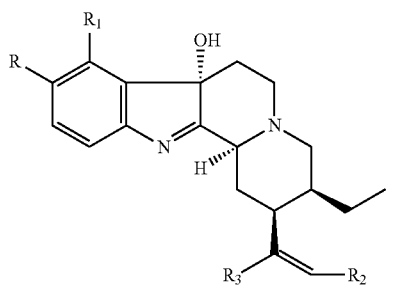

2 where R is a halogen atom, and $R_1$, $R_2$ and $R_3$ have the same respective meanings as defined above for formula (a).

According to other various embodiments, the C10-halogenated indole alkaloid compound having an opioid receptor agonistic effect is selected from the formulae:

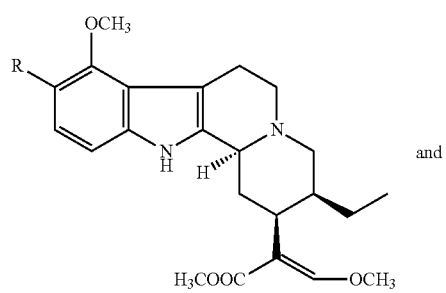

I

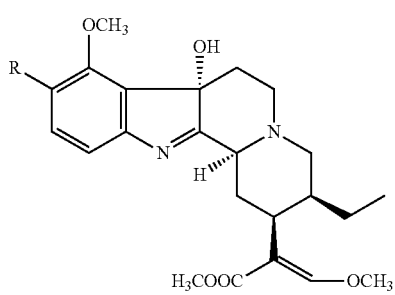

II wherein the R is fluorine, chlorine, bromine, or iodine.

According to other various embodiments, the C10-halogenated indole alkaloid compound is C10-halogenated mitragynine, 7-hydroxy-C10-halogenatedmitragynine, C10-halogenated 2,3-dimethylindole, C10-halogenated tetrahydrocarbazole, C10-halogenated indoloquinolizidine corynantheol, C10-halogenated dihydrocorynantheol, or C10-halogenated yohimbine, singly or in any combination thereof. According to further embodiments, the compound is 10-halomitragynine, 7-hydroxy-10-halomitragynine, singly or in a combination thereof.

According to other various embodiments, an indole alkaloid compound having an opioid receptor agonistic effect is provided having the formula:

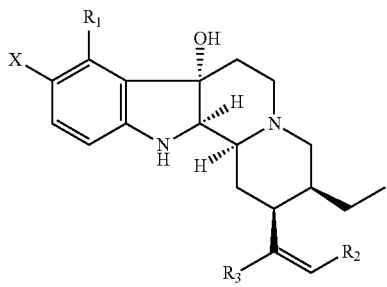

where X, $R_1$, $R_2$ and $R_3$ have the same respective meanings as defined above for formula (a).

According to other various embodiments, the indole alkaloid compound having an opioid receptor agonistic effect has the formula:

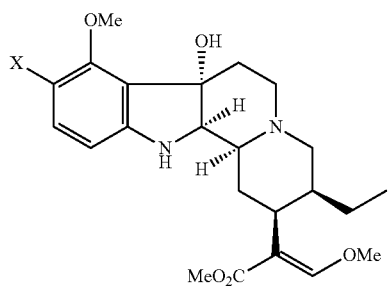

where X has the same meaning as defined above for formula (a).

According to other various other embodiments, a pharmaceutical composition is provided comprising a therapeutic amount of at least one indole alkaloid derivative compound having an opioid receptor agonistic effect or a pharmaceutically acceptable salt thereof of the present invention. The indole alkaloid derivative compound contained in these pharmaceutical compositions can be, for example, selected from amongst one of any of formulae (a), 1, 2, I, II, 1a, and Ia as set forth herein. These indole alkaloid derivative compounds may be used alone or in combinations thereof in a pharmaceutical composition. The pharmaceutical composition can further comprise a pharmaceutically acceptable carrier. The pharmaceutical composition can be provided in a pharmaceutically deliverable form, such as solutions, suspensions, emulsions, tablets, pills, pellets, granules, lozenges, capsules, capsules containing liquids, powders, sustained-release formulations, syrups, elixirs, creams, gels, suppositories, emulsions, aerosols, or sprays. In various embodiments, the indole alkaloid derivative (as an active ingredient) can be compounded in salt form into tablets or pills and the like, or alternatively can be dissolved in solution. The pharmaceutical composition can contain, for example, 0.1 wt % to 100 wt %, particularly about 1 wt % to about 90 wt %, more particularly from about 5 wt % to about 80 wt %, of the indole alkaloid derivative compound or a pharmaceutically acceptable salt thereof. Other wt % can be from 10 wt % to 75 wt %; from 15 wt % to 60 wt %, from 20 wt % to 50 wt % of the active ingredient.

According to other various embodiments, a method is provided for eliciting a therapeutic effect in a patient (e.g., human, animal) in need thereof, comprising the step of administering to the patient an effective dose of an indole alkaloid derivative compound having an opioid receptor agonistic effect or a pharmaceutically acceptable salt thereof of the present invention. The indole alkaloid derivative compound can be selected, for example, from amongst any one of formula (a), 1, 2, I, II, 1a or Ia as set forth herein, wherein X or R, as applicable, is fluorine, chlorine, bromine, or iodine.

According to various embodiments, the therapeutic effect achieved by the method comprises an analgesic effect, although not limited thereto. In various embodiments, the indole alkaloid compounds of the present teachings can be used to treat or prevent acute or chronic pain. The step of administering can be performed, for example, by a delivery route selected from oral, transdermal, intramuscular, intravenous, inhalation, injection, infusion, or suppository. The patient can be, for example, an animal, such as a mammal, although not limited thereto. According to particular embodiments, the patient is a human. Where the patient is a human and the therapeutic effect is pain treatment, the effective total daily dosage of the indole alkaloid derivative compound can range, for example, from about 0.1 mg to about 1,000 mg active compound/kg body weight of the patient. Other dosages are possible.

According to various embodiments, a method is provided for synthesizing a 10-halo-substituted indole alkaloid derivative compound, such as those exemplified in formulae 1, 2, I and II, wherein a Corynanthe-type indole alkaloid is reacted with hypervalent iodine in the presence of ethylene glycol effective to provide a 2,3-ethylene glycol bridged indoline adduct, effective to mask a 2,3-π bond of an indole nucleus of the adduct. A halogen atom is introduced at a C10 position of the adduct via electrophilic aromatic substitution, providing a C10-halogenated adduct derivative. The C10-halogenated adduct derivative is converted into a corresponding C10-halogenated mitragynine derivative by reduction reaction effective to eliminate the ethylene glycol bridge. Optionally, the C10-halogenated mitragynine derivative is further converted into a corresponding 7-hydroxy-10-halomitragynine derivative by oxidation reaction.

According to other various embodiments, a method is provided for synthesizing an indole alkaloid derivative compound, such as those exemplified in formulae 1a and Ia, wherein 7-hydroxymitragynine or 7-hydroxy-10-halomitragynine is reacted with a reducing agent, such as $NaBH_4$, in a solvent such as MeOH, to yield compounds of formulae 1a and Ia.

The reaction product obtained by the methods according to various embodiments of the present invention can contain the indole alkaloid derivative compound in a concentration, for example, of from about 5 wt % to 100 wt %, particularly from about 10 wt % to about 99 wt %, about 20 wt % to about 99 wt %, and 50 wt % to about 99 wt %.

BRIEF DESCRIPTION OF THE DRAWINGS

FIG. 4a is the 1H-NMR for Ethylene Glycol-Bridged Compound 3 and FIG. 4b is the 13C-NMR for Ethylene Glycol-Bridge Compound 3.

FIG. 6a is the 1H-NMR for Compound 5 and FIG. 6b is the 13C-NMR for Compound 5.

FIG. 7a is the 1H-NMR for Compound 6 and FIG. 7b is the 13C-NMR for Compound 6.

FIG. 8a is the 1H-NMR for Compound 11 and FIG. 8b is the 13C-NMR for Compound 11.

DESCRIPTION OF VARIOUS EMBODIMENTS

Figure 1:
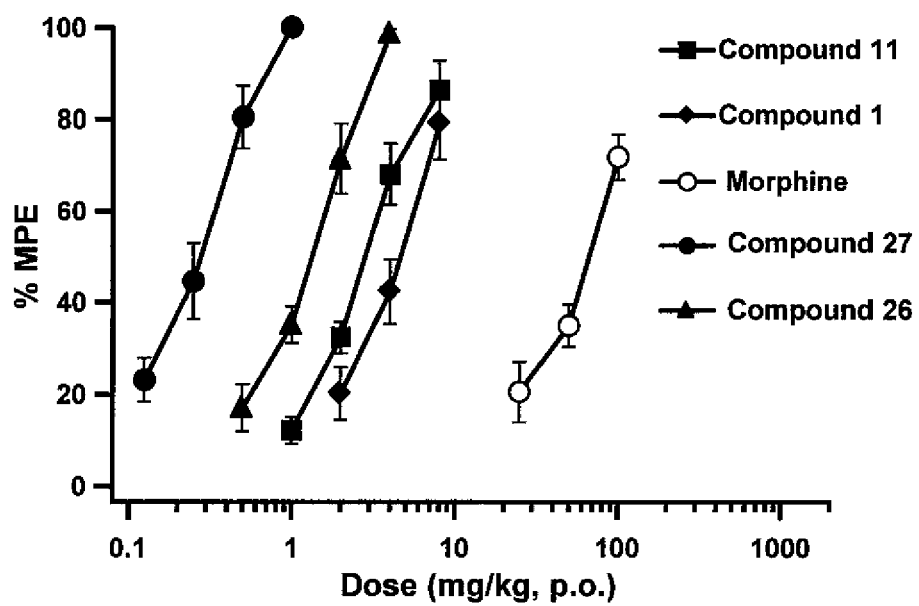
FIG. 1 shows dose-response curves for analgesic effect of orally-administered compound 1, compound 11, compound 26, compound 27 and morphine in tail-flick test in mice, as discussed in Example 2 herein. Analgesia was quantified using the percentage of maximum possible effect (% MPE) and calculated as: % MP=[(test latency−pre-drug latency)/(cut-off time−pre-drug latency)]×100. A cut-off time of 10 s was used to prevent tissue damage. Each value represents mean±S.E.M. of data obtained from 7 to 9 mice.

It is to be understood that the following descriptions are exemplary and explanatory only. The accompanying drawings are incorporated in and constitute a part of this application and illustrate several exemplary embodiments with the description. Reference will now be made to various embodiments, examples of which are illustrated in the accompanying drawings.

For purposes of this application, the following definitions apply.

"Halogen" or "-Halo" means fluorine, chlorine, bromine, or iodine.

The phrase "pharmaceutically acceptable salt," as used herein, can be a salt formed, for example, from an acid and a basic functional group, such as a nitrogen group, of the indole alkaloid compound. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, pamoate salts, or hydrochloride salts thereof.

The phrases "therapeutic amount," "therapeutic dose," "effective amount," "effective dose," and the like, when used in connection with an indole alkaloid compound means an amount effective for treating and/or preventing a condition.

The phrases "treatment of," "treating," and the like include the amelioration or cessation of a condition, or a symptom thereof.

The phrases "prevention of," "preventing," and the like include the avoidance of the onset of a condition, or a symptom thereof.

The term "animal," for purposes of treatment, refers to a mammal, bird, reptile or fish. Representative animals include, for example, a monkey, chimpanzee, baboon, cow, buffalo, horse, sheep, pig, chicken, turkey, duck, cat, dog, rabbit, mouse, rat, hamster, guinea pig, and human.

The term "mammal" for purposes of treatment refers to any animal classified as a mammal, including humans, domestic and farm animals, and zoo, sport, or pet animals.

Indole Alkaloid Derivative Structures

Uniquely structured indole alkaloid compounds are provided in accordance with the present teachings that can be used for pain treatment and other therapeutic effects with reduced adverse side effects compared to prior alkaloid analgesics such as morphine and morphine derivatives.

According to various embodiments, indole alkaloid compound having an opioid receptor agonist effect is provided having the formula (a) indicated below:

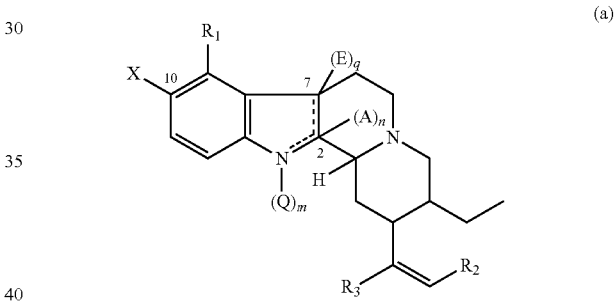

wherein:
X represents halogen atom or hydrogen,
Q and A each independently represents hydrogen, alkyl, or aryl,
E represents a hydrogen or hydroxyl group,
m is 0 or 1,
n is 0 or 1,
q is 0 or 1,
$R_1$ and $R_2$ independently are hydrogen, hydroxy, alkoxy, aryloxy, alkyl, aryl, aralkyl, alkaryl, alkyl amide, amino, alkylamino, halogen, fluorinated alkyl, fluorinated alkoxy, nitro group, or cyano group,
$R_3$ represents an ester group or carboxyl group,
the dashed lines each indicates an optional double bond with provisos that when q is 0 and X is halogen then a 2,7 double bond is present, and when m is 0, q is 1 and X is halogen then a 1,2 double bond is present. In another embodiment, when m, q and n each is 1, then no 1,2 or 2,7 position double bond is present in the indole moiety of the compound.

In a further embodiment of the compounds of formula (a), $R_1$ and $R_2$ independently are $C_1$-$C_6$ alkoxy, $R_3$ represents a $C_1$-$C_6$ alkyl carboxylic acid ester group, and Q and A (if present) are hydrogen, and the other groups and mentioned bonds are the same as previously defined. The $C_1$-$C_6$ alkoxy groups can be, e.g., methoxy, ethoxy, propoxy, butoxy, and the like), and $C_1$-$C_6$ alkyl carboxylic acid ester group can be, e.g., acetate, ethanoate, butanoate, hexanoate, and the like. $R_1$ and $R_2$ can be the same or different. $R_1$, $R_2$, and $R_3$ can be substituted or unsubstituted. Any $C_3$ or greater alkyl portions of these groups can be linear or branched.

According to other various embodiments, a C10-halogenated indole alkaloid compound having opioid receptor agonistic effect is provided that is selected from the formulae:

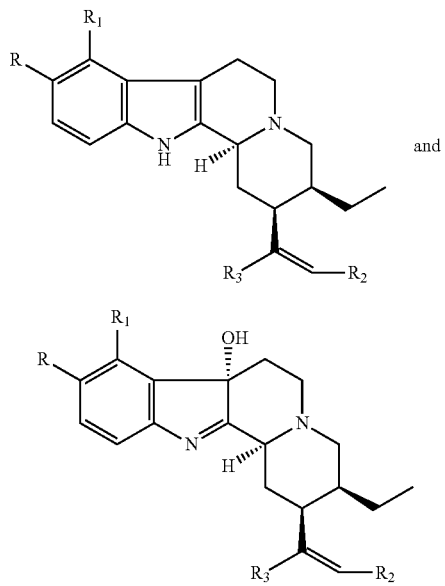

where R has the same meaning as X as defined above, $R_1$, $R_2$ and $R_3$ have the same respective meanings as defined above.

According to other various embodiments, the C10-halogenated indole alkaloid compound having opioid receptor agonistic effect is selected from the formulae:

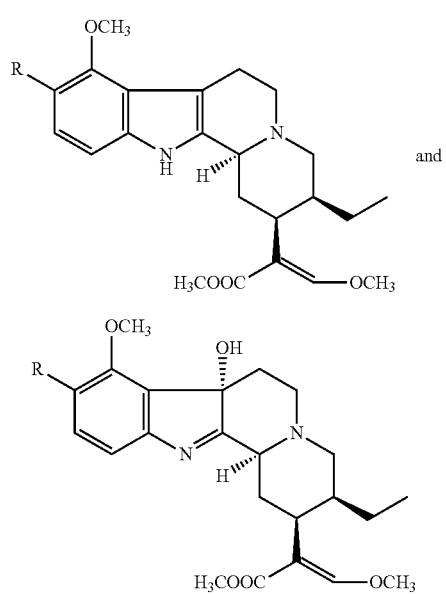

wherein the R is fluorine, chlorine, bromine, or iodine.

According to other various embodiments, the C10-halogenated indole alkaloid compound is C10-halogenated mitragynine, 7-hydroxy-C10-halogenatedmitragynine, C10-halogenated 2,3-dimethylindole, C10-halogenated tetrahydrocarbazole, C10-halogenated indoloquinolizidine corynantheol, C10-halogenated dihydrocorynantheol, or C10-halogenated yohimbine, singly or in any combination thereof.

According to further embodiments, the compound is 10-halomitragynine, 7-hydroxy-10-halomitragynine, singly or in a combination thereof. Specific therapeutic compounds according to embodiments of the present teachings include, for example, 7-hydroxy-10-fluoromitragynine, 7-hydroxy-10-chloromitragynine, 7-hydroxy-10-bromomitragynine, 10-fluoromitragynine, 10-chloromitragynine, or 10-bromomitragynine.

According to other various embodiments, an indole alkaloid compound having an opioid receptor agonistic effect is provided having the formula:

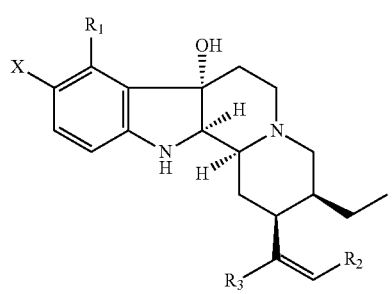

where X, $R_1$, $R_2$ and $R_3$ have the same respective meanings as defined above for formula (a).

According to other various embodiments, the indole alkaloid compound having an opioid receptor agonistic effect has the formula:

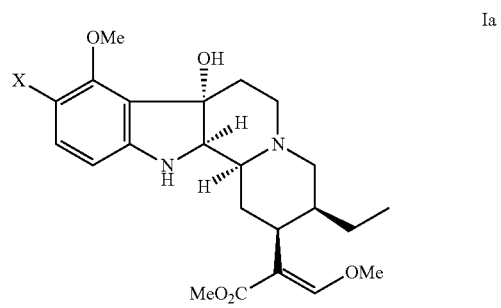

where X has the same meaning as defined above for formula (a).

According to various embodiments, the indole alkaloid compounds of the present teachings have a useful pharmacological profile for producing potent antinociceptive effects with fewer rewarding effects compared with μ-agonists in general and weaker adverse side effects than morphine in particular. According to various embodiments, indole alkaloid compounds of the present teachings can inhibit gastrointestinal transit less potently than morphine at each equi-antinociceptive dose. Compounds of formula 1a (and Ia) have shown oral analgesic activity that is greater than about 200 times or more potent than that of morphine. They also exhibit potent in vitro activity relative to other mitragynine derivatives.

Although not desiring to be bound to theory, it is thought that the indole alkaloid compounds of the present teachings are unique dual acting μ- and κ-opioid agonists, which can produce stronger antinociceptive effects and weaker adverse effects than morphine. As discussed previously, μ-opioids induce potent antinociception, but they also induce psychological dependence during chronic administration. Activation of dopaminergic systems after administration of the μ-opioid agonist induces the development of rewarding effects. In contrast, κ-opioid receptors negatively modulate the activity of dopaminergic neurons and inhibit the rewarding effects mediated by μ-opioid receptors (Narita et al., 2001). Therefore, it is hypothesized that a dual acting μ- and κ-opioid agonist will induce potent antinociceptive effects and fewer rewarding effects than μ agonists such as morphine. The involvement of μ- and κ-opioid receptor mechanisms in the opioid agonistic effects of indole alkaloid compounds of the present teachings is possible. The affinities of indole alkaloid compounds of embodiments of the present teachings for the three opioid receptor types of μ-, δ-, and κ-opioid receptors can be determined by evaluating the inhibition of binding of ligands to μ-, δ-, and κ-opioid receptors.

Synthesis Methods

Synthesis of C10-halogenated indole alkaloid compounds of formula 1.

Synthesis methods that can be utilized or adapted in preparing C10-halogenated indole alkaloid compounds of embodiments of the present teachings are described, for example, in Takayama, H., et al. (2006) and Takayama, H., et al. (2002).

In one embodiment of the present invention, the inventors have found a new method to protect the 2,3-π of indole alkaloids, which has been applied to the preparation of derivatives having various substituents at the C10-position in Corynanthe-type indole alkaloids such as hydroxymitragynine or its parent compound.

The present inventors have determined that attempts at the direct introduction of electrophilic substituents on the benzene ring in 7-hydroxymitragynine or its parent compound are not successful. The present investigators have devised a method to protect the 2,3-π of indole alkaloids, producing the aniline structure that acts as a reactive aromatic compound toward various electrophiles. According to one embodiment, the general synthesis scheme is shown in Scheme A.

ity of the indole nucleus at the β-position, is used for the modification of the benzene ring of the indoline derivative and is supplied to the preparation of potent opioid receptor agonists with the Corynanthe skeleton. The purity of the reaction product compounds can be checked, for example, by high-performance liquid chromatography and $^1$H-nuclear magnetic resonance (500 MHz) analysis.

Synthesis of Indole Alkaloid Compounds of Formula 1a.

A method also is provided for synthesizing an indole alkaloid derivative compound, such as those exemplified in formulae 1a and Ia, wherein 7-hydroxymitragynine or 7-hydroxy-10-halomitragynine, or a similar indole alkaloid, is reacted with an indole reducing agent, such as $NaBH_4$, in a solvent such as MeOH, to yield compounds of formulae 1a and Ia. According to one embodiment thereof, the general synthesis scheme is shown in Scheme B.

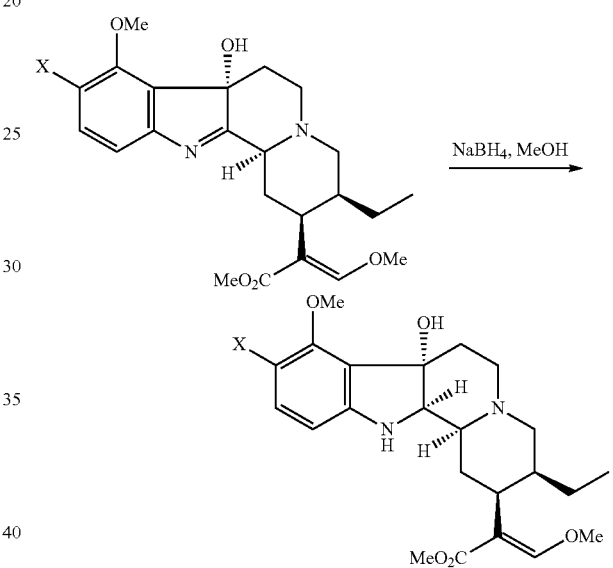

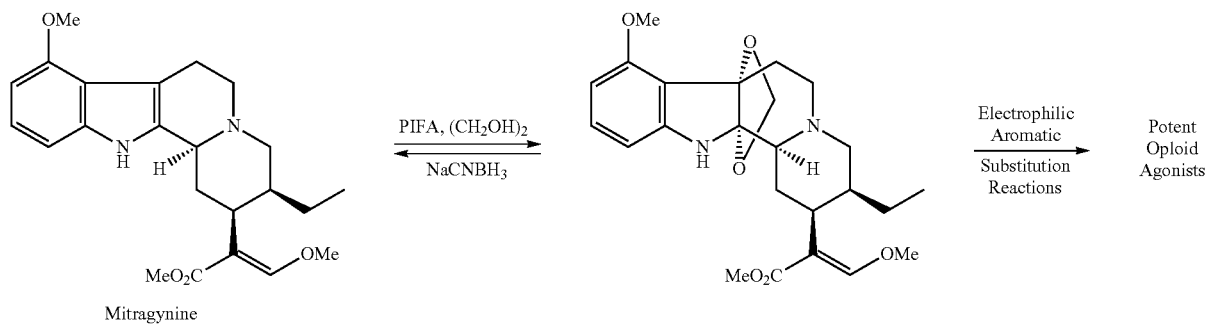

where X is a halogen atom or a hydrogen atom depending on the starting compound.

The reaction product obtained by methods according to embodiments of the present teachings, such as illustrated above, can contain the indole alkaloid derivative compound in a concentration, for example, of from about 5 wt % to 100 wt %, particularly from about 10 wt % to about 99 wt %, from about 20 wt % to about 99 wt %, or from 50 wt % to about 99 wt %.

Therapeutic/Prophylactic Administration and Compositions

Pharmaceutical compositions according to embodiments of the present teachings can contain, for example, from 0.1 wt % to 100 wt %, particularly from about 1 wt % to about 90 wt %, more particularly from about 5 wt % to about 80 wt %, of the indole alkaloid derivative compound or a pharmaceutically acceptable salt thereof, which amounts can vary depending on factors such as the overall formulation and form thereof, intended treatment, and patient details at hand, and the like.

Due to their activity, the indole alkaloid compounds of embodiments according to the present teachings are advantageously useful, for example, in veterinary and human medicine. As described above, the indole alkaloid compounds are useful for treating or preventing a condition in an animal in need thereof. When administered to an animal, the indole alkaloid compounds are administered as a component of a composition that comprises any pharmaceutically acceptable carrier or excipient. The present compositions, which comprise at least one indole alkaloid compound, can be administered orally. The indole alkaloid compounds of the invention can also be administered by any other convenient route, for example, by infusion or bolus injection, by absorption through epithelial or mucocutaneous linings (e.g., oral, rectal, and intestinal mucosa, etc.) and can be administered together with another biologically active agent. Administration can be systemic or local. Various delivery systems are known, e.g., encapsulation in liposomes, microparticles, microcapsules, capsules, etc., and can be used to administer the indole alkaloid compounds.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. The mode of administration is left to the discretion of the practitioner. In most instances, administration will result in the release of the C10-halogenated indole alkaloid compounds into the bloodstream.

In specific embodiments, it can be desirable to administer the indole alkaloid compounds locally. This can be achieved, for example, and not by way of limitation, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, it can be desirable to introduce the indole alkaloid compounds into the central nervous system or gastrointestinal tract by any suitable route, including intraventricular, intrathecal, and epidural injection, and enema. Intraventricular injection can be facilitated by an intraventricular catheter, for example, attached to a reservoir, such as an Ommaya reservoir. In certain embodiments, it can be desireable to administer the indole alkaloid compounds by subcutaneous administration, such as, for example, as dissolved in phosphate-buffered saline (pH 5.3-5.5).

Pulmonary administration can also be employed, e.g., by use of an inhaler or nebulizer, and formulation with an aerosolizing agent, or via perfusion in a fluorocarbon or synthetic pulmonary surfactant. In certain embodiments, the indole alkaloid compounds can be formulated as a suppository, with traditional binders and excipients such as triglycerides.

In another embodiment, the indole alkaloid compounds can be delivered in a vesicle, in particular a liposome. In yet another embodiment, the indole alkaloid compounds can be delivered in a controlled-release system or sustained-release system. In one embodiment, a pump can be used. In another embodiment, polymeric materials can be used. In yet another embodiment, a controlled- or sustained-release system can be placed in proximity of a target of the indole alkaloid compounds, e.g., the spinal column, brain, or gastrointestinal tract, thus requiring only a fraction of the systemic dose.

The present compositions can optionally comprise a suitable amount of a pharmaceutically acceptable excipient so as to provide the form for proper administration to the animal. Such a pharmaceutical excipient can be a liquid, such as water or an oil, including those of petroleum, animal, vegetable, or synthetic origin, such as peanut oil, soybean oil, mineral oil, sesame oil and the like. The pharmaceutical excipient can be saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipient is sterile when administered to an animal. Water is a particularly useful excipient when the indole alkaloid compound is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsions, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule. Other examples of suitable pharmaceutical excipients are described in Remington's Pharmaceutical Sciences, incorporated herein by reference. In one embodiment, the indole alkaloid compounds are formulated in accordance with routine procedures as a composition adapted for oral administration to human beings. Compositions for oral delivery can be in the form of tablets, lozenges, aqueous or oily suspensions, granules, powders, emulsions, capsules, syrups, or elixirs, for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked or bolus profiles of immediate release formulations. A time-delay material such as glycerol (mono)stearate can also be used. Oral compositions can include standard excipients such as mannitol, lactose, starch, magnesium stearate, sodium saccharin, cellulose, or magnesium carbonate. In one embodiment, the excipients are of pharmaceutical grade.

In another embodiment, the indole alkaloid compounds can be formulated for intravenous administration. Typically, compositions for intravenous administration can comprise a sterile isotonic aqueous buffer. Where necessary, the compositions can also include a solubilizing agent. Generally, the ingredients are supplied either separately or mixed together in unit dosage form, for example, as a dry lyophilized powder or water free concentrate in a hermetically sealed container such as an ampule or sachette indicating the quantity of active agent. Where the indole alkaloid compounds are to be administered by infusion, they can be dispensed, for example, with an infusion bottle containing sterile pharmaceutical grade water or saline. Where the indole alkaloid compounds are administered by injection, an ampule of sterile water for injection or saline can be provided so that the ingredients can be mixed prior to administration.

The amount of the indole alkaloid compounds that is effective for the treatment or prevention of a condition can be determined by standard clinical techniques. In addition, in vitro or in vivo assays can optionally be employed to help identify optimal dosage ranges. When administered for the treatment and/or prevention of a particular disorder and/or disease state, it is understood that the effective dosage may vary depending upon the particular compound used, the mode of administration, the condition, and severity thereof, of the condition being treated, as well as the various physical factors related to the patient being treated, such that the precise dosing regimen to be employed can also depend on these factors and the judgment of a health care practitioner treating the patient. Suitable effective dosage amounts, for example, can range from about 0.1 mg/kg body weight/day to about 1,000 mg/kg body weight/day, particularly from about 1 mg/kg body weight/day to about 200 mg/kg body weight/day, and more particularly from about 2 mg/kg body weight/day to about 100 mg/kg body weight/day. The dosage amount can be administered in a single dosage treatment per day or as divided into separate smaller dosage treatments per day, depending on the treatment circumstances. For example, in pain treatment, from about 5 to about 30 mg can be administered to a patient in need thereof every four hours or other dosage and/or interval, as needed. The indole alkaloid compounds also can be administered as an aqueous solution or other solution containing the compound or salt thereof, and such as in a concentration of from about 1 mg to about 25 mg per mL or other concentration.

The opioid component of the present methods and compositions may further include one or more other active ingredients that may be conventionally employed in analgesic and/or cough-cold-antitussive combination products. Such conventional ingredients include, for example, aspirin, acetaminophen, phenylpropanolamine, phenylephrine, chlorpheniramine, caffeine, and/or guaifenesin, and the like. Typical or conventional ingredients that may be included in the opioid component are described, for example, in the Physicians' Desk Reference, the disclosure of which is hereby incorporated herein by reference, in its entirety.

In addition, the opioid component may further include one or more compounds that may be designed to enhance the analgesic potency of the opioid and/or to reduce analgesic tolerance development. Although the compounds of the present invention may be administered as the pure chemicals, the active ingredient can be administered as a pharmaceutical composition. The invention thus further provides a pharmaceutical composition comprising an effective amount of one or more of the compounds of the invention, preferably one or more compounds described herein, together with one or more pharmaceutically acceptable carriers therefore and, optionally, other therapeutic and/or prophylactic ingredients. The carrier(s) must be acceptable in the sense of being compatible with the other ingredients of the composition and not deleterious to the recipient thereof. The compounds of the invention may be administered in an effective amount by any of the conventional techniques well-established in the medical field. The compounds employed in the methods of the present invention including, for example, opioids and the compounds of the invention, or a pharmaceutically acceptable salt thereof, may be administered by any means that results in the contact of the active agent(s) with the relevant site or site(s) of action in the body of a patient. The compounds may be administered by any conventional means available for use in conjunction with pharmaceuticals, either as individual therapeutic agents or in a combination of therapeutic agents. For example, they may be administered as the sole active agents in a pharmaceutical composition, or they can be used in combination with other therapeutically active ingredients.

The present invention will be further clarified by the following examples, which are intended to be purely exemplary of the present invention. Unless otherwise indicated, all numbers expressing quantities, percentages or proportions, and other numerical values used in the specification and claims, are to be understood as being weight percentages unless indicated to the contrary.

EXAMPLES

Example 1

C10-Substituted Indole Alkaloid Compounds

Synthesis of C10-Substituted Indole Alkaloid Compounds

Mitragynine (compound 2) was treated with 1 equivalent of phenyliodine bis (trifluoroacetate) (PIFA) in the presence of ethylene glycol (EG) in MeCN at 0° C., and a 2,3-ethylene glycol bridged indoline derivative was obtained in quantitative yield. The structure of the adduct including the stereochemistry was determined from spectroscopic data, as shown in Scheme 1.

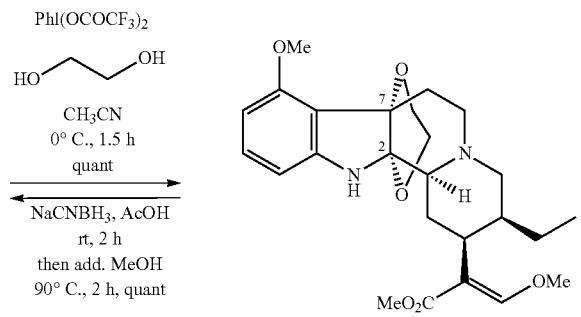

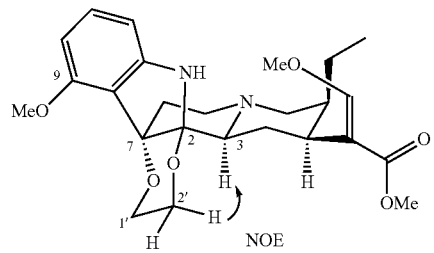

3 mp. 169-172° C.

| $^{13}C$—NMR (δ) | |
|---|---|
| C2 | 90.8 |
| C7 | 81.3 |
| C1' | 62.3 |
| C2' | 61.2 |

Indoline compound 3 could be converted into the starting indole, mitragynine, in almost quantitative yield upon reduction with NaCNBH$_3$ in AcOH at room temperature, followed by heating at 90° C. after addition of MeOH. Indoline 3 was put to practice use for the preparation of several benzene-substituted derivatives for the study of opioid receptor ligands, as described below.

Using other indole alkaloids, the present investigators examined the generality of the newly developed method to mask the pyrrole moiety in the indole nucleus. Among the tested compounds 2,3-dimethylindole, tetaracarbazole, indoloquinolizidine corynantheeol, dihydrocorynantheol, and yohimbine, the corresponding EG adducts (4-9), were obtained in moderate yields. However, the best results (the yields are shown in Scheme 1a) were obtained when NH$_4$Cl was added to the reaction mixture (see Supporting Information).

Scheme 1a: Ethylene glycol adducts of various indoles

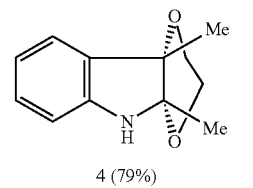

4 (79%)

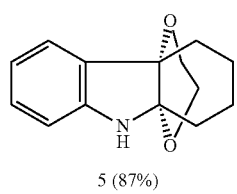

5 (87%)

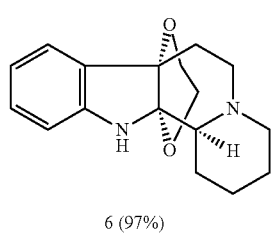

6 (97%)

-continued

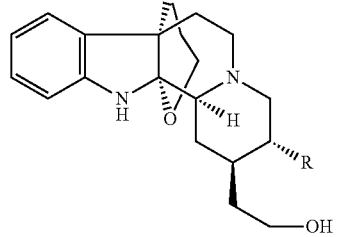

7; R = ethyl (87%)
8: R = vinyl (97%)

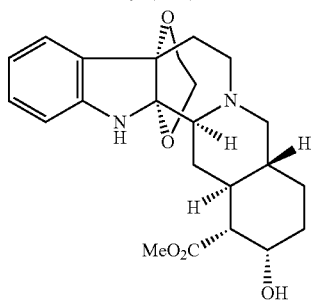

9 (83%)

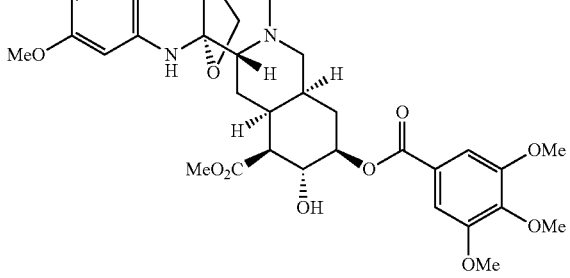

10 (93%)

In the case of reserpine, it was found that phenyliodine diacetate (PIDA) was a more suitable reagent than PIFA for the formation of the EG-bridged adduct (10), which was also useful as a starting material for the preparation of various kinds of A-ring-modified reserpine analogues.

Using EG adduct 3 derived from mitragynine (2), various kinds of substituents were introduced onto the benzene ring as shown in Scheme 2.

Scheme 2

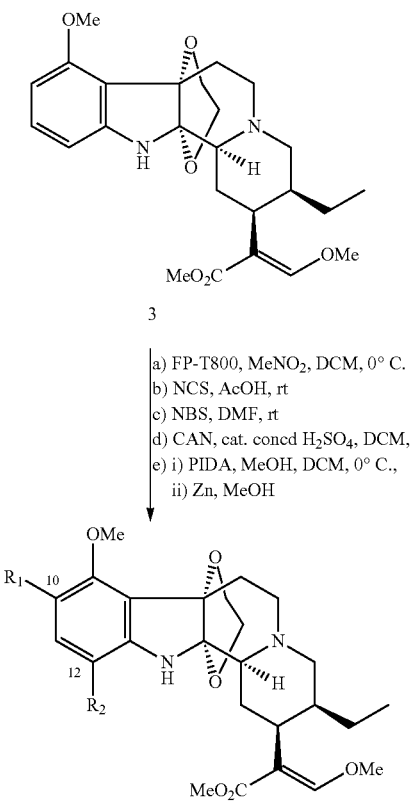

a) FP-T800, MeNO₂, DCM, 0° C.
b) NCS, AcOH, rt
c) NBS, DMF, rt
d) CAN, cat. concd H₂SO₄, DCM, rt
e) i) PIDA, MeOH, DCM, 0° C.,
   ii) Zn, MeOH a) 11; $R_1$ = F, $R_2$ = H (53%)
b) 12a; $R_1$ = Cl, $R_2$ = H (88%), 12b; $R_1$ = H, $R_2$ = Cl (11%)
c) 13a; $R_1$ = Br, $R_2$ = H (75%), 13b; $R_1$ = H, $R_2$ = Br (24%)
d) 14a; $R_1$ = NO₂, $R_2$ = H (52%), 14b; $R_1$ = H, $R_2$ = NO₂ (21%)
e) 15; $R_1$ = OMe, $R_2$ = H (64%, 2 steps)

Treatment of compound 3 with N-fluoro-2,6-dichloropyridinium triflate (FP-T800) gave compound 11 fluorinated at the C-10 position in 53% yield. Exposure of compound 3 to NCS in AcOH afforded two chlorinated derivatives 12a (10-Chloro) and 12b (12-Chloro) in 88% and 11% yields respectively. Using NBS in DMF, 10-bromo and 12-bromo derivatives (13a and 13b) were obtained in 75% and 24% yields, respectively. To introduce a nitro group, for comparison sake, a combination of CAN and concentrated H₂SO₄ in DCM was used to give 14a in 52% yield together with its 12-isomer (14b) in 21% yield. 10-Methoxy derivative 15 was prepared in 64% yield by treatment of compound 3 with IBDA in MeOH, followed by the reduction of the resulting iminoquinone intermediate (see Supporting Information) with Zn in MeOH.

The C10-substituted derivative thus obtained as a major product of each electrophilic aromatic substitution reaction were converted into their indole derivatives in good yields by reduction with NaCNBH₃ in AcOH as described above (conversion from compound 3 into compound 2). However, in the case of nitro derivative 14a, a two-step procedure was used; i.e., compound 14a was treated with TBSOTf in the presence of 2,6-lutadine and the resultant indolenine derivative 16 obtained in 87% yield was reduced with NaCNBH₃ to give the indole derivative 20 in 94% yield (Scheme 3). The thus obtained indole derivatives were, respectively, converted into 7-hydroxyindolenine derivatives (22-25) by oxidation with PIFA in aqueous MeCN.

Scheme 3

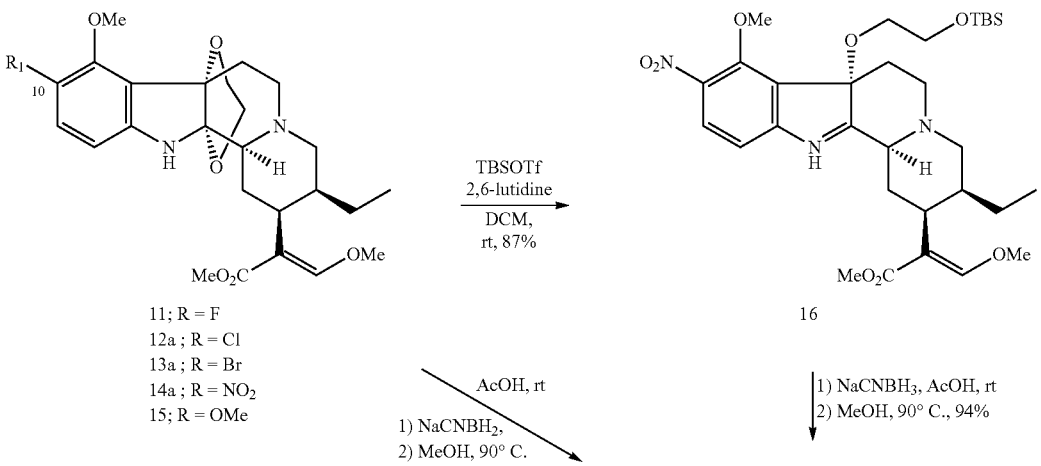

11; R = F
12a; R = Cl
13a; R = Br
14a; R = NO₂
15; R = OMe

TBSOTf
2,6-lutidine
DCM,
rt, 87%

16

AcOH, rt
1) NaCNBH₂,
2) MeOH, 90° C.

1) NaCNBH₃, AcOH, rt
2) MeOH, 90° C., 94%

-continued

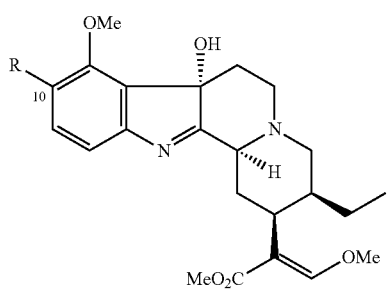

22; R = F (56%)
23; R = Cl (54%)
24; R = Br (33%)
25; R = OMe (20%)

← PIFA aq MeCN

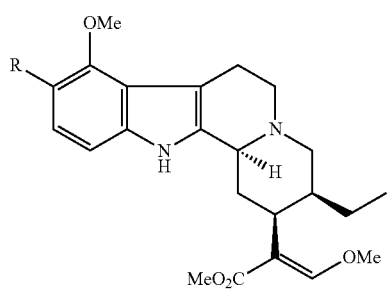

17; R = F (89%)
18; R = Cl (98%)
19; R = Br (91%)
20; R = NO$_2$
21; R = OMe (64%)

Additional details on the experimental procedures used for the preparation of compounds 2-25, and copies of $^1$H and $^{13}$C NMR spectral data for compounds 3-6, 11, 17 and 22 are provided in the Supporting Information included herewith.

Pharmacological Evaluation

The series of C10-substituted mitragynine derivatives obtained by the above reactions were subjected to pharmacological evaluation. The opioid agonistic effect was evaluated in an experiment involving twitch contraction induced by electrical stimulation of guinea pig ileum. This experiment is generally used to study opioid analgesics. Additional details on the experimental procedures used for this evaluation are provided in the Supporting Information. The results are shown in Table A.

TABLE A

Opioid Effects of Mitragynine Derivatives on Twitch Contraction Induced by Electrical Stimulation in Guinea Pig Ileum[a]

| Compound | pD2 value (−log M) | Relative Potency (%) | Maximum inhibition (%) | Inhibitory activity (%) |
|---|---|---|---|---|
| Morphine | 7.15 ± 0.05 | 100 | 87.2 ± 1.8 | 100 |
| Ethylene Glycol Bridged Derivatives | | | | |
| 3 | 7.70 ± 0.10 | 354 | 35.0 ± 11.0 | 40 |
| 11 | 8.40 ± 0.02 | 1778 | 83.4 ± 3.2 | 96 |
| 12a | 7.61 ± 0.17 | 288 | 48.1 ± 9.3 | 55 |
| 14a | 7.88 ± 0.18 | 537 | 65.0 ± 4.3 | 75 |
| Mitragynine Derivatives | | | | |
| 2 | 6.50 ± 0.06 | 22 | 72.0 ± 5.0 | 83 |
| 7-Hydroxyindolenine Derivatives | | | | |
| 1 | 7.78 ± 0.10 | 426 | 90.8 ± 3.4 | 104 |
| 22 | 7.87 ± 0.04 | 524 | 82.5 ± 1.8 | 95 |
| 23 | 7.53 ± 0.08 | 239 | 74.8 ± 3.0 | 86 |
| 24 | 7.45 ± 0.04 | 199 | 61.7 ± 6.2 | 71 |

[a]Potency is expressed as a pD2 value, which is the negative logarithm of the concentration required to produce 50% of the maximum response each compound (EC50). Relative potency is expressed as a percentage the pD2 value of each compound against that of morphine. Maximum inhibition (%), which is elicited by the compound when the response reaches a plateau, was calculated by regarding the twitch contraction as 100%. Relative inhibitory activity, which means intrinsic activity on opioid receptors, is expressed as a percentage of the maximum inhibition by each compound against morphine. Each value represents a mean (SEM) of five or six animals. The asterisk (*) donates values that were significantly different from the morphine group by Student's t-test (**, <0.01). Compounds 13a, 15,17-21, and 25 did not show significant inhibition at 1 μM.

Among the EG-bridged derivatives (3, 11, 12a, 13a, 14a and 15) and the 7-hydroxyindolenine derivatives (22-25) C10-fluorinated derivatives (11, 22) showed the highest potency. Derivatives having a fluoro group at C10 showed the highest potency amongst the C10-halogenated derivatives.

Although not desiring to be bound to any theory, these results suggest that the dimension or electronegativity of the functional group at the C10 position can be useful to elicit opioid agonistic effect. Compound 22 in particular showed potent agonistic effect, but its potency was nearly equal to that of 7-hydroxymitragynine (1).

The results of these experimental studies show a new method to mask the 2,3-π bond of indole alkaloids and the conversion of the protected compounds, i.e., 2,3-ethylene glycol adducts, back to the starting indoles. This procedure was utilized in these studies for the modification of the benzene ring of the indoline derivative and was applied to the preparation of potent opioid receptor agonists with the Corynanthe skeleton, in which the C10-halogenated indole alkaloid compound exhibited more potent opioid agonistic effect than morphine in in vitro experiments.

Example 2

Indole Alkaloid Compounds of Formula Ia

Synthesis of Indole Alkaloid Compounds of Formula Ia

Exemplary indole alkaloid derivative compounds of formulae Ia were prepared by reacting 7-hydroxymitragynine and separately 7-hydroxy-10-halomitragynine with NaBH$_4$, in MeOH, to yield compounds 26 and 27, such as shown in general synthesis Scheme 4.

Scheme 4
Structures and Synthesis Method of Compound 26 and Compound 27

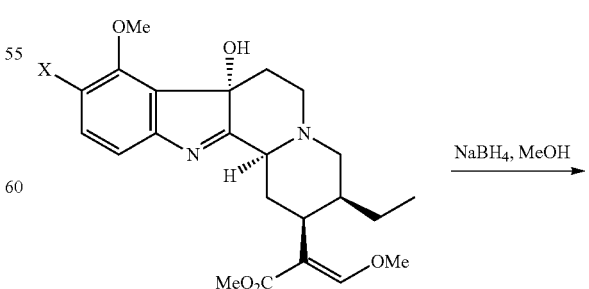

X = H: 7-Hydroxymitragynine
X = F: 10-Fluoro-7-hydroxymitragynine

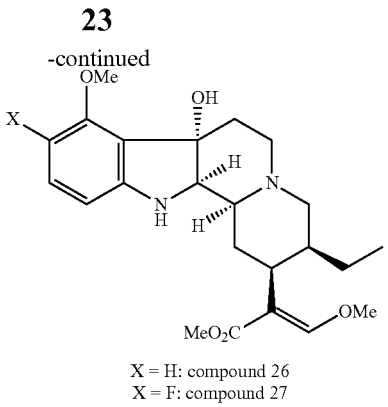

X = H: compound 26
X = F: compound 27

Additional details on the experimental procedures used for the preparation of compounds 26 and 27, and $^1$H and $^{13}$C NMR spectral data for these compounds are provided below.

Preparation of Compound 26.

To a stirred solution of 7-hydroxymitragynine (37.5 mg, 0.091 mmol) in dry MeOH (1.1 mL) was added NaBH$_4$ (4.3 mg, 0.11 mmol) at 0° C. under argon atmosphere. After 30 min, H$_2$O was added to the reaction mixture. The mixture was concentrated under reduced pressure and poured into saturated aqueous NaHCO$_3$ solution, and the whole mixture was extracted with 5% MeOH/CHCl$_3$ three times. The combined extract was washed with brine, dried over MgSO$_4$, and evaporated to give a residue that was purified by silica gel column chromatography (ethyl acetate/n-hexane=35:65) and then crystallized from ethyl acetate to give 26.3 mg of compound 26 (MGM-15) (y. 70%).

Compound 26; m.p.: 219-223° C. (ethyl acetate). UV (MeOH) $\lambda_{max}$ nm (log $\epsilon$): 288 (3.13), 277 (3.06), 239 (4.16), 232 (4.14), 214 (4.50). IR (KBr) $\nu_{max}$ cm$^{-1}$: 3341, 2954, 1698, 1614, 1467, 1283. $^1$H-NMR (500 MHz, CDCl$_3$) δ ppm: 7.40 (1H, s, H-17), 7.00 (1H, dd, J=8.1, 8.1 Hz, H-11), 6.35 (1H, d, J=7.9 Hz, H-12), 6.31 (1H, d, J=8.2 Hz, H-10), 3.87 (1H, br.s, N$_a$—H), 3.83 (3H, s, 9-OCH$_3$), 3.80 (3H, s, 17-OCH$_3$), 3.70 (3H, s, 22-OCH$_3$), 3.47 (1H, br.s, H-2), 2.95 (2H, m, H-15 and H-21), 2.94 (1H, s, 7-OH), 2.53 (2H, m, H-5 and H-14), 2.25 (1H, ddd, J=12.3, 12.3, 2.3 Hz, H-5), 2.16 (2H, m, H-3 and H-21), 2.03 (1H, d, J=14.3 Hz, H-6), 1.92 (1H, ddd, J=13.6, 13.6, 4.3 Hz, H-6), 1.79 (1H, m, H-19), 1.58 (1H, br.d, J=11.3 Hz, H-20), 1.39 (1H, d, J=12.8 Hz, H-14), 1.23 (1H, m, H-19), 0.85 (3H, dd, J=7.3, 7.3 Hz, H$_3$-18). $^{13}$C-NMR (125 MHz, CDCl$_3$) δ ppm: 169.1 (C-22), 160.3 (C-17), 155.9 (C-9), 149.9 (C-13), 129.3 (C-11), 121.3 (C-8), 111.8 (C-16), 105.2 (C-12), 101.9 (C-10), 77.1 (C-7), 69.8 (C-2), 61.6 (17-OCH$_3$), 61.6 (C-3), 58.5 (C-21), 55.1 (9-OCH$_3$), 51.2 (22-OCH$_3$), 50.7 (C-5), 40.7 (C-20), 40.2 (C-15), 35.2 (C-6), 28.5 (C-14), 19.1 (C-19), 13.1 (C-18). EI-MS (%) m/z: 416 (M$^+$, 61), 400 (96), 399 (100), 398 (97), 397 (78), 383 (41), 256 (64), 214 (84). Anal. Calcd for C$_{23}$H$_{32}$O$_5$N$_2$: C, 66.32; H, 7.74; N, 6.73. Found: C, 66.08; H, 7.77; N, 6.71. CD (c=0.29 mM, MeOH, 24° C.), Δ$\epsilon$ (λ nm): 0 (318), (+1.4 (293), 0 (257), −1.0 (248), 0 (233), +0.2 (231), 0 (227), −7.7 (215), +0.1 (208).

Preparation of Compound 27.

To a stirred solution of 10-fluoro7-hydroxymitragynine (23.7 mg, 0.055 mmol) in dry MeOH (0.5 mL) was added NaBH$_4$ (2.1 mg, 0.056 mmol) at 0° C. under argon atmosphere and the reaction mixture was stirred for 30 min. After adding H$_2$O, the reaction mixture was poured into saturated aqueous NaHCO$_3$ solution. The whole mixture was extracted with 5% MeOH/CHCl$_3$ three times. The combined extract was washed with brine, dried over MgSO$_4$, and evaporated to give a residue that was purified by amino-silica gel column chromatography (ethyl acetate/n-hexane=1:1) to give 22.6 mg of compound 27 (MGM-16) (y. 95%).

Compound 27; UV (MeOH) $\lambda_{max}$ nm (log $\epsilon$): 297 (3.13), 276 (3.10), 240 (4.22), 226 (4.11), 205 (4.60). IR (KBr) $\nu_{max}$ cm$^{-1}$: 3364, 2947, 1701, 1626, 1490, 1284, 1240. $^1$H-NMR (500 MHz, CDCl$_3$) δ ppm: 7.41 (1H, s, H-17), 6.76 (1H, dd, J=12.8, 8.2 Hz, H-11), 6.28 (1H, dd, J=8.5, 3.1 Hz, H-12), 4.01 (3H, d, J=2.7 Hz, 9-OCH$_3$), 3.79 (3H, s, 17-OCH$_3$), 3.69 (3H, s, 22-OCH$_3$), 3.46 (1H, d, J=3.1 Hz, H-2), 2.95 (2H, m, H-15 and H-21), 2.77 (1H, br.s, 7-OH), 2.52 (2H, m, H-5 and H-14), 2.25 (1H, m, H-5), 2.15 (2H, m, H-3 and H-21), 1.95 (2H, m, H-6), 1.76 (1H, m, H-19), 1.58 (1H, br.d, J=11.3 Hz, H-20), 1.37 (1H, d, J=12.8 Hz, H-14), 1.23 (1H, m, H-19), 0.84 (3H, dd, J=7.3, 7.3 Hz, H$_3$-18). $^{13}$C-NMR (125 MHz, CDCl$_3$) δ ppm: 169.0 (C-22), 160.3 (C-17), 148.4 (d, J=237.4 Hz, C-10), 145.1 (C-13), 143.2 (d, J=11.9 Hz, C-9), 126.8 (C-8), 116.4 (d, J=21.5 Hz, C-11), 111.7 (C-16), 105.8 (d, J=6.9 Hz, C-12), 77.4 (C-7), 70.0 (C-2), 61.6 (17-OCH$_3$), 61.4 (C-3), 61.2 (d, J=7.8 Hz, 9-OCH$_3$), 58.4 (C-21), 51.2 (22-OCH$_3$), 50.5 (C-5), 40.7 (C-20), 40.1 (C-15), 35.2 (C-6), 28.4 (C-14), 19.0 (C-19), 13.1 (C-18). CD (c=0.26 mM, MeOH, 24° C.), Δ$\epsilon$ (λ nm): 0 (337), +2.7 (297), 0 (255), −4.2 (236), −3.8 (227), −8.4 (214), +0.1 (207). FAB-MS (NBA) m/z: 435 [M+H]$^+$. HR-FAB-MS (NBA/PEG): calcd. for C$_{23}$H$_{32}$O$_5$N$_2$F: 435.2295. found: 435.2301.

Pharmacological Evaluation

Methods

Animals.

Male ddY-strain mice (Japan SLC, Hamamatsu, Japan) weighing 25-33 g and male Hartley-strain guinea-pigs (Japan SLC) weighing 320-550 g were used.

Drugs.

For guinea-pig isolated ileum test, compound 1 and compound 11 were first dissolved in 100% dimethylsulfoxide to yield a 5 mM solution, and then subsequently diluted with distilled water. For mouse tail-flick test and gastrointestinal transit test, compound 1 and compound 11 were dissolved in 25 mM phosphate buffer (pH 5.3-5.5).

Electrical Stimulation of Guinea-Pig Ileum.

These tests were also conducted on compounds 26 and 27, in addition to the compounds previously reported in Table A, and the combined results are set forth in Table 1. The guinea-pig ileum was dissected and placed in Krebs-Henseleit solution (in mM: NaCl, 112.08; KCl, 5.90; CaCl$_2$, 1.97; MgCl$_2$, 1.18; NaH$_2$PO$_4$, 1.22; NaHCO$_3$, 25.00, and glucose, 11.49). The ileum was placed under 1 g tension in a 5 ml organ bath containing the nutrient solution. The bath was maintained at 37° C. and continuously bubbled with a mixture of 95% O$_2$ and 5% CO$_2$. Tissues were stimulated by a platinum needle-ring (the ring was placed 20 mm above the base of a 5 mm long needle) electrode. After equilibration, the ileum was transmurally stimulated with monophasic pulses (0.2 Hz and 0.1 ms duration) by a stimulator (SEN-7203, Nihon Kohden, Tokyo, Japan). Contractions were isotonically recorded by using a displacement transducer (NEC Type 45347, San-ei Instruments Ltd., Tokyo, Japan). The effects of drug treatments on the twitch contractions evoked by transmural stimulation elicited through the ring electrodes were examined. The height of the twitch response to transmural stimulation was measured before and after the drug challenge. The responses were expressed as % inhibition of the twitch response to the transmural stimulation before the drug challenge.

Tail-Flick Test.

Mice respond to a focused heat stimulus by flicking or moving their tail from the path of the stimulus, thereby exposing a photocell located in the tail-flick analgesia meter (Ugo Basile Tail-flick Unit 7360, Ugo Basile, Comerio, Italy) immediately below the tail. The reaction time is automatically recorded. Prior to treatment with drugs, vehicle, or saline, the nociceptive threshold was measured three times, and the mean of the reaction time was used as the pre-drug latency for each mouse. A cut-off time of 10 s was used to prevent tissue damage. Analgesia was quantified using the percentage of maximum possible effect (% MPE) and calculated as: % MPE=[(test latency−pre-drug latency)/(cut-off time−pre-drug latency)]×100.

Gastrointestinal Transit.

Mice were fasted, with water available ad libitum, for 18 h before the experiments. Fifteen minutes after s.c. administration of compound 1, compound 11, morphine, vehicle, or saline, a charcoal meal (an aqueous suspension of 10% charcoal and 5% gum arabic) was orally administered at a volume of 0.25 ml. Fifteen minutes after oral administration of compound 1, compound 11 or vehicle, and 30 min after oral administration of morphine or distilled water, a charcoal meal was orally administered. Thirty minutes after administration of the charcoal meal, the animal was sacrificed by cervical dislocation, and the small intestine from the pylorus to the ileocecum was carefully removed. Both the length of the small intestine from the pylorus to the ileocecum and the farthest distance to which the charcoal meal had traveled were measured. For each animal, the gastrointestinal transit (GIT) was calculated as the percentage of distance traveled by the charcoal meal relative to the total length of the small intestine. The inhibition of gastrointestinal transit (%) was calculated as: Inhibition of gastrointestinal transit (%)=[(saline or vehicle GIT−drug GIT)/(saline or vehicle GIT)]×100.

Statistical Analysis.

The data are expressed as the mean±S.E.M. Statistical analyses were performed with two-tailed Student's t-test for comparison of two groups, and by a one-way analysis of variance followed by a Bonferroni multiple comparison test for comparison of more than two groups. A P value <0.05 was considered statistically significant. $ED_{50}$ values and 95% confidence limits were determined using the Litchfield-Wilcoxon method (1949).

Results and Discussion.

Analgesic effects of compound 1, compound 11, compound 26, compound 27 and morphine were investigated in acute thermal pain tests in mice. The oral administration of compound 1, compound 11, compound 26 and compound 27 exhibited potent and dose-related analgesic effects in the tail-flick test (FIG. 1). The $ED_{50}$ values (95% confidence limits) for the analgesic effects of the oral administration of compound 1, compound 11, compound 26 and compound 27 were 4.43 mg/kg (1.57-6.93 mg/kg), 2.84 mg/kg (1.60-5.05 mg/kg), 1.26 mg/kg (0.84-1.88 mg/kg) and 0.26 mg/kg (0.17-0.42 mg/kg), respectively, in the tail-flick test. Compound 1, compound 11, compound 26 and compound 27 elicit 14, 22, 50 and 240 times, respectively, more potent analgesic effects than morphine in the mouse tail-flick test (Table 2). It is hypothesized that mitragynine-related compounds have a favorable structure for inducing the orally-active analgesic effect.

Site of Action in Analgesic Effects of Compounds.

The in vivo analgesic test revealed that compound 11, compound 26 and compound 27 showed dose-dependent and strong analgesic effects when orally administered to mice. In order to determine the opioid receptor type selectivity of analgesia induced by compound 11, compound 26 and compound 27, mice were pretreated with selective opioid receptor type antagonists in mouse tail-flick test. Doses of compound 11, compound 26 and compound 27 were used and produced a response of 80-90% to detect the effects of the antagonists easily. The analgesic effects of subcutaneously-administered compound 11, compound 26 and compound 27 were completely blocked by the non-selective opioid antagonist naloxone (data not shown).

Figure 2:
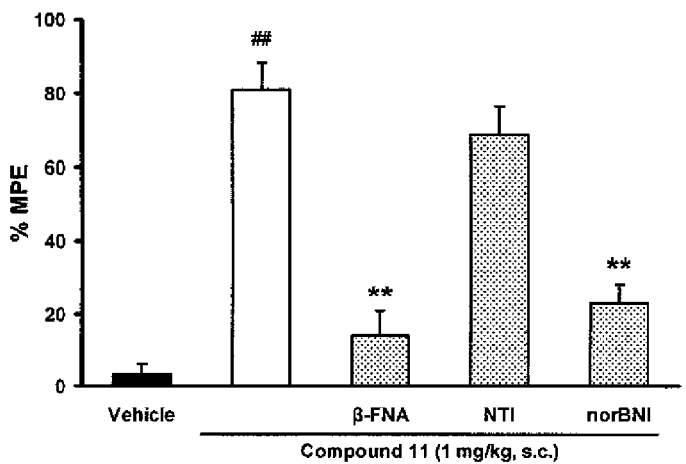
FIG. 2 a)-c) shows effects of opioid receptor antagonists on analgesia induced by subcutaneous (s.c.) administration of compound 11, compound 26 and compound 27, as discussed in Example 2 herein. The analgesic effects were determined in the mouse tail-flick test after s.c. administration of the following antagonists: β-funaltrexamine (β-FNA, 40 mg/kg), naltrindole (NTI, 3 mg/kg), and nor-binaltorphimine (norBNI, 20 mg/kg). Measurements were performed 15 min after s.c. administration of compound 11, compound 26 and compound 27. The doses of compound 11 (1 mg/kg, s.c.), compound 26 (0.5 mg/kg, s.c.) and compound 27 (0.1 mg/kg, s.c.) that produce a response of 80-90% were chosen to detect the effect of each antagonist easily. Each value represents mean±S.E.M. of 8 or 9 mice. The # denotes values that were significantly different from vehicle-treated mice by Student's t-test (##, P<0.01). The asterisk (*) denotes values that were significantly different from mice treated with compound 11, compound 26 and compound 27 alone in one-way analysis of variance followed by Bonferroni multiple comparison test (*, P<0.05, **, P<0.01).
Figure 2:
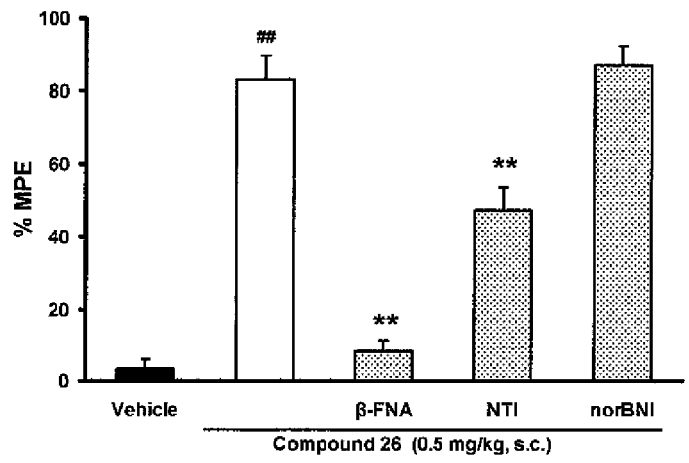
Figure 2:
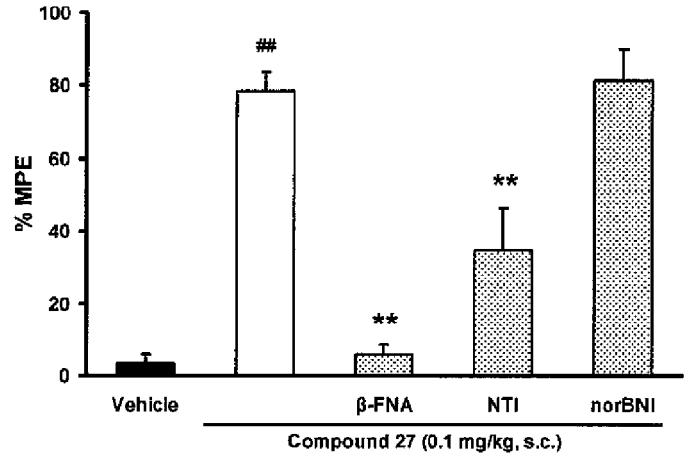

This result suggests the involvement of opioid receptors in their analgesic effects. The effect of compound 11 was markedly inhibited by the μ-opioid receptor selective antagonist β-funaltrexamine and by the κ-opioid receptor selective antagonist nor-binaltorphimine (FIG. 2A). The selective δ-antagonist naltrindole was ineffective on compound 11-induced effect. Taken together, these results indicated that the potent analgesic effect of compound 11 resulted from its combined agonistic action on both μ- and κ-opioid receptors.

On the other hand, the effects of compound 26 and compound 27 were markedly inhibited by the μ-opioid receptor selective antagonist β-funaltrexamine, but were moderately inhibited by the δ-opioid receptor selective antagonist naltrindole (FIG. 2B, C). The selective κ-antagonist nor-binaltorphimine had no effect on their effects. Consequently, these results showed that the potent analgesic effects of compound 26 and compound 27 are attributed to its combined agonistic action on both μ- and δ-opioid receptors.

Weaker Constipating Effects of Compounds than that of Morphine.

Figure 3:
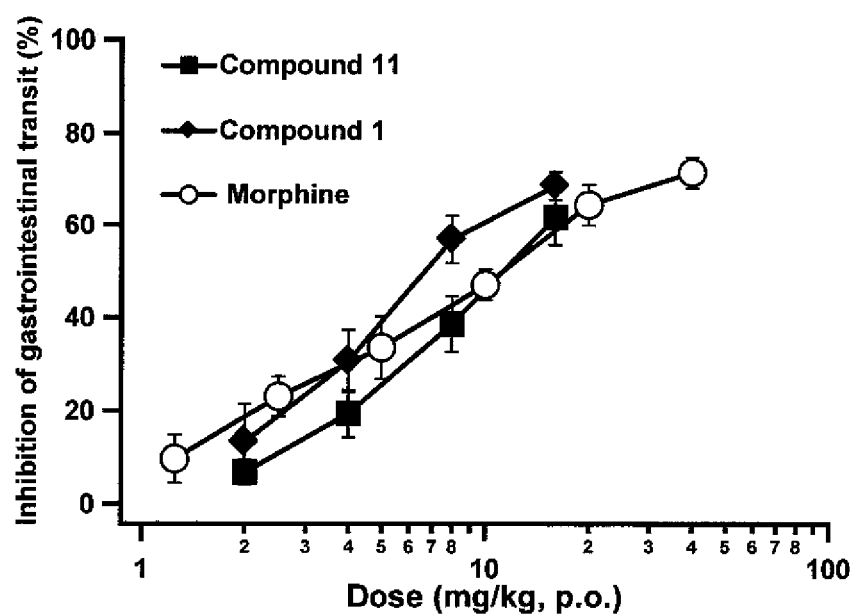
FIG. 3 shows dose-response curves of inhibitory effect on gastrointestinal transit of orally-administered compound 1, compound 11, and morphine in mice, as discussed in Example 2 herein. The inhibition of gastrointestinal transit (%) was calculated as: Inhibition of gastrointestinal transit (%)=[(saline or vehicle GIT−drug GIT)/(saline or vehicle GIT)]×100. Each value represents mean±S.E.M. of 7 or 8 mice.

Constipation is a major problem during chronic administration of opioid analgesics such as morphine. The dose required for its analgesic effect is much higher than that required for its constipating effect. Consequently, constipation is not a clinically negligible issue when morphine is used for the analgesic drug. Then, the inhibition of gastrointestinal transit was studied to evaluate the constipating effect of compound 11 in comparison to morphine and compound 1. The effect of compound 11 on the passage of a charcoal meal was examined after its oral administration in mice. The oral administration of the compound 1, compound 11 and morphine dose-dependently inhibited gastrointestinal transit (FIG. 3). The constipating $ED_{50}$ values (95% confidence limits) for compound 1, compound 11 and morphine were 7.50 mg/kg (3.95-14.2), 11.1 mg/kg (5.96-20.7) and 11.7 mg/kg (5.56-24.6), respectively (Table 2).

The constipating effect of compound 11 was equipotent with morphine and compound 1. The constipating $ED_{50}$ value of compound 11 was 4 times larger than that of its analgesic $ED_{50}$ (Table 2). In the case of morphine, its constipating $ED_{50}$ value was 5 times smaller than its analgesic $ED_{50}$ value. These results suggest that compound 11 induces constipation much less potently than morphine at equi-analgesic dose.

The oral administration of compound 11, compound 26 and compound 27 induced potent analgesic effects in mice. It was surprising that the analgesic effect of compound 27 is 240 fold more potent than that of morphine in their oral administration. The effect of compound 11 was meditated by its agonistic action on both μ- and κ-opioid receptors, while the effect of compound 26 and compound 27 were meditated by their agonistic action on both μ- and δ-opioid receptors. In the gastrointestinal transit study, compound 11 inhibited gastrointestinal transit, but its constipating effect was much weaker than that of morphine at equi-analgesic doses.

The dual acting μ- and κ-opioid agonist, compound 11, and the dual acting μ- and δ-opioid agonists, compound 26 and compound 27, are promising novel analgesics that have more potent analgesic and weaker adverse effects than morphine in clinical management of pain.

TABLE 1

Opioid effects of mitragynine derivatives on twitch contraction induced by electrical stimulation in guinea-pig isolated ileum

| Compound | $pD_2$ value (−log M) | Relative Potency (%) | Maximum inhibition (%) | Inhibitory activity (%) |
|---|---|---|---|---|
| Morphine | 7.15 ± 0.05 | 100 | 87.2 ± 1.8 | 100 |
| Ethylene Glycol Bridged Derivatives | | | | |
| 3 | 7.70 ± 0.10 | 354 | 35.0 ± 11.0 | 40 |
| 11 | 8.40 ± 0.02 | 1778 | 83.4 ± 3.2 | 96 |
| 12a | 7.61 ± 0.17 | 288 | 48.1 ± 9.3 | 55 |
| 14a | 7.88 ± 0.18 | 537 | 65.0 ± 4.3 | 75 |
| Mitragynine Derivatives | | | | |
| 2 | 6.50 ± 0.06 | 22 | 72.0 ± 5.0 | 83 |
| 7-Hydroxyindolenine Derivatives | | | | |
| 1 | 7.78 ± 0.10 | 426 | 90.8 ± 3.4 | 104 |
| 22 | 7.87 ± 0.04 | 524 | 82.5 ± 1.8 | 95 |
| 23 | 7.53 ± 0.08 | 239 | 74.8 ± 3.0 | 86 |
| 24 | 7.45 ± 0.04 | 199 | 61.7 ± 6.2 | 71 |
| 26 | 8.26 ± 0.05 | 1259 | 78.2 ± 3.4 | 90 |
| 27 | 8.81 ± 0.09 | 4571 | 89.0 ± 2.3 | 102 |

Potency is expressed as a $pD_2$ value, which is the negative logarithm of the concentration required to produce 50% of the maximum response each compound ($EC_{50}$). Relative potency is expressed as a percentage the $pD_2$ value of each compound against that of morphine. Maximum inhibition (%), which is elicited by the compound when the response reaches a plateau, was calculated by regarding the twitch contraction as 100%. Relative inhibitory activity, which means intrinsic activity on opioid receptors, is expressed as a percentage of the maximum inhibition by each compound against that by morphine. Each value represents mean ± S.E.M. of data obtained from five or six animals. Compounds 13a, 15, 17-21, and 25 did not show significant inhibition at 1 µM.

TABLE 2

Analgesic effects (tail-flick) and inhibitory effects on gastrointestinal transit (GIT) produced by orally administration of morphine, compound 1, compound 11, compound 26 and compound 27 in mice

| | Compound 1 | Compound 11 | Compound 26 | Compound 27 | Morphine |
|---|---|---|---|---|---|
| Tail-flick | 4.43 (1.57-6.93) | 2.84 (1.60-5.05) | 1.26 (0.84-1.88) | 0.263 (0.165-0.420) | 63.0 (37.2-106.8) |
| GIT | 7.50 (3.95-14.20) | 11.1 (6.0-20.7) | N.D. | N.D. | 11.7 (5.6-24.6) |

$ED_{50}$ represents the median effective dose (mg/kg) (95% confidence limits). N.D.: Not determined.

The disclosures of each patent, patent application and publication cited or described in this document are hereby incorporated herein by reference, in their entirety.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present teachings will be apparent to those skilled in the art from consideration of the present specification and practice of the present teachings disclosed herein. It is intended that the specification and examples be considered as exemplary only and not be limiting of the claims. All cited references, patents, and patent applications are incorporated in their entireties herein by reference.

REFERENCES

Bansinath M, Ramabadran K, Turndorf H, Puig M M (1991) κ-Opiate agonist-induced inhibition of gastrointestinal transit in different strains of mice. *Pharmacology* 42:97-102.

Burkill I H (1935) A Dictionary of the Economic Products of the Malay Peninsula. Vol. II., pp. 1480-1483, Crown Agents for the Colonies, London.

Chavkin C, Goldstein A (1981) Demonstration of a specific dynorphin receptor in guinea pig ileum myenteric plexus. *Nature* 291:591-593.

Cheng Y C, Prusoff W H (1973) Relationship between inhibition constant ($K_1$) and the concentration of inhibitor which causes 50% inhibition ($I_{50}$) of an enzymatic reaction. *Biochem Pharmacol* 22:3099-3108.

Corbett A D, Henderson G, McKnight A T, Paterson S J (2006) 75 years of opioid research: the exciting but vain quest for the Holy Grail. *Br J Pharmacol* 147:S153-162.

Cox B M, Weinstock M (1966) The effect of analgesic drugs on the release of acetylcholine from electrically stimulated guinea-pig ileum. *Br J Pharmacol Chemother* 27:81-92.

D'Amour F E, Smith D L (1941) A method for determining loss of pain sensation. *J Pharmacol Exp Ther* 72:74-79.

Dhawan B N, Cesselin F, Raghubir R, Reisine T, Bradley P B, Portoghese P S, Hamon M (1996) International Union of Pharmacology. XII. Classification of opioid receptors. *Pharmacological Review* 48:567-592.

Funada M, Suzuki T, Narita M, Misawa M, Nagase H (1993) Blockade of morphine reward through the activation of κ-opioid receptors in mice. *Neuropharmacology* 32:1315-1323.

Grewal K S (1932) Observations on the pharmacology of mitragynine. *J Pharmacol Exp Ther* 46:251-271.

Horie S, Koyama F, Takayama H, Ishikawa H, Aimi N, Ponglux D, Matsumoto K, Murayama T (2005) Indole alkaloids of a Thai medicinal herb, *Mitragyna speciosa*, that has opioid agonistic effect in guinea-pig ileum. *Planta Med* 71:231-236.

Hughes J, Kosterlitz H W, Leslie F M (1975) Effect of morphine on adrenergic transmission in the mouse vas deferens. Assessment of agonist and antagonist potencies of narcotic analgesics. *Br J Pharmacol* 53:371-381.

Kuzmin A, Sandin J, Terenius L, Ogren S O (2000) Dose- and time-dependent bimodal effects of kappa-opioid agonists on locomotor activity in mice. *J Pharmacol Exp Ther* 295:1031-1042.

Litchfield J T, Wilcoxon F (1949) A simplified method of evaluating dose-effect experiments. *J Pharmacol Exp Ther* 96:99-113.

Matthes H W, Maldonado R, Simonin F, Valverde O, Slowe S, Kitchen I, Befort K, Dierich A, Le Meur M, Dolle P, Tzavara E, Hanoune J, Rogues B P, Kieffer B L (1999) Loss of morphine-induced analgesia, reward effect and withdrawal symptoms in mice lacking the µ-opioid-receptor gene. *Nature* 383:819-823.

Matsumoto K, Hatori Y, Murayama T, Tashima K, Wongseripipatana S, Misawa K, Kitajima M, Takayama H, Horie S (2006b) Involvement of μ-opioid receptors in antinociception and inhibition of gastrointestinal transit induced by 7-hydroxymitragynine, isolated from Thai herbal medicine *Mitragyna speciosa*. *Eur J Pharmacol* 549:63-70.

Matsumoto K, Horie S, Ishikawa H, Takayama H, Aimi N, Ponglux D, Watanabe K (2004) Antinociceptive effect of 7-hydroxymitragynine in mice: Discovery of an orally active opioid analgesic from the Thai medicinal herb *Mitragyna speciosa*. *Life Sci* 74:2143-2155.

Matsumoto K, Horie S, Takayama H, Ishikawa H, Aimi N, Ponglux D, Murayama T, Watanabe K (2005) Antinociception, tolerance and withdrawal symptoms induced by 7-hydroxymitragynine, an alkaloid from the Thai medicinal herb *Mitragyna speciosa*. *Life Sci* 78:2-7.

Matsumoto K, Mizowaki M, Suchitra T, Takayama H, Sakai S, Aimi N, Watanabe H (1996) Antinociceptive action of mitragynine in mice: evidence for the involvement of supraspinal opioid receptors. *Life Sci* 59:1149-55.

Matsumoto K, Takayama H, Ishikawa H, Aimi N, Ponglux D, Watanabe K, Horie S (2006a) Partial agonistic effect of 9-hydroxycorynantheidine on mu-opioid receptor in the guinea-pig ileum. *Life Sci* 78:2265-2271.

Matsumoto K, Yamamoto L T, Watanabe K, Yano S, Shan J, Pang P K, Ponglux D, Takayama H, Horie S (2005) Inhibitory effect of mitragynine, an analgesic alkaloid from Thai herbal medicine, on neurogenic contraction of the vas deferens. *Life Sci* 78:187-194.

McCurdy C R, Scully S S (2005) Analgesic substances derived from natural products (natureceuticals). *Life Sci* 78:476-484.

Megens A A, Artois K, Vermeire J, Meert T, Awouters F H (1998) Comparison of the analgesic and intestinal effects of fentanyl and morphine in rats. *J Pain Symptom Manage* 15:253-258.

Narita M, Funada M, Suzuki T (2001) Regulations of opioid dependence by opioid receptor types. *Pharmacol Ther* 89:1-15.

Narita M, Mizuo K, Mizoguchi H, Sakata M, Narita M, Tseng L F, Suzuki T (2003) Molecular evidence for the functional role of dopamine D3 receptor in the morphine-induced rewarding effect and hyperlocomotion. *J Neurosci* 23:1006-1012

Narita M, Takahashi Y, Takamori K, Funada M, Suzuki T, Misawa M, Nagase H (1993) Effects of kappa-agonist on the antinociception and locomotor enhancing action induced by morphine in mice. *Jpn J Pharmacol.* 62:15-24.

Neumeyer J L, Bidlack J M, Zong R, Bakthavachalam V, Gao P, Cohen D J, Negus S S, Mello N K (2000) Synthesis and opioid receptor affinity of morphinan and benzomorphan derivatives: mixed kappa agonists and mu agonists/antagonists as potential pharmacotherapeutics for cocaine dependence. *J Med Chem* 43:114-22.

Roy S, Liu H C, Loh H H (1998) μ-Opioid receptor-knockout mice: the role of μ-opioid receptor in gastrointestinal transit. *Brain Res Mol. Brain Res* 56:281-283.

Suwanlert S (1975) A study of kratom eaters in Thailand. *Bull Narc* 27:21-27.

Takayama H (2004) Chemistry and pharmacology of analgesic indole alkaloids from the rubiaceous plant, *Mitragyna speciosa*. *Chem Pharm Bull* 52:916-928.

Takayama H, Ishikawa H, Kurihara M, Kitajima M, Aimi N, Ponglux D, Koyama F, Matsumoto K, Moriyama T, Yamamoto L T, Watanabe K, Murayama T, Horie S (2002) Studies on the synthesis and opioid agonistic activities of mitragynine-related indole alkaloids: discovery of opioid agonists structurally different from other opioid ligands. *J Med Chem* 45:1949-1956.

Takayama H., Misawa K, Okada N, Ishikawa H, Kitajima M, Hatori Y, Murayama T, Wongseripipatana S, Tashima K, Matsumoto K and Horie S (2006) New procedure to mask the 2,3-π bond of the indole nucleus and its application to the preparation of potent opioid receptor agonists with a Corynanthe skeleton. *Org Lett* 8:5705-5708.

Thongpradichote S, Matsumoto K, Thoda M, Takayama H, Aimi N, Sakai S, Watanabe H (1998) Identification of opioid receptor subtypes in antinociceptive actions of supraspinally-administered mitragynine in mice. *Life Sci* 62:1371-1378.

Watanabe K, Yano S, Horie S, Yamamoto L T (1997) Inhibitory effect of mitragynine, an alkaloid with analgesic effect from Thai medicinal plant *Mitragyna speciosa*, on electrically stimulated contraction of isolated guinea-pig ileum through the opioid receptor. *Life Sci* 60:933-942.

Yamamoto L T, Horie S, Takayama H, Aimi N, Sakai S, Yano S, Shan J, Pang P K T, Ponglux D, Watanabe K (1999) Opioid receptor agonistic characteristics of mitragynine pseudoindoxyl in comparison with mitragynine derived from Thai medicinal plant *Mitragyna speciosa*. *Gen Pharmacol* 33:73-81.

Supporting Information for Examples (Example 1)

General

UV: recorded in MeOH on a JASCO V-560 instrument. IR: recorded on a JASCO FT/IR-230 spectrophotometer. $^1$H and $^{13}$C NMR: recorded on a JEOL JNM A-400, JNM A-500, JNM ECP-400 or JNM ECP-600 spectrometer, J values are given in Hz. EI-MS: direct probe insertion at 70 eV recorded on a JEOL JMS GC-mate spectrometer. FAB-MS: recorded on a JEOL JMS-AX500 or JMS-HX110 mass spectrometer. Optical rotation: measured with a JASCO P-1020 polarimeter. CD: measured with a JASCO J-720WI. Elemental analysis: performed on a Perkin-Elmer 240, 2408 Elemental Analyzer. Melting point: measured with a Yanagimoto Micro Melting Point Apparatus 1631A. TLC: precoated Kieselgel 60 $F_{254}$ plates (Merck, 0.25 mm thick). Column chromatography: Kieselgel 60 [Merck, 70-230 mesh (for open chromatography) and 230-400 mesh (for flash chromatography)], Chromatorex NH [Fuji Silysia Chemical, 100-200 mesh (for amino-silica gel column chromatography)]. Medium pressure liquid chromatography (MPLC): C. I. G prepacked column CPS-HS-221-05 (Kusano Kagakukikai, $SiO_2$).

Preparation of Ethylene Glycol-Bridged Compound 3 from Mitragynine (2)

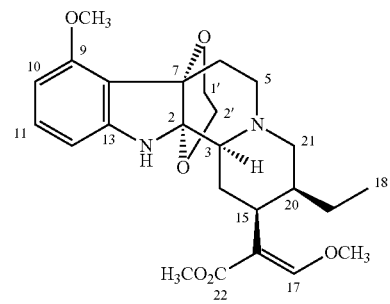

To a solution of mitragynine (2, 102 mg, 0.26 mmol) in dry MeCN (2.0 mL) were added dry ethylene glycol (2.0 mL) and PIFA (113.5 mg, 0.26 mmol) at 0° C. and the mixture was stirred for 1 h at 0° C. under argon atmosphere. After adding chilled aqueous NaHCO₃ solution, the mixture was extracted three times with chloroform. The combined extract was washed with brine, dried over MgSO₄, and evaporated. The crude product was chromatographed on amino-silica gel (ethyl acetate/n-hexane=30:70) to give 120.4 mg (quantitative) of 3 as a colorless amorphous powder, a portion of which was recrystallized from acetone to give pale yellowish prisms (mp. 169-172° C.). Ethylene glycol-bridged Compound 3; UV (MeOH) $\lambda_{max}$ nm (log ε): 285 (3.35), 277 (3.32), 238 (4.26), 229 (4.22), 213 (4.64). IR (ATR) $v_{max}$ cm$^{-1}$: 3255, 2929, 1694, 1646, 1605, 1458, 1255. $^1$H-NMR (500 MHz, CDCl₃) δ ppm: 7.41 (1H, s, H-17), 7.08 (1H, dd, J=8.1, 8.1 Hz, H-11), 6.39 (1H, d, J=8.2 Hz, H-10), 6.37 (1H, d, J=7.9 Hz, H-12), 4.25 (1H, br.s, $N_a$—H), 3.93 (1H, ddd, J=11.8, 11.8, 2.7 Hz, H-2'), 3.85 (3H, s, 9-OCH₃), 3.84 (1H, m, H-1', overlapped with 9-OCH₃), 3.79 (3H, s, 17-OCH₃), 3.70 (3H, s, 22-OCH₃), 3.67 (1H, dd, J=11.6, 2.4 Hz, H-1'), 3.42 (1H, dd, J=11.7, 2.3 Hz, H-2'), 2.98 (1H, dd, J=11.4, 2.0 Hz, H-21), 2.92 (1H, ddd, J=13.4, 3.6, 3.6 Hz, H-15), 2.48 (1H, m, H-5), 2.46 (1H, m, H-3), 2.38-2.29 (2H, m, H-5 and H-14), 2.26 (1H, dd, J=11.3, 2.7 Hz, H-21), 2.15 (1H, ddd, J=14.6, 2.4, 2.4 Hz, H-6), 1.85 (1H, m, H-6), 1.80 (1H, m, H-14), 1.73 (1H, m, H-19), 1.56 (1H, br. d, J=11.3 Hz, H-20), 1.25 (1H, m, H-19), 0.84 (3H, dd, J=7.3, 7.3 Hz, H₃-18). $^{13}$C-NMR (100 MHz, CDCl₃) δ ppm: 169.1 (C-22), 160.4 (C-17), 156.9 (C-9), 149.0 (C-13), 129.9 (C-11), 115.8 (C-8), 111.7 (C-16), 105.3 (C-12), 102.8 (C-10), 90.8 (C-2), 81.3 (C-7), 62.3 (C-1'), 61.6 (17-OCH₃), 61.2 (C-2'), 60.8 (C-3), 58.5 (C-21), 55.3 (9-OCH₃), 51.3 (22-OCH₃), 50.2 (C-5), 40.5 (C-20), 40.1 (C-15), 35.4 (C-6), 24.2 (C-14), 19.2 (C-19), 13.1 (C-18). CD (c=0.21 mM, MeOH, 24° C.), Δε (λ nm): 0 (303), −2.4 (286), 0 (263), +0.7 (256), 0 (250), −1.0 (233), −30.2 (211), −9.4 (200). FAB-MS (NBA) m/z: 459 [M+H]⁺. HR-FAB-MS (NBA/PEG): calcd. for $C_{25}H_{35}N_2O_6$: 459.2495, found: 459.2515. Anal. Calcd for $C_{25}H_{34}N_2O_6 \cdot H_2O$: C, 63.00; H, 7.61; N, 5.88. Found: C, 63.26; H, 7.75; N, 5.73. FIG. 4a is the 1H-NMR for Ethylene Glycol-Bridged Compound 3 and FIG. 4b is the 13C-NMR for Ethylene Glycol-Bridge Compound 3.

Conversion of 3 to Mitragynine (2)

To a stirred solution of 3 (24.6 mg, 0.05 mmol) in dry AcOH (0.6 mL) was added NaCNBH₃ (19.2 mg, 0.29 mmol) at room temperature and the mixture was stirred for 2 h at room temperature under argon atmosphere. MeOH (20 µL) was added to the reaction mixture, which was then heated under reflux at 90° C. for 4 h. The reaction mixture was poured into cold aqueous NH₄OH solution, and this was extracted three times with chloroform. The combined extract was washed with brine, dried over MgSO₄, and evaporated to give a residue that was purified by silica gel column chromatography (ethyl acetate/n-hexane=50:50) to give 21.7 mg (quantitative) of mitragynine (2), which was completely identical with the authentic sample.

Preparation of Compound 4

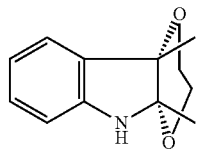

Figure 5A:
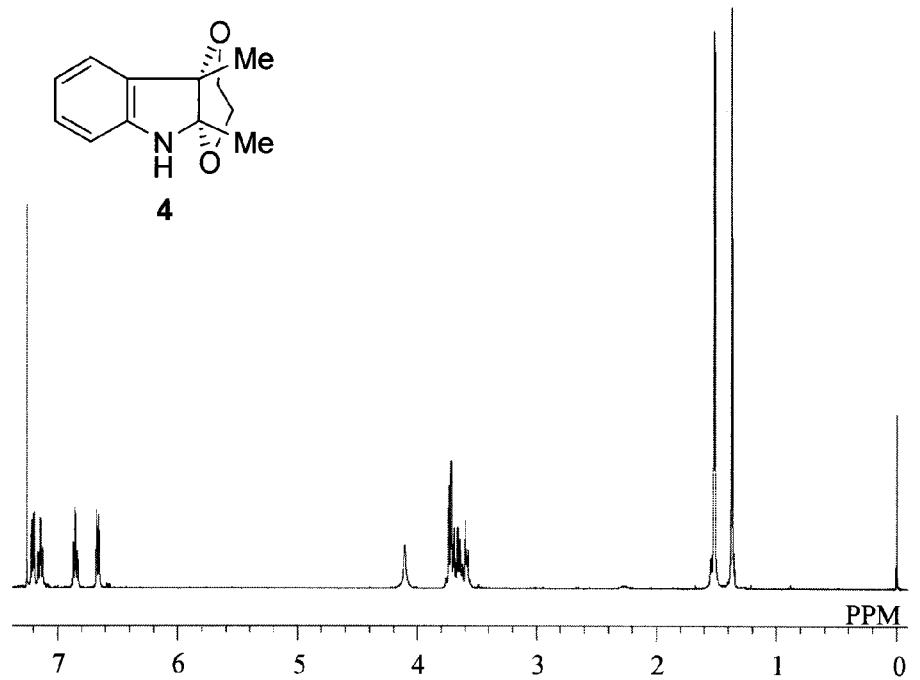
FIG. 5a is the 1H-NMR for Compound 4 and FIG. 5b is the 13C-NMR for Compound 4.
Figure 5B:
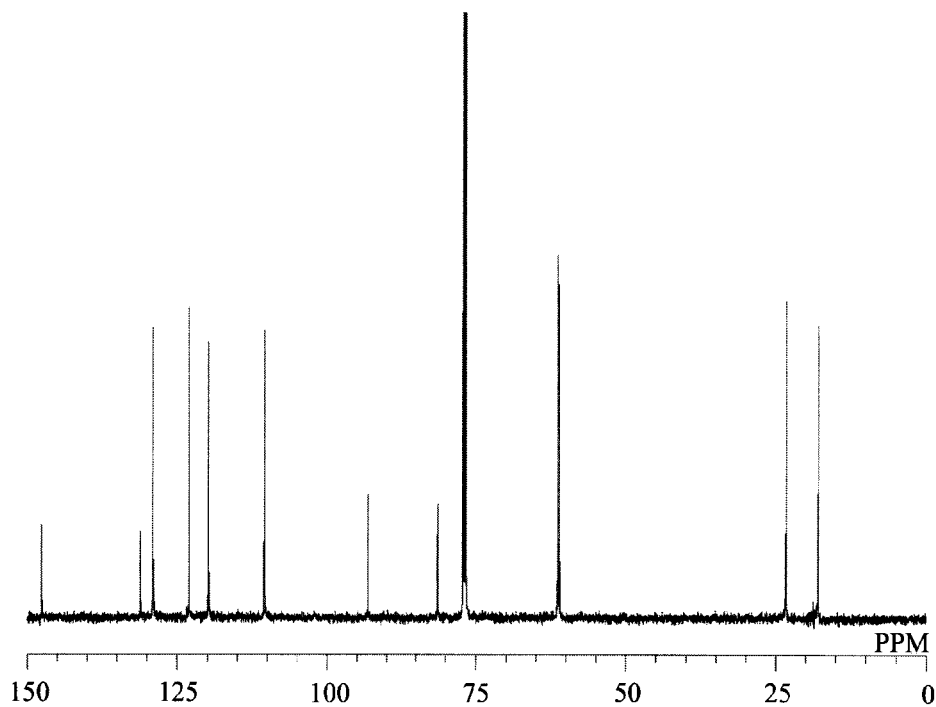

To a stirred solution of 2,3-dimethylindole (74.3 mg, 0.51 mmol) in dry MeCN (2.6 mL) and dry ethylene glycol (2.6 mL) were successively added NH₄Cl (132.2 mg, 2.45 mmol) and PIFA (251.5 mg, 0.61 mmol) at 0° C. and the mixture was stirred for 1 h at 0° C. under argon atmosphere. After adding chilled aqueous NaHCO₃ solution, the mixture was extracted three times with chloroform. The combined extract was washed with brine, dried over MgSO₄, and evaporated. The crude product was purified by pre-packed silica gel column chromatography (ethyl acetate/n-hexane=30:70) to give 83.1 mg (79%) of 4 as a yellowish amorphous powder, a portion of which was recrystallized from n-hexane to give yellowish prisms (mp. 79-81° C., cap.). Compound 4; UV (MeOH) $\lambda_{max}$ nm: 290, 269, 241, 233, 220, 218, 104. IR (KBr) $v_{max}$ cm$^{-1}$: 3329, 2979, 2960, 2864, 1612, 1468. $^1$H-NMR (400 MHz, CDCl₃) δ ppm: 7.21 (1H, d, J=7.3 Hz, H-5), 7.15 (1H, ddd, J=7.7, 7.7, 1.3 Hz, H-7), 6.86 (1H, ddd, J=7.4, 7.4, 0.9 Hz, H-6), 6.71 (1H, d, J=7.9 Hz, H-8), 4.11 (1H, br. s, $N_a$—H), 3.72 (2H, m, H-1' and H-2'), 3.65 (1H, m, H-2'), 3.58 (1H, m, H-1'), 1.56 (3H, s, 2-CH₃), 1.38 (3H, s, 3-CH₃). $^{13}$C-NMR (100 MHz, CDCl₃) δ ppm: 147.6 (C-9), 131.1 (C-4), 129.0 (C-7), 123.1 (C-5), 119.8 (C-6), 110.5 (C-8), 93.2 (C-2), 81.5 (C-3), 61.3 (C-2'), 61.1 (C-1'), 23.3 (2-CH₃), 18.0 (3-CH₃). $[\alpha]_D^{25}$ 0 (c 1.0, CHCl₃). FAB-MS (NBA) m/z: 206 [M+H]⁺. HR-FAB-MS (NBA/PEG): calcd. for $C_{12}H_{16}NO_2$: 206.1181, found: 206.1180. FIG. 5a is the 1H-NMR for Compound 4 and FIG. 5b is the 13C-NMR for Compound 4.

Preparation of Compound 5

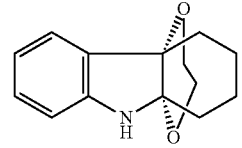

To a stirred solution of tetrahydrocarbazole (1110.9 mg, 0.65 mmol) in dry MeCN (3.3 mL) and dry ethylene glycol (3.3 mL) were successively added NH₄Cl (167.8 mg, 2.60 mmol) and PIFA (335.6 mg, 0.78 mmol) at 0° C. and the mixture was stirred for 30 min at 0° C. under argon atmosphere. After adding chilled aqueous NaHCO₃ solution, the mixture was extracted three times with chloroform. The combined extract was washed with brine, dried over MgSO₄, and evaporated. The crude product was chromatographed on silica gel (ethyl acetate/n-hexane=0:100-50:50) to give 129.5 mg (87%) of 5 as a colorless amorphous powder, a portion of which was recrystallized from ethyl acetate to give colorless prisms (mp. 156-157° C., cap.). Compound 5; UV (MeOH) $\lambda_{max}$ nm: 295, 275, 247, 223, 205. IR (KBr) $v_{max}$ cm$^{-1}$: 3311, 3035, 2958, 2933, 2864, 1616. $^1$H-NMR (400 MHz, CDCl₃) δ ppm: 7.18 (1H, d, J=7.3 Hz, H-9), 7.14 (1H, ddd, J=7.6, 7.6, 1.2 Hz, H-11), 6.85 (1H, dd, J7.4, 7.4 Hz, H-10), 6.71 (1H, d, J=7.6 Hz, H-12), 4.01 (1H, br. s, $N_a$—H), 3.81 (2H, overlapped, H-1' and H-2'), 3.65 (2H, overlapped, H-1' and H-2'), 2.12 (1H, ddd, J=10.4, 10.4, 2.7), 2.00 (1H, m), 1.70 (2H, m), 1.52 (3H, m), 1.42 (1H, m) $^{13}$C-NMR (100 MHz, CDCl₃) δ ppm: 147.4 (C-13), 131.6 (C-8), 128.8 (C-11), 122.4 (C-9), 119.7 (C-10), 111.1 (C-12), 92.3 (C-2), 80.6 (C-7), 61.4 (C-1'), 61.0 (C-2'), 36.4, 29.4, 22.9, 20.6. $[\alpha]_D^{25}$ +1 (c 1.0, CHCl₃). FAB-MS (NBA) m/z: 231 [M]⁺. HR-FAB-MS (NBA/PEG): calcd. for $C_{14}H_{17}NO_2$: 231.1259, found: 231.1269. FIG. 6a is the 1H-NMR for Compound 5 and FIG. 6b is the 13C-NMR for Compound 5.

Preparation of Compound 6

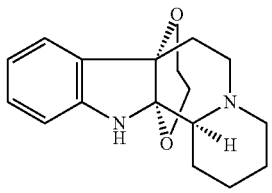

To a stirred solution of indoloquinolizidine (70.4 mg, 0.31 mmol) in dry MeCN (1.6 mL) and dry ethylene glycol (1.6 mL) were successively added NH$_4$Cl (83.2 mg, 1.55 mmol) and PIFA (157.8 mg, 0.37 mmol) at room temperature and the mixture was stirred for 2 h at 50° C. under argon atmosphere. After adding chilled aqueous NaHCO$_3$ solution, the mixture was extracted three times with chloroform. The combined extract was washed with brine, dried over MgSO$_4$, and evaporated. The crude product was purified by pre-packed silica gel column chromatography (5% MeOH in CHCl$_3$) to give 86.0 mg (97%) of 6 as a colorless amorphous powder, a portion of which was recrystallized from acetone and n-hexane to give colorless prisms (mp. 142-143° C., cap.). Compound 6; UV (MeOH) $\lambda_{max}$ nm: 290, 262, 238, 221, 206. IR (ATR) $v_{max}$ cm$^{-1}$: 3313, 3033, 2964, 2939, 2924, 2910, 1614. $^1$H-NMR (500 MHz, CDCl$_3$) δ ppm: 7.18 (1H, dd, J=7.2, 0.6 Hz, H-9), 7.14 (1H, ddd, J=7.6, 7.6, 1.3 Hz, H-11), 6.86 (1H, ddd, J=7.4, 7.4, 0.9 Hz, H-10), 6.71 (1H, d, J=7.7 Hz, H-12), 4.20 (1H, br. s, N$_a$—H), 3.90 (2H, overlapped, H-1' and H-2'), 3.61 (1H, m, H-1' or H-2'), 3.44 (1H, m, H-1' or H-2'), 2.99 (1H, d, J=11.0 Hz), 2.57 (1H, m), 2.50 (1H, dd, J=10.9, 2.1 Hz, H-3), 2.41 (1H, ddd, J=12.3, 12.3, 2.5 Hz), 2.16 (1H, ddd, J=11.1, 11.1, 4.3 Hz), 2.05 (1H, d, J=10.3 Hz), 1.91 (2H, m), 1.80 (1H, ddd, J=13.8, 13.8, 4.5 Hz), 1.68 (2H, m), 1.43 (1H, m), 1.33 (1H, m). $^{13}$C-NMR (100 MHz, CDCl$_3$) δ ppm: 146.8 (C-13), 130.8 (C-8), 128.6 (C-11), 122.0 (C-9), 119.9 (C-10), 111.8 (C-12), 91.1 (C-2), 80.4 (C-7), 62.0 and 61.2 (C-1' and C-2'), 59.5, 56.5, 50.6, 37.4, 25.5, 24.8, 24.6. $[\alpha]_D^{24}$ +1 (c 0.8, CHCl$_3$). FAB-MS (NBA) m/z: 287 [M+H]$^+$. HR-FAB-MS (NBA/PEG): calcd. for C$_{17}$H$_{23}$N$_2$O$_2$: 287.1760, found: 287.1762. FIG. 7a is the 1H-NMR for Compound 6 and FIG. 7b is the 13C-NMR for Compound 6.

Preparation of Compound 7

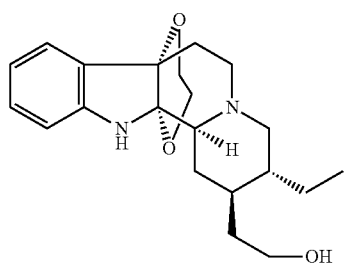

To a stirred solution of dihydrocorynantheol (229 mg, 0.77 mmol) in dry MeCN (4.0 mL) and dry ethylene glycol (4.0 mL) was added NH$_4$Cl (55.4 mg, 1.04 mmol), and PEFA was added portionwise to the stirred mixture at room temperature under argon atmosphere in the following manner: 0 min, 157.6 mg (0.37 mmol); 1 h, 175.7 mg (0.41 mmol); 4 h, 37.5 mg (0.08 mmol). The reaction mixture was stirred at the same temperature for further 3 h under argon atmosphere. After adding chilled aqueous NaHCO$_3$ solution, the mixture was extracted three times with chloroform. The combined extract was washed with brine, dried over MgSO$_4$, and evaporated. The crude product was chromatographed on amino-silica gel (ethyl acetate/chloroform=30:70) to give 238.7 mg (87%) of 7 as a colorless amorphous powder, a portion of which was recrystallized from ethyl acetate and n-hexane to give colorless prisms (mp. 108-111° C. cap.). Compound 7; UV (MeOH) $\lambda_{max}$ nm: 292, 264, 239, 221, 205. IR (ATR) $v_{max}$ cm$^{-1}$: 3313, 2958, 2866, 1614, 1466. $^1$H-NMR (500 MHz, CDCl$_3$) δ ppm: 7.17 (1H, d, J=7.0 Hz, H-9), 7.13 (1H, ddd, J=7.6, 7.6, 1.2 Hz, H-11), 6.86 (1H, ddd, J=7.3, 7.3, 0.9 Hz, H-10), 6.71 (1H, d, J=7.6 Hz, H-12), 4.23 (1H, br. s, N$_a$—H), 3.89 (2H, overlapped, H-1' and H-2'), 3.75 (2H, m, H$_2$-17), 3.61 (1H, m, H-1'), 3.44 (1H, m, H-2'), 3.05 (1H, dd, J=11.3, 3.6 Hz, H-21), 2.60 (1H, dddd, J=11.6, 2.2, 2.2, 2.2 Hz, H-5), 2.51 (1H, dd, J=11.1, 1.9 Hz, H-3), 2.39 (1H, ddd, J=12.4, 12.4, 2.4 Hz, H-5), 2.15 (1H, ddd, J=12.0, 2.8, 2.8 Hz, H-14), 1.96 (2H, overlapped, H-6 and H-16), 1.88 (1H, dd, J=11.3, 11.3 Hz, H-21), 1.80 (1H, ddd, J=13.8, 13.8, 4.4 Hz, H-6), 1.67 (1H, m, H-19), 1.38 (3H, overlapped, H-15, H-16 and H-20), 1.24 (1H, ddd, J=11.6, 11.6, 11.6 Hz, H-14), 1.11 (1H, m, H-19), 0.89 (3H, dd, J=7.5, 7.5 Hz, H$_3$-18). $^{13}$C-NMR (100 MHz, CDCl$_3$) δ ppm: 146.7 (C-13), 130.8 (C-8), 128.7 (C-11), 122.0 (C-9), 119.9 (C-10), 111.8 (C-12), 91.1 (C-2), 80.3 (C-7), 62.0 (C-1'), 61.3 (C-2'), 61.0 (C-21), 60.5 (C-17), 59.1 (C-3), 50.3 (C-5), 41.5 (C-20), 37.4 (C-6), 37.0 (C-15), 35.8 (C-16), 30.5 (C-14), 23.3 (C-19), 11.0 (C-18). $[\alpha]_D^{25}$ −72 (c 1.1, CHCl$_3$). EI-MS m/z (%): 358 (100, M$^+$), 313 (20), 169 (95), 156 (41). HR-FAB-MS (NBA/PEG): calcd. for C$_{21}$H$_{31}$N$_2$O$_3$: 359.2335, found: 359.2344.

Preparation of Compound 8

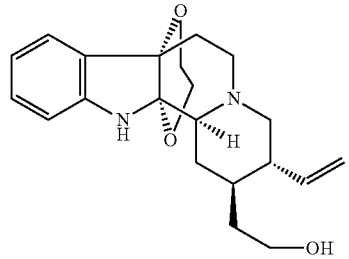

To a stirred solution of corynantheol (302 mg, 1.02 mmol) in dry MeCN (15.0 mL) and dry ethylene glycol (15.0 mL) was added NH$_4$Cl (107.4 mg, 2.01 mmol), and PIFA was added portionwise to the stirred mixture at 0° C. under argon atmosphere in the following manner: 0 min, 139.1 mg (0.32 mmol); 10 min, 142.3 mg (0.33 mmol); 20 min, 175.5 mg (0.41 mmol); 30 min, 100.5 mg (0.23 mmol). The reaction mixture was stirred at room temperature for further 15 h under argon atmosphere. After adding chilled aqueous NaHCO$_3$ solution, the mixture was extracted three times with chloroform. The combined extract was washed with brine, dried over MgSO$_4$, and evaporated. The crude product was chromatographed on amino-silica gel (ethyl acetate/chloroform=30:70) to give 352.9 mg (97%) of 8 as a yellowish amorphous powder, a portion of which was recrystallized from ethyl acetate and n-hexane to give colorless prisms (mp. 105-110° C., cap.). Compound 8; UV (MeOH) $\lambda_{max}$ nm: 291, 265, 239, 222, 205. IR (KBr) $v_{max}$ cm$^{-1}$: 3315, 2924, 2866, 2821, 1614, 1466. $^1$H-NMR (500 MHz, CDCl$_3$) δ ppm: 7.18 (1H, d, J=7.3 Hz, H-9), 7.14 (1H, ddd, J=7.6, 7.6, 1.3 Hz, H-11), 6.87 (1H, dd, J=7.3, 7.3 Hz, H-10), 6.72 (1H, d, J=7.6 Hz, H-12), 5.58 (1H, ddd, J=17.2, 10.2, 8.9 Hz, H-19), 5.12

(1H, dd, J=17.2, 1.7 Hz, H-18), 5.09 (1H, dd, J=10.2, 1.7 Hz, H-18), 4.23 (1H, br. s, $N_a$—H), 3.89 (2H, overlapped, H-1' and H-2'), 3.75 (2H, m, $H_2$-17), 3.61 (1H, m, H-1'), 3.44 (1H, m, H-2'), 2.89 (1H, dd, J=11.1, 3.7 Hz, H-21), 2.57 (2H, m, overlapped H-3 and H-5), 2.40 (1H, ddd, J=12.4, 12.4, 2.4 Hz, H-5), 2.19 (2H, m, overlapped H-14 and H-20), 2.07 (1H, dd, J=11.1, 11.1 Hz, H-21), 1.92 (2H, overlapped, H-6 and H-16), 1.79 (1H, ddd, J=13.9, 13.9, 4.6 Hz, H-6), 1.46 (1H, m, H-15), 1.35 (1H, m, H-16), 1.24 (1H, ddd, J=11.4, 11.4, 11.4 Hz, H-14). $^{13}$C-NMR (100 MHz, CDCl$_3$) δ ppm: 146.7 (C-13), 139.5 (C-19), 130.7 (C-8), 128.7 (C-11), 122.1 (C-9), 120.0 (C-10), 116.9 (C-18), 111.8 (C-12), 91.0 (C-2), 80.3 (C-7), 61.9 (C-1'), 61.7 (C-21), 61.3 (C-2'), 60.4 (C-17), 58.9 (C-3), 50.0 (C-5), 46.8 (C-20), 37.3 (C-6), 36.8 (C-16), 36.7 (C-15), 30.1 (C-14). $[α]_D^{24}$ −81 (c 1.0, CHCl$_3$). EI-MS m/z (%): 356 (100, M$^+$), 166 (76), 154 (37). HR-FAB-MS (NBA/PEG): calcd. for $C_{21}H_{29}N_2O_3$: 357.2178, found: 357.2169.

Preparation of Compound 9

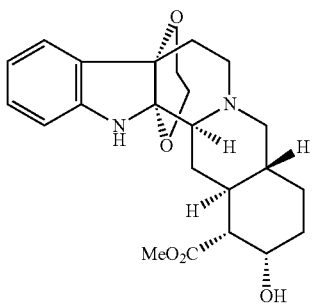

To a stirred solution of yohimbine (117.4 mg, 0.33 mmol) in dry MeCN (1.7 mL) and dry ethylene glycol (1.7 mL) were successively added NH$_4$Cl (69.8 mg, 1.29 mmol) and PIFA (157.0 mg, 0.36 mmol) at room temperature and the mixture was stirred for 3 h at 40° C. under argon atmosphere. After adding chilled aqueous NaHCO$_3$ solution, the mixture was extracted three times with chloroform. The combined extract was washed with brine, dried over MgSO$_4$, and evaporated. The crude product was chromatographed on silica gel (10% MeOH in CHCl$_3$) to give 113.2 mg (83%) of 9 as a pale yellowish amorphous powder, a portion of which was recrystallized from acetone and n-hexane to give colorless prisms (mp. 231-234° C., cap.). Compound 9; UV (MeOH) $λ_{max}$ nm: 292, 265, 239, 222, 205. IR (KBr) $ν_{max}$ cm$^{-1}$: 3381, 2924, 1726, 1616, 1468. $^1$H-NMR (500 MHz, CDCl$_3$) δ ppm: 7.17 (1H, d, J=6.8 Hz, H-9), 7.13 (1H, ddd, J=7.6, 7.6, 1.3 Hz, H-11), 6.87 (1H, dd, J=7.3, 7.3 Hz, H-10), 6.72 (1H, d, J=7.8 Hz, H-12), 4.19 (1H, br. s, $N_a$—H), 4.18 (1H, m, H-17), 3.87 (2H, overlapped, H-1' and H-2'), 3.76 (3H, s, 22-OCH$_3$), 3.60 (1H, d, J=9.3 Hz, H-1'), 3.42 (1H, d, J=9.5 Hz, H-2'), 3.27 (1H, br. s, 17-OH), 2.88 (1H, dd, J=11.1, 3.1 Hz, H-21), 2.61 (1H, d, J=11.5 Hz, H-3), 2.57 (1H, m, H-5), 2.42 (1H, ddd, J=12.3, 12.3, 2.4 Hz, H-5), 2.31 (1H, dd, J=11.1, 1.8 Hz, H-16), 2.02 (1H, dd, J=10.9, 10.9 Hz, H-21), 1.99 (1H, m, H-18), 1.90 (3H, overlapped, H-6, H-14 and H-15), 1.77 (1H, ddd, J=13.8, 13.8, 4.4 Hz, H-6), 1.50 (3H, overlapped, H-18, H-19 and 11-20), 1.39 (1H, m, H-19), 1.24 (1H, ddd, J=12.1, 12.1, 12.1 Hz, H-14). $^{13}$C-NMR (100 MHz, CDCl$_3$) δ ppm: 176.1 (C-22), 146.6 (C-13), 130.7 (C-8), 128.7 (C-11), 122.1 (C-9), 120.1 (C-10), 111.8 (C-12), 90.9 (C-2), 80.2 (C-7), 66.6 (C-17), 61.9 (C-1'), 61.8 (C-21), 61.3 (C-2'), 59.2 (C-3), 52.3 (C-16), 51.9 (22-OCH$_3$), 50.1 (C-5), 40.3 (C-20), 37.4 (C-6), 36.8 (C-15), 31.1 (C-18), 29.3 (C-14), 23.2 (C-19). $[α]_D^{25}$ −44 (c 0.98, CHCl$_3$). FAB-MS (NBA) m/z: 415 [M+H]$^+$. HR-FAB-MS (NBA/PEG): calcd. for $C_{23}H_{31}N_2O_5$: 415.2233, found: 415.2202.

Preparation of Compound 10

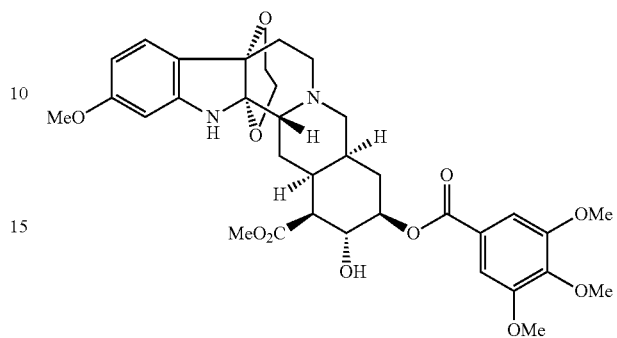

To a stirred solution of reserpine (100.7 mg, 0.17 mmol) in dry MeCN (2.0 mL) and dry ethylene glycol (2.0 mL) was added IBDA (111.2 mg, 0.31 mmol) at 0° C. After 2 h, another portion of IBDA (26.0 mg, 0.07 mmol) was added to the reaction mixture, and this was stirred for 1 h at 0° C. under argon atmosphere. After adding chilled aqueous NaHCO$_3$ solution, the mixture was extracted three times with chloroform. The combined extract was washed with brine, dried over MgSO$_4$, and evaporated. The crude product was chromatographed on silica gel (ethyl acetate/chloroform=30:70) to give 102.3 mg (93%) of 10 as a yellowish oil, a portion of which was recrystallized from ethyl acetate to give colorless prisms (mp. 130-132° C., cap.). Compound 10; UV (MeOH) $λ_{max}$ nm: 267, 246, 267. IR (ATR) $ν_{max}$ cm$^{-1}$: 3355, 2934, 1739, 1717, 1626. $^1$H-NMR (500 MHz, CDCl$_3$) δ ppm: 7.32 (2H, s, H-24 and H-28), 7.05 (1H, d, J=8.1 Hz, H-9), 6.43 (1H, dd, J=8.1, 2.2 Hz, H-10), 6.35 (1H, d, J=2.2 Hz, H-12), 5.06 (1H, m, H-18), 3.92 (9H, overlapped, 25-OCH$_3$, 26-OCH$_3$ and 27-OCH$_3$), 3.90 (1H, s,), 3.88 (1H, dd, J=11.7, 1.7 Hz, H17), 3.83 (1H, m, H-2'), 3.81 (3H, s, 16-CO$_2$CH$_3$), 3.78 (3H, s, 11-OCH$_3$), 3.76 (1H, m, H-1'), 3.60 (1H, m, H-1'), 3.58 (1H, m, H-21), 3.54 (3H, s, 17-OCH$_3$), 3.54 (1H, dd, J=9.0, 1.5 Hz), 3.49 (1H, d, J=7.3 Hz), 3.43 (1H, dd, J=11.7, 1.7 Hz, H-2'), 3.10 (1H, ddd, J=13.6, 13.6, 2.2 Hz, H-5), 2.79 (1H, dd, J=11.0, 5.1 Hz, H-16), 2.67 (1H, m, H-15), 2.59 (1H, m, H-5), 2.16 (3H, overlapped, H-19, H-20 and H-21), 2.00 (1H, m, H-14), 1.95 (1H, m, H-19), 1.87 (1H, ddd, J=13.4, 13.4, 4.2 Hz, H-6), 1.80 (1H, dd, J=14.7, 4.5 Hz, H-14), 1.69 (1H, m, H-6). $^{13}$C-NMR (100 MHz, CDCl$_3$) δ ppm: 172.6 (16-CO$_2$CH$_3$), 165.4 (C-22), 160.9 (C-11), 152.9 (C-25, C-27), 148.4 (C-13), 142.3 (C-26), 125.4 (C-23), 122.9 (C-9), 122.6 (C-8), 106.8 (C-24, C-28), 105.7 (C-10), 98.3 (C-12), 89.2 (C-2), 80.9 (C-7), 77.9 (C-18), 77.8 (C-17), 61.5 (C-2'), 61.4 (C-1'), 60.9 (26-OCH$_3$), 60.8 (17-OCH$_3$), 56.2 (25-OCH$_3$, 27-OCH$_3$), 55.4 (11-OCH$_3$), 52.0 (16-CO$_2$CH$_3$), 51.9 (C-16), 51.3 (C-21), 51.0 (C-3), 48.7 (C-5), 34.0 (C-6), 33.9 (C-20), 32.6 (C-15), 30.1 (C-19), 20.1 (C-14). $[α]_D^{24}$ −45 (c 0.99, CHCl$_3$). FAB-MS (NBA) m/z: 669 [M+H]$^+$. HR-FAB-MS (NBA/PEG): calcd. for $C_{35}H_{45}N_2O_{11}$: 669.3023, found: 669.3008.

Fluorination of Compound 3

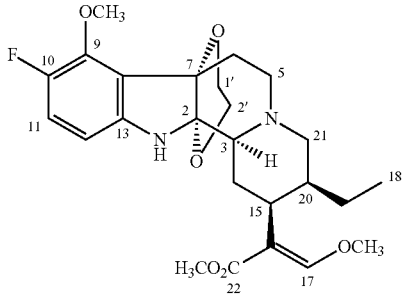

To a solution of 3 (20.6 mg, 0.045 mmol) in dry DCM (0.4 mL) were added FP-T800 (17.0 mg, 0.054 mmol) and MeNO$_2$ (47 μL) at 0° C. and the mixture was stirred at the same temperature under argon atmosphere. After 24 h, FP-T800 (4.8 mg, 0.015 mmol) was added to the reaction mixture, which was further stirred for 46.5 h at 0° C. The reaction mixture was poured into cold saturated aqueous NaHCO$_3$ solution, and this was extracted three times with chloroform. The combined extract was washed with brine, dried over MgSO$_4$, and concentrated to give a residue that was purified by pre-packed amino-silica gel column chromatography (ethyl acetate/n-hexane=20:80) to give 11.3 mg (53%) of 11 as a colorless amorphous powder, together with 2.2 mg (11%) of recovered starting material. Compound 11; UV (MeOH) $\lambda_{max}$ (log ε) nm: 295 (3.36), 277 (3.20), 239 (4.13), 225 (4.06), 207 (4.44). IR (ATR) $\nu_{max}$ cm$^{-1}$: 2926, 1697, 1647, 1489, 1242. $^1$H-NMR (500 MHz, CDCl$_3$) δ ppm: 7.42 (1H, s, H-17), 6.84 (1H, dd, J=12.5, 8.5 Hz, H-11), 6.32 (1H, dd, J=8.4, 3.3 Hz, H-12), 4.16 (1H, br. s, N$_a$—H), 4.00 (3H, d, J=2.4 Hz, 9-OCH$_3$), 3.91 (2H, m, H-1', H-2'), 3.79 (3H, s, 17-OCH$_3$), 3.71 (1H, m, H-1', overlapped with 22-OCH$_3$), 3.70 (3H, s, 22-OCH$_3$), 3.44 (1H, d, J=9.5 Hz, H-2'), 3.00 (1H, d, J=11.6 Hz, H-21), 2.91 (1H, ddd, J=13.1, 3.6, 3.6 Hz, H-15), 2.50 (1H, ddd, J=11.3, 3.3, 3.3 Hz, H-5), 2.45 (1H, d, J=11.0 Hz, H-3), 2.34 (2H, m, H-5 and H-14), 2.26 (1H, dd, J=11.6, 3.1 Hz, H-21), 2.13 (1H, d, J=14.3 Hz, H-6), 1.86 (1H, ddd, J=13.6, 13.6, 4.2 Hz, H-6), 1.77 (1H, d, J=12.5 Hz, H-14), 1.72 (1H, m, H-19), 1.57 (1H, br. d, J=11.3 Hz, H-20), 1.24 (1H, m, H-19), 0.84 (3H, dd, J=7.5, 7.5 Hz, H$_3$-18). $^{13}$C-NMR (125 MHz, CDCl$_3$) δ ppm: 169.0 (C-22), 160.4 (C-17), 149.5 (d, J=237.8 Hz, C-10), 144.6 (d, J=12.4 Hz, C-9), 144.1 (C-13), 121.9 (C-8), 116.7 (d, J=21.5 Hz, C-11), 111.5 (C-16), 106.0 (d, J=7.3 Hz, C-12), 91.5 (C-2), 81.5 (C-7), 62.5 (C-1'), 61.6 (17-OCH$_3$), 61.2 (C-2'), 61.1 (d, J=6.9 Hz, 9-OCH$_3$), 60.8 (C-3), 58.4 (C-21), 51.3 (22-OCH$_3$), 50.2 (C-5), 40.4 (C-20), 40.0 (C-15), 36.0 (C-6), 24.0 (C-14), 19.1 (C-19), 13.0 (C-18). $^{19}$F-NMR (564.7 MHz, CDCl$_3$) δ ppm: −141.5 (d, J=12.9 Hz). CD (c=0.27 mM, MeOH, 24° C.), Δε (λ nm): 0 (319), −0.9 (293), 0 (268), +0.9 (253), 0 (245), −19.0 (208), −14.6 (200). FAB-MS (NBA) m/z: 477 [M+H]$^+$. HR-FAB-MS (NBA/PEG): calcd. for C$_{25}$H$_{34}$N$_2$O$_6$F: 477.2401. found: 477.2381. FIG. 8a is the 1H-NMR for Compound 11 and FIG. 8b is the 13C-NMR for Compound 11.

Chlorination of Compound 3

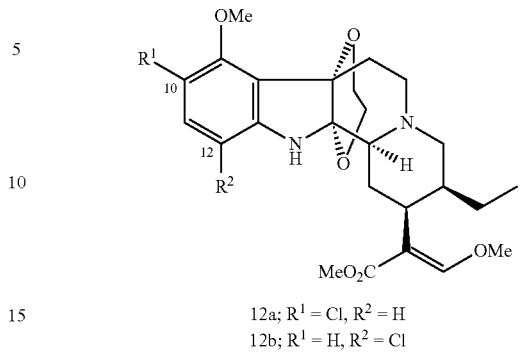

12a; R$^1$ = Cl, R$^2$ = H
12b; R$^1$ = H, R$^2$ = Cl

To a solution of 3 (106 mg, 0.23 mmol) in dry AcOH (2.0 mL) was added N-chlorosuccinimide (38.7 mg, 0.58 mmol) and the mixture was stirred for 12 h at room temperature under argon atmosphere. After adding Na$_2$S$_2$O$_3$, the mixture was poured into cold aqueous NH$_4$OH solution, and this was extracted three times with chloroform. The combined extract was washed with brine, dried over MgSO$_4$, and evaporated. The crude product was chromatographed on amino-silica gel (ethyl acetate/n-hexane=10:90) to give 100.7 mg (88%) of 12a and 13.2 mg (11%) of 12b, as a colorless amorphous powder, respectively. Compound 12a; UV (MeOH) $\lambda_{max}$ nm (log ε): 299 (3.12), 279 (2.92), 246 (4.18), 227 (3.96), 210 (4.40). IR (ATR) $\nu_{max}$ cm$^{-1}$: 2942, 1701, 1604, 1456, 1285. $^1$H-NMR (400 MHz, CDCl$_3$) δ ppm: 7.42 (1H, s, H-17), 7.12 (1H, d, J=8.2 Hz, H-11), 6.43 (1H, d, J=8.2 Hz, H-12), 4.30 (1H, br. s, N$_a$—H), 3.95 (1H, m, H-2'), 3.95 (3H, s, 9-OCH$_3$), 3.90 (1H, m, H-1'), 3.79 (3H, s, 17-OCH$_3$), 3.70 (3H, s, 22-OCH$_3$), 3.70 (1H, m, H-1'), 3.43 (1H, d, J=9.2 Hz, H-2'), 3.00 (1H, dd, J=11.6, 2.1 Hz, H-21), 2.92 (1H, ddd, J=13.2, 3.6, 3.6 Hz, H-15), 2.51 (1H, m, H-5), 2.45 (1H, dd, J=11.3, 1.6 Hz, H-3), 2.34 (2H, m, H-5 and H-14), 2.26 (1H, dd, J=11.2, 3.2 Hz, H-21), 2.15 (1H, ddd, J=14.3, 2.5, 2.5 Hz, H-6), 1.88 (1H, ddd, J=13.8, 13.8, 4.6 Hz, H-6), 1.78 (1H, br. d, J=11.2 Hz, H-14), 1.72 (1H, m, H-19), 1.58 (1H, br. d, J=11.2 Hz, H-20), 1.24 (1H, m, H-19), 0.85 (3H, dd, J=7.4, 7.4 Hz, H$_3$-18). $^{13}$C-NMR (100 MHz, CDCl$_3$) δ ppm: 169.0 (C-22), 160.4 (C-17), 152.9 (C-9), 147.9 (C-13), 130.6 (C-11), 123.3 (C-8), 118.0 (C-10), 111.6 (C-16), 108.3 (C-12), 91.2 (C-2), 81.5 (C-7), 62.7 (C-1'), 61.7 (17-OCH$_3$), 61.3 (9-OCH$_3$), 61.1 (C-2'), 60.8 (C-3), 58.5 (C-21), 51.3 (22-OCH$_3$), 50.2 (C-5), 40.4 (C-20), 40.0 (C-15), 36.4 (C-6), 24.0 (C-14), 19.1 (C-19), 13.0 (C-18). CD (c=0.25 mM, MeOH, 24° C.), Δε (λ nm): 0 (318), −1.0 (292), 0 (267), +0.3 (259), 0 (251), −0.9 (240), −0.8 (236), −24.8 (209), −11.4 (200). EI-MS (%) m/z: 494 (M$^+$+2, 30), 492 (M$^+$, 83), 239 (100). HR-FAB-MS (NBA/PEG): calcd. for C$_{25}$H$_{34}$N$_2$O$_6$$^{35}$Cl: 493.2105. found: 493.2104, calcd. for C$_{25}$H$_{34}$N$_2$O$_6$$^{37}$Cl: 495.2089. found: 495.2061. Compound 12b; UV (MeOH) $\lambda_{max}$ nm (log ε): 293 (3.24), 276 (3.01), 237 (4.13), 231 (4.11), 215 (4.52). IR (ATR) $\nu_{max}$ cm$^{-1}$: 2940, 1698, 1608, 1486, 1279, 1238. $^1$H-NMR (400 MHz, CDCl$_3$) δ ppm: 7.43 (1H, s, H-17), 7.07 (1H, dd, J=8.8, 0.5 Hz, H-11), 6.35 (1H, d, J=8.6 Hz, H-10), 4.45 (1H, br. s, N$_a$—H), 3.93 (1H, ddd, J=11.7, 11.7, 2.9 Hz, H-2'), 3.83 (3H, s, 9-OCH$_3$), 3.79 (3H, s, 17-OCH$_3$), 3.78 (1H, m, H-1', overlapped with 17-OCH$_3$), 3.71 (3H, s, 22-OCH$_3$), 3.69 (1H, m, H-1', overlapped with 22-OCH$_3$), 3.43 (1H, dd, J=11.6, 2.5 Hz, H-2'), 3.00 (1H, d, J=11.5 Hz, H-21), 2.93 (1H, ddd, J=13.0, 3.5, 3.5 Hz, H-15), 2.48 (2H, m, H-3 and H-5), 2.37 (2H, m, H-5 and H-14), 2.26 (1H, dd, J=11.4, 3.3 Hz, H-21), 2.15 (1H, ddd, J=14.5, 2.1, 2.1 Hz, H-6), 1.82 (2H, m, H-6 and H-14), 1.75 (1H, m, H-19), 1.26 (1H, m, H-19), 0.85 (3H, dd, J=7.3, 7.3 Hz, $H_3$-18), *H-20: under $H_2O$. $^{13}C$-NMR (125 MHz, $CDCl_3$) δ ppm: 169.2 (C-22), 160.5 (C-17), 155.6 (C-9), 145.6 (C-13), 129.2 (C-11), 117.3 (C-8), 111.6 (C-16), 109.7 (C-12), 103.9 (C-10), 90.6 (C-2), 82.0 (C-7), 62.5 (C-1'), 61.6 (17-$OCH_3$), 61.1 (C-2'), 60.8 (C-3), 58.5 (C-21), 55.6 (9-$OCH_3$), 51.3 (22-$OCH_3$), 50.1 (C-5), 40.4 (C-20), 40.2 (C-15), 35.3 (C-6), 24.1 (C-14), 19.1 (C-19), 13.1 (C-18). CD (c=0.42 mM, MeOH, 24° C.), Δε (λ nm): 0 (310), −0.8 (287), −0.1 (262), −0.8 (247), 0 (241), +0.2 (236), 0 (229), −19.1 (212), −6.7 (200). EI-MS m/z (%): 494 ($M^+$2, 25), 492 ($M^+$, 65), 239 (100). HR-FAB-MS (NBA/PEG): calcd. for $C_{25}H_{34}N_2O_6{}^{35}Cl$: 493.2105. found: 493.2107, calcd. for $C_{25}H_{34}N_2O_6{}^{37}Cl$: 495.2089. found: 495.2082.

Bromination of Compound 3

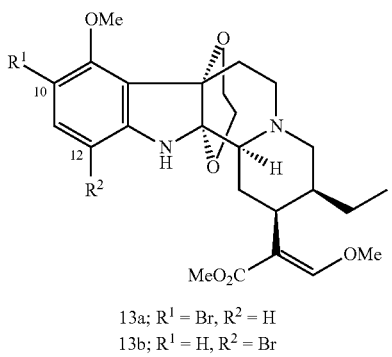

13a; $R^1$ = Br, $R^2$ = H
13b; $R^1$ = H, $R^2$ = Br

To a solution of 3 (101 mg, 0.22 mmol) in dry DMF (2.0 mL) was added a solution of N-bromosuccinimide (43.2 mg, 0.24 mmol) in dry DMF (1.0 mL) and the mixture was stirred for 5 h at room temperature under argon atmosphere. The reaction mixture was poured into saturated aqueous $NaHCO_3$ solution, and this was extracted three times with chloroform. The combined extract was washed with brine, dried over $MgSO_4$, and concentrated to give a residue that was purified by pre-packed amino-silica gel column chromatography (ethyl acetate/n-hexane=10:90) to give 90 mg (75%) of 13a and 29 mg (24%) of 13b, as a colorless amorphous powder, respectively. Compound 13a; UV (MeOH) $λ_{max}$ nm (log ε): 298 (3.19), 281 (3.09), 245 (4.24), 228 (4.04), 211 (4.42). IR (ATR) $ν_{max}$ $cm^{-1}$: 2941, 1699, 1628, 1602, 1456, 1283. $^1H$-NMR (500 MHz, $CDCl_3$) δ ppm: 7.41 (1H, s, H-17), 7.27 (1H, d, J=8.2 Hz, H-11), 6.38 (1H, d, J=8.2 Hz, H-12), 4.33 (1H, br. s, $N_a$—H), 3.93 (3H, s, 9-$OCH_3$), 3.88 (2H, m, H-1' and H-2'), 3.79 (3H, s, 17-$OCH_3$), 3.70 (3H, s, 22-$OCH_3$), 3.69 (1H, m, H-1'), 3.43 (1H, dd, J=11.6, 2.1 Hz, H-2'), 3.00 (1H, d, J=10.4 Hz, 14-21), 2.92 (1H, ddd, J=13.4, 3.6, 3.6 Hz, H-15), 2.51 (1H, br. d, J=11.0 Hz, H-5), 2.45 (1H, br. d, J=10.4 Hz, H-3), 2.34 (2H, m, H-5 and H-14), 2.26 (1H, d, J=12.2 Hz, H-21), 2.16 (1H, ddd, J=14.3, 2.4, 2.4 Hz, H-6), 1.89 (1H, ddd, J=13.7, 13.7, 4.0 Hz, H-6), 1.78 (1H, d, J=12.8 Hz, H-14), 1.72 (1H, m, H-19), 1.57 (1H, br. d, J=11.3 Hz, H-20), 1.25 (1H, m, H-19), 0.85 (3H, dd, J=7.3, 7.3 Hz, $H_3$-18). $^{13}C$-NMR (125 MHz, $CDCl_3$) δ ppm: 169.0 (C-22), 160.4 (C-17), 153.8 (C-9), 148.7 (C-13), 133.5 (C-11), 123.5 (C-8), 111.5 (C-16), 109.1 (C-12), 106.5 (C-10), 91.1 (C-2), 81.5 (C-7), 62.7 (C-1'), 61.6 (17-$OCH_3$), 61.5 (9-$OCH_3$), 61.1 (C-2'), 60.8 (C-3), 58.4 (C-21), 51.2 (22-$OCH_3$), 50.2 (C-5), 40.4 (C-20), 39.9 (C-15), 36.5 (C-6), 24.0 (C-14), 19.1 (C-19), 13.0 (C-18). CD (c=0.19 mM, MeOH, 24° C.), Δε (λ nm): 0 (319), −0.9 (299), 0 (268), +0.3 (259), 0 (254), −17.2 (210), −8.7 (200). FAB-MS (NBA) m/z: 539 $[M+2+H]^+$, 537 $[M+H]^+$. HR-FAB-MS (NBA/PEG): calcd. for $C_{25}H_{34}N_2O_6{}^{79}Br$: 537.1600. found: 537.1615, calcd. for $C_{25}H_{34}N_2O_6{}^{81}Br$: 539.1584, found: 539.1589. Compound 13b; UV (MeOH) $λ_{max}$ nm (log ε): 294 (3.27), 275 (3.02), 233 (4.16), 215 (4.54). IR (ATR) $ν_{max}$ $cm^{-1}$: 2953, 1699, 1607, 1484, 1278. $^1H$-NMR (400 MHz, $CDCl_3$) δ ppm: 7.42 (1H, s, H-17), 7.20 (1H, d, J=8.8 Hz, H-11), 6.32 (1H, d, J=8.8 Hz, H-10), 4.40 (1H, br. s, $N_a$—H), 3.92 (1H, ddd, J=11.6, 11.6, 3.1 Hz, H-2'), 3.83 (3H, s, 9-$OCH_3$), 3.79 (3H, s, 17-$OCH_3$), 3.79 (1H, m, H-1', overlapped with 17-$OCH_3$), 3.71 (3H, s, 22-$OCH_3$), 3.68 (1H, dd, J=11.5, 2.7 Hz, H-1'), 3.43 (1H, dd, J=11.6, 2.3 Hz, H-2'), 2.99 (1H, dd, J=11.6, 1.9 Hz, H-21), 2.92 (1H, ddd, J=12.9, 3.5, 3.5 Hz, H-15), 2.46 (2H, m, H-3 and H-5), 2.36 (2H, m, H-5 and H-14), 2.26 (1H, dd, J=11.7, 2.7 Hz, H-21), 2.15 (1H, ddd, J=14.1, 2.4, 2.4 Hz, H-6), 1.82 (2H, m, H-6 and H-14), 1.75 (1H, m, H-19), 1.57 (1H, br. d, J=10.8 Hz, H-20), 1.26 (1H, m, H-19), 0.85 (3H, dd, J=7.3, 7.3 Hz, $H_3$-18). $^{13}C$-NMR (125 MHz, $CDCl_3$) ppm: 169.2 (C-22), 160.5 (C-17), 156.2 (C-9), 147.0 (C-13), 132.0 (C-11), 117.3 (C-8), 111.6 (C-16), 104.5 (C-10), 97.4 (C-12), 90.4 (C-2), 82.2 (C-7), 62.4 (C-1'), 61.6 (17-$OCH_3$), 61.1 (C-2'), 60.7 (C-3), 58.4 (C-21), 55.6 (9-$OCH_3$), 51.3 (22-$OCH_3$), 50.1 (C-5), 40.4 (C-20), 40.2 (C-15), 35.3 (C-6), 24.1 (C-14), 19.1 (C-19), 13.1 (C-18). CD (c=0.18 mM, MeOH, 24° C.), Δε (λ nm): 0 (308), −0.9 (290), +0.1 (258), −0.7 (250), 0 (248), +0.4 (229), 0 (225), −22.0 (212), −6.9 (200). FAB-MS (NBA) m/z: 539 $[M+2+H]^+$, 537 $[M+H]^+$. HR-FAB-MS (NBA/PEG): calcd. for $C_{25}H_{34}N_2O_6{}^{79}Br$: 537.1600, found: 537.1640, calcd. for $C_{25}H_{34}N_2O_6{}^{81}Br$: 539.1584. found: 539.1642.

Nitration of Compound 3

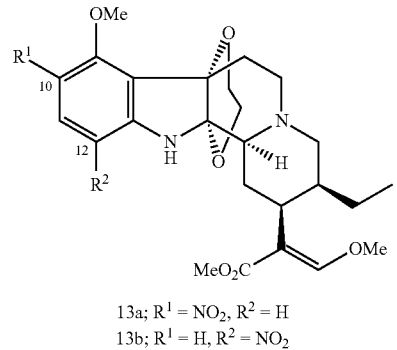

13a; $R^1$ = $NO_2$, $R^2$ = H
13b; $R^1$ = H, $R^2$ = $NO_2$

To a solution of 3 (20.5 mg, 0.045 mmol) in dry DCM (0.9 mL) were added cerium (IV) ammonium nitrate (24.4 mg, 0.045 mmol) and one drop of conc. $H_2SO_4$ and the mixture was stirred for 1 h at room temperature under argon atmosphere. The reaction mixture was poured into cold saturated aqueous $NaHCO_3$ solution, and this was extracted three times with chloroform. The combined extract was washed with brine, dried over $MgSO_4$, and evaporated to give a residue that was purified by pre-packed amino-silica gel column chromatography (ethyl acetate/n-hexane=30:70-50:50) to give 11.6 mg (52%) of 14a and 4.7 mg (21%) of 14b, as a pale yellowish amorphous powder, respectively. Compound 14a; UV (MeOH) $λ_{max}$ nm (log ε): 359 (3.87), 283 (3.29), 242 (4.09), 228 (4.04), 206 (4.28). IR (ATR) $ν_{max}$ $cm^{-1}$: 2949, 1698, 1599, 1517, 1326, 1241. $^1H$-NMR (400 MHz, $CDCl_3$) δ ppm: 7.93 (1H, d, J=8.6 Hz, H-11), 7.42 (1H, s, H-17), 6.47 (1H, d, J=8.6 Hz, H-12), 4.87 (1H, br. 5, $N_a$—H), 3.97 (3H, s, 9-OCH₃), 3.89 (2H, m, H-1' and H-2'), 3.81 (3H, s, 17-OCH₃), 3.73 (1H, m, H-1', overlapped with 22-OCH₃), 3.71 (3H, s, 22-OCH₃), 3.46 (1H, d, J=9.7 Hz, H-2'), 3.00 (1H, dd, J=11.7, 1.8 Hz, H-21), 2.93 (1H, ddd, J=13.2, 3.7, 3.7 Hz, H-15), 2.52 (1H, d, J=10.4 Hz, H-5), 2.47 (1H, d, J=9.3 Hz, H-3), 2.31 (3H, m, H-5, H-14 and H-21), 2.21 (1H, d, J=14.3 Hz, H-6), 1.86 (1H, ddd, J=13.3, 13.3, 4.5 Hz, H-6), 1.80 (1H, d, J=12.6 Hz, H-14), 1.70 (1H, m, H-19), 1.59 (1H, br. d, J=11.7 Hz, H-20), 1.26 (1H, m, H-19), 0.86 (3H, dd, J=7.3, 7.3 Hz, H₃-18). ¹³C-NMR (125 MHz, CDCl₃) δ ppm: 168.9 (C-22), 160.4 (C-17), 154.2 (C-13), 153.0 (C-9), 135.6 (C-10), 129.3 (C-11), 123.1 (C-8), 111.5 (C-16), 106.3 (C-12), 91.0 (C-2), 81.0 (C-7), 62.8 (9-OCH₃), 62.6 (C-1'), 61.7 (17-OCH₃), 61.0 (C-2'), 60.6 (C-3), 58.4 (C-21), 51.3 (22-OCH₃), 50.0 (C-5), 40.3 (C-20), 39.8 (C-15), 36.2 (C-6), 24.0 (C-14), 19.1 (C-19), 13.0 (C-18). CD (c=0.26 mM, MeOH, 24° C.), Δε (λ nm): 0 (436), +1.4 (379), 0 (344), −1.0 (304), 0 (286), +0.2 (282), 0 (278), −1.9 (263), 0 (249), +0.6 (242), 0 (237), −11.3 (208), −10.5 (200). FAB-MS (NBA) m/z: 504 [M+H]⁺. HR-FAB-MS (NBA/PEG): calcd. for C₂₅H₃₄N₃O₈: 504.2346, found: 504.2318. Compound 14b; UV (MeOH) λ_max nm (log ε): 356 (3.66), 314 (3.84), 274 (3.38), 241 (4.23), 221 (4.02), 205 (4.37). IR (ATR) ν_max cm⁻¹: 2944, 1699, 1625, 1596, 1476, 1324, 1274, 1252. ¹H-NMR (400 MHz, CDCl₃) ppm: 8.00 (1H, d, J=9.3 Hz, H-11), 7.46 (1H, s, H-17), 6.87 (1H, br. s, N_a—H), 6.46 (1H, d, J=9.5 Hz, H-10), 3.95 (3H, s, 9-OCH₃), 3.91 (1H, m, H-2', overlapped with 9-OCH₃), 3.82 (3H, s, 17-OCH₃), 3.73 (2H, m, H₂-1', overlapped with 22-OCH₃), 3.72 (3H, s, 22-OCH₃), 3.46 (1H, d, J=11.0 Hz, H-2'), 2.99 (1H, dd, J=11.5, 1.8 Hz, H-21), 2.94 (1H, m, H-15), 2.47 (4H, m, H-3, H₂-5 and H-14), 2.28 (1H, dd, J=11.5, 2.9 Hz, H-21), 2.18 (1H, ddd, J=14.3, 2.3, 2.3 Hz, H-6), 1.88 (1H, m, H-14), 1.79 (1H, ddd, J=13.7, 13.7, 4.5 Hz, H-6), 1.72 (1H, m, H-19), 1.59 (1H, br. d, J=12.8 Hz, H-20), 1.26 (1H, m, H-19), 0.85 (3H, dd, J=7.3, 7.3 Hz, H₃-18). ¹³C-NMR (125 MHz, CDCl₃) δ ppm: 169.2 (C-22), 161.3 (C-9), 160.7 (C-17), 146.8 (C-13), 127.3 (C-12), 126.9 (C-11), 117.3 (C-8), 111.1 (C-16), 103.5 (C-10), 90.0 (C-2), 80.7 (C-7), 62.6 (C-1'), 61.6 (17-OCH₃), 61.0 (C-2'), 60.4 (C-3), 58.2 (C-21), 56.1 (9-OCH₃), 51.3 (22-OCH₃), 49.8 (C-5), 40.2 (C-20), 40.2 (C-15), 35.3 (C-6), 24.4 (C-14), 19.0 (C-19), 12.9 (C-18). CD (c=0.24 mM, MeOH, 24° C.), Δε (λ nm): 0 (437), +1.4 (392), 0 (363), −2.1 (333), 0 (309), +1.8 (288), 0 (259), −8.0 (235), −4.2 (215), −7.4 (203), −7.1 (200). FAB-MS (NBA) m/z: 504 [M+H]⁺. HR-FAB-MS (NBA/PEG): calcd. for C₂₅H₃₄N₃O₈: 504.2346, found: 504.2338.

Introduction of a Methoxyl Group on C-10 in Compound 3

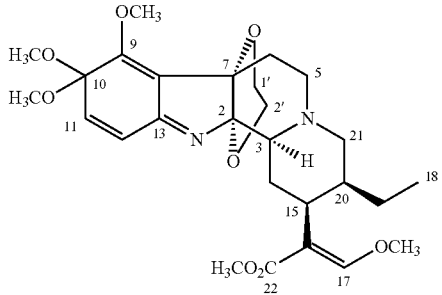

To a solution of 3 (50.8 mg, 0.11 mmol) in dry MeOH (2.0 mL) and dry DCM (0.5 mL) was added iodosobenzene diacetate (73.2 mg, 0.22 mmol) and the mixture was stirred for 30 min at 0° C. under argon atmosphere. The reaction mixture was poured into saturated aqueous NaHCO₃ solution, and this was extracted three times with chloroform. The combined extract was washed with brine, dried over MgSO₄, and evaporated to give a residue that was purified by pre-packed silica gel column chromatography (2% MeOH in CHCl₃) to give 39.4 mg (69%) of an intermediate: UV (MeOH) λ_max nm: 296, 239, 220. ¹H-NMR (500 MHz, CDCl₃) δ ppm: 7.43 (1H, s, H-17), 6.85 (1H, d, J=10.1 Hz, H-12), 6.16 (1H, d, J=10.1 Hz, H-11), 4.08 (3H, s, 9-OCH₃), 3.92 (1H, m, H-2'), 3.77 (3H, s, 17-OCH₃), 3.73 (2H, m, H₂-1'), 3.69 (3H, s, 22-OCH₃), 3.52 (1H, ddd, J=11.9, 2.3, 2.3 Hz, H-2'), 3.26 (3H, s, 10-OCH₃), 3.24 (3H, s, 10-OCH₃), 2.95 (1H, dd, J=11.6, 1.8 Hz, H-21), 2.89 (1H, ddd, J=13.7, 3.1, 3.1 Hz, H-15), 2.84 (1H, m, H-14), 2.54 (1H, dd, J=10.7, 2.7 Hz, H-3), 2.48 (1H, ddd, J=11.3, 4.0, 4.0 Hz, H-5), 2.28 (1H, ddd, J=11.7, 11.7, 2.8 Hz, H-5), 2.20 (1H, dd, J=11.3, 3.1 Hz, H-21), 2.14 (1H, ddd, J=14.3, 3.1, 3.1 Hz, H-6), 1.89 (1H, br. d, J=13.4 Hz, H-14), 1.80 (1H, ddd, J=14.2, 11.5, 4.6 Hz, H-6), 1.66 (1H, m, H-19), 1.53 (1H, br. d, J=11.3 Hz, H-20), 1.24 (1H, m, H-19), 0.81 (3H, dd, J=7.5, 7.5 Hz, H₃-18). ¹³C-NMR (125 MHz, CDCl₃) δ ppm: 169.7, 169.4 (C-13 and C-22), 160.6 (C-17), 150.9 (C-9), 138.5 (C-11), 128.7 (C-12), 123.3 (C-8), 111.5 (C-16), 99.1 (C-10), 95.3 (C-2), 79.4 (C-7), 63.2 (C-3), 62.5 (C-1'), 61.7 (17-OCH₃), 60.8 (C-2'), 59.4 (9-OCH₃), 58.9 (C-21), 51.4 (10-OCH₃×2), 51.2 (22-OCH₃), 51.0 (C-5), 40.5 (C-20), 40.1 (C-15), 35.5 (C-6), 24.7 (C-14), 19.1 (C-19), 13.0 (C-18). FAB-MS (NBA) m/z: 519 [M+H]⁺.

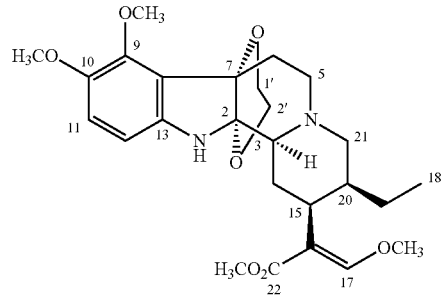

To a solution of the intermeidate in dry MeOH (3.0 mL) was added activated Zn (445 mg) and the mixture was stirred for 85 h at reflux temperature under argon atmosphere. The reaction mixture was filtered through Celite. The filtrate was concentrated under reduced pressure and poured into saturated aq. NaHCO₃ solution, and this was extracted three times with chloroform. The combined extract was washed with brine, dried over MgSO₄, and evaporated. The crude product was chromatographed on amino-silica gel (ethyl acetate) to give 34.5 mg (64% in two steps) of 15 as an amorphous powder. Compound 15; UV (MeOH) λ_max nm (log ε): 305 (3.02), 281 (2.90), 241 (3.83), 226 (3.72), 207 (4.01). IR (KBr) ν_max cm⁻¹: 3327, 2948, 1703, 1627, 1487, 1261. ¹H-NMR (600 MHz, CDCl₃) δ ppm: 7.41 (1H, s, H-17), 6.70 (1H, d, J=8.2 Hz, H-11), 6.39 (1H, d, J=8.2 Hz, H-12), 4.06 (1H, br. s, N_a—H), 3.93 (3H, s, 9-OCH₃), 3.92 (2H, m, H-1' and H-2', overlapped with 9-OCH₃), 3.80 (3H, s, 10-OCH₃), 3.79 (3H, s, 17-OCH₃), 3.70 (3H, s, 22-OCH₃), 3.69 (1H, m, H-1', overlapped with 22-OCH₃), 3.43 (1H, d, J=9.3 Hz, H-2'), 2.99 (1H, d, J=10.7 Hz, H-21), 2.91 (1H, d, J=13.2 Hz, H-15), 2.49 (1H, d, J=11.5 Hz, H-5), 2.45 (1H, d, J=11.0 Hz, H-3), 2.34 (2H, m, H-5 and H-14), 2.25 (1H, d, J=12.0 Hz, H-21), 2.14 (1H, d, J=14.4 Hz, H-6), 1.89 (1H, ddd, J=13.8, 13.8, 4.5 Hz, H-6), 1.77 (1H, d, J=11.3 Hz, H-14), 1.76 (1H, m, H-19), 1.57 (1H, br.d, J=11.3 Hz, H-20), 1.24 (1H, m, H-19), 0.84 (3H, dd, J=7.4, 7.4 Hz, H$_3$-18). $^{13}$C-NMR (150 MHz, CDCl$_3$) δ ppm: 169.2 (C-22), 160.4 (C-17), 146.8 (C-9 and C-10), 142.1 (C-13), 122.7 (C-8), 113.7 (C-11), 111.8 (C-16), 106.5 (C-12), 91.4 (C-2), 81.7 (C-7), 62.6 (C-1'), 61.7 (17-OCH$_3$), 61.3 (C-2'), 61.0 (C-3 and 9-OCH$_3$), 58.7 (C-21), 56.7 (10-OCH$_3$), 51.4 (22-OCH$_3$), 50.4 (C-5), 40.5 (C-20), 40.2 (C-15), 36.3 (C-6), 24.1 (C-14), 19.2 (C-19), 13.1 (C-18). CD (c=0.21 mM, MeOH, 24° C.), Δε (λ nm): 0 (348), +0.5 (316), 0 (302), −0.7 (287), 0 (279), +3.4 (256), 0 (245), −14.0 (208), −6.1 (200). FAB-MS (NBA) m/z: 489 [M+H]$^+$. HR-FAB-MS (NBA/PEG): calcd. for C$_{26}$H$_{37}$N$_2$O$_7$: 489.2601, found: 489.2555.

Preparation of 10-Fluoromitragynine (17)

To a stirred solution of 11 (168 mg, 0.35 mmol) in dry AcOH (3.5 mL) was added

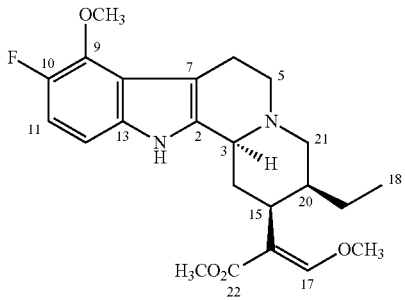

Figure 9A:
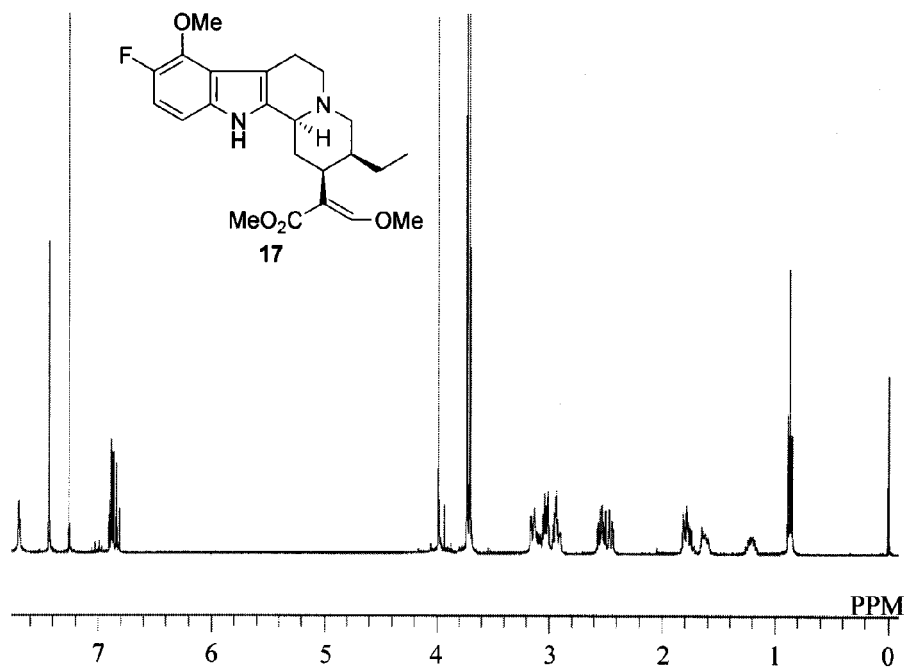
FIG. 9a is the 1H-NMR for Compound 17 and FIG. 9b is the 13C-NMR for Compound 17.
Figure 9B:
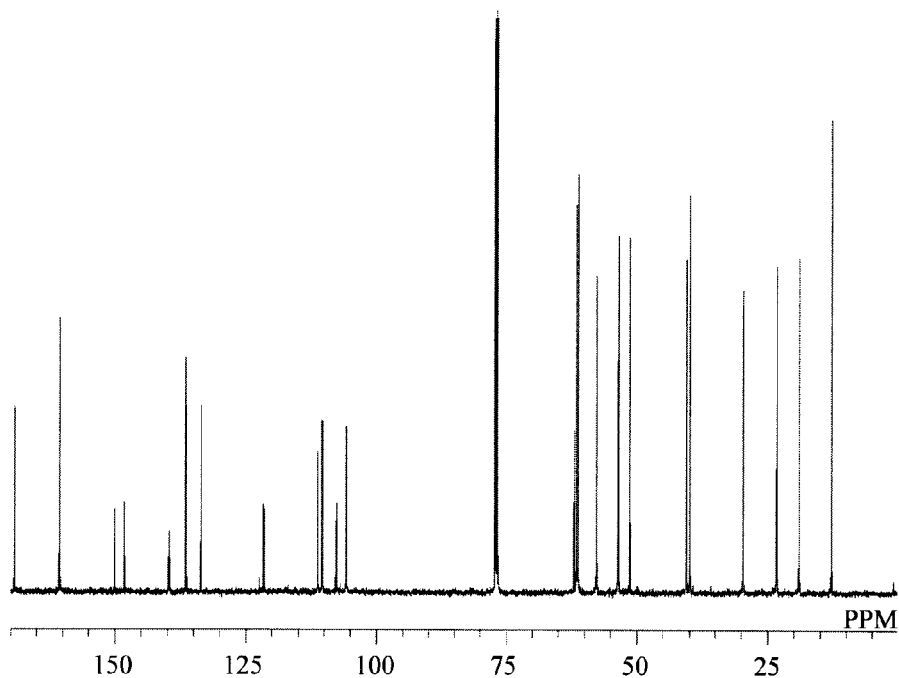

NaCNBH$_3$ (46.7 mg, 0.71 mmol) at room temperature. After 15 min, another portion of NaCNBH$_3$ (46.7 mg, 0.71 mmol) was added to the reaction mixture, and this was stirred for 1 h at room temperature under argon atmosphere. MeOH (45 μL) was added to the reaction mixture, which was then heated under reflux at 70° C. for 7 h. The reaction mixture was poured into cold aqueous NH$_4$OH solution, and this was extracted four times with chloroform. The combined extract was washed with brine, dried over MgSO$_4$, and evaporated to give a residue that was purified by pre-packed amino-silica gel column chromatography (ethyl acetate/n-hexane=30:70-50:50) to give 131.3 mg (89%) of 17 as a colorless amorphous powder. Compound 17; UV (MeOH) λ$_{max}$ nm (log ε): 275 (3.73), 227 (4.33), 209 (4.16). IR (KBr) ν$_{max}$ cm$^{-1}$: 2952, 1700, 1646, 1508, 1439, 1241. $^1$H-NMR (500 MHz, CDCl$_3$) δ ppm: 7.74 (1H, br. s, N$_a$—H), 7.44 (1H, s, H-17), 6.89 (1H, dd, J=8.5, 3.7 Hz, H-12), 6.84 (1H, dd, J=11.6, 8.5 Hz, H-11), 3.99 (3H, d, J=1.2 Hz, 9-OCH$_3$), 3.73 (3H, s, 17-OCH$_3$), 3.71 (3H, s, 22-OCH$_3$), 3.15 (1H, d, J=9.8 Hz, H-3), 3.10 (1H, m, H-6), 3.03 (2H, m, H-15 and H-21), 2.93 (2H, m, H-5 and H-6), 2.56 (1H, dd, J=11.5, 4.5 Hz, H-5), 2.51 (1H, m, H-14), 2.45 (1H, dd, J=11.6, 2.4 Hz, H-21), 1.79 (1H, m, H-14), 1.76 (1H, m, H-19), 1.63 (1H, br. d, J=11.0 Hz, H-20), 1.21 (1H, m, H-19), 0.87 (3H, dd, J=7.3, 7.3 Hz, H$_3$-18). $^{13}$C-NMR (125 MHz, CDCl$_3$) δ ppm: 169.2 (C-22), 160.6 (C-17), 149.1 (d, J=233.7 Hz, C-10), 139.7 (d, J=12.4 Hz, C-9), 136.5 (C-2), 133.6 (C-13), 121.7 (C-8), 111.2 (C-16), 110.4 (d, J=23.8 Hz, C-11), 107.6 (d, J=5.0 Hz, C-7), 105.9 (d, J=8.2 Hz, C-12), 62.0 (d, J=4.6 Hz, 9-OCH$_3$), 61.5 (17-OCH$_3$), 61.3 (C-3), 57.7 (C-21), 53.6 (C-5), 51.3 (22-OCH$_3$), 40.5 (C-20), 39.7 (C-15), 29.7 (C-14), 23.3 (C-6), 19.0 (C-19), 12.8 (C-18). CD (c=0.28 mM, MeOH, 24° C.), Δε (λ nm): 0 (324), +0.8 (300), +0.6 (294), +1.2 (274), 0 (259), −5.7 (240), −0.6 (229), −5.6 (215), +0.2 (200). FAB-MS (NBA) m/z: 417 [M+H]$^+$. HR-FAB-MS (NBA/PEG): calcd. for C$_{23}$H$_{30}$N$_2$O$_4$F: 417.2190. found: 417.2192. FIG. 9a is the 1H-NMR for Compound 17 and FIG. 9b is the 13C-NMR for Compound 17.

Preparation of 10-Chloromitragynine (18)

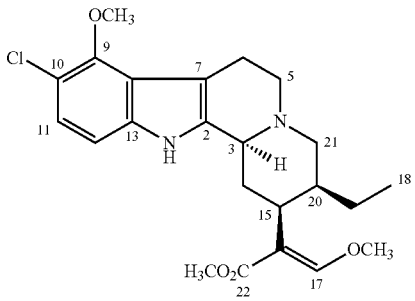

To a stirred solution of 12a (14.7 mg, 0.03 mmol) in dry AcOH (0.5 mL) was added NaCNBH$_3$ (4.0 mg, 0.06 mmol) at room temperature. After 15 min, another portion of NaCNBH$_3$ (4.0 mg, 0.06 mmol) was added to the reaction mixture, and this was stirred for 1 h at room temperature under argon atmosphere. MeOH (40 μL) was added to the reaction mixture, which was then heated under reflux at 90° C. for 18.5 h. The reaction mixture was poured into cold aqueous NH$_4$OH solution, and this was extracted three times with chloroform. The combined extract was washed with brine, dried over MgSO$_4$, and evaporated to give a residue that was purified by silica gel column chromatography (ethyl acetate/n-hexane=50:50) to give 11.7 mg (91%) of 18 as a colorless amorphous powder. Compound 18; UV (MeOH) λ$_{max}$ nm (log ε): 279 (3.64), 271 (3.63), 233 (4.40), 210 (4.16). IR (ATR) ν$_{max}$ cm$^{-1}$: 2939, 1697, 1647, 1457, 1239. $^1$H-NMR (500 MHz, CDCl$_3$) δ ppm: 7.88 (1H, br. s, N$_a$—H), 7.43 (1H, s, H-17), 7.04 (1H, d, J=8.2 Hz, H-11), 6.98 (1H, d, J=8.5 Hz, H-12), 3.93 (3H, s, 9-OCH$_3$), 3.73 (3H, s, 17-OCH$_3$), 3.71 (3H, s, 22-OCH$_3$), 3.15 (1H, d, J=8.8 Hz, H-3), 3.10 (1H, m, H-6), 3.04 (1H, m, H-15), 3.03 (1H, m, H-21), 2.96 (1H, m, H-5), 2.92 (1H, m, H-6), 2.55 (1H, m, H-5), 2.51 (1H, m, H-14), 2.46 (1H, m, H-21), 1.80 (1H, d, J=13.1 Hz, H-14), 1.75 (1H, m, H-19), 1.65 (1H, br. d, J=11.5 Hz, H-20), 1.23 (1H, m, H-19), 0.87 (3H, dd, J=7.3, 7.3 Hz, H$_3$-18). $^{13}$C-NMR (125 MHz, CDCl$_3$) δ ppm: 169.1 (C-22), 160.5 (C-17), 149.1 (C-9), 136.4 (C-13*), 136.2 (C-2*), 122.6 (C-11), 122.4 (C-8$^†$), 117.1 (C-10$^†$), 111.4 (C-16), 107.8 (C-12), 107.2 (C-7), 61.9 (9-OCH$_3$), 61.6 (17-OCH$_3$), 61.2 (C-3), 57.8 (C-21), 53.6 (C-5), 51.4 (22-OCH$_3$), 40.6 (C-20), 39.9 (C-15), 29.8 (C-14), 23.2 (C-6), 19.1 (C-19), 12.8 (C-18). *,$^†$: interchangeable. CD (c=0.15 mM, MeOH, 24° C.), Δε (λ nm): 0 (319), +1.0 (274), 0 (263), −7.1 (242), 0 (234), +1.4 (229), 0 (224), −3.9 (215), 0 (204), +3.0 (200). FAB-MS (NBA) m/z: 435 [M+2+H]$^+$, 433 [M+H]$^+$. HR-FAB-MS (NBA/PEG): calcd. for C$_{23}$H$_{30}$N$_2$O$_4$$^{35}$Cl: 433.1894. found: 433.1856, calcd. for C$_{23}$H$_{30}$N$_2$O$_4$$^{37}$Cl: 435.1875. found: 435.1853

Preparation of 10-Bromomitragynine (19)

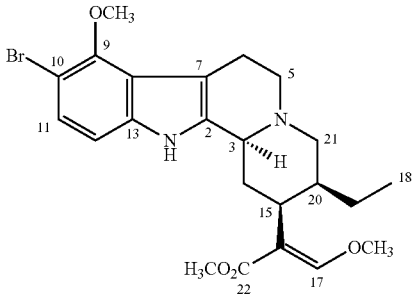

To a stirred solution of 13a (12.1 mg, 0.023 mmol) in dry AcOH (0.4 mL) was added NaCNBH$_3$ (3.0 mg, 0.045 mmol) at room temperature. After 15 min, another portion of NaC- NBH₃ (3.0 mg, 0.045 mmol) was added to the reaction mixture, and this was stirred for 1 h at room temperature under argon atmosphere. MeOH (20 μL) was added to the reaction mixture, which was then heated under reflux at 90° C. for 12 h. The reaction mixture was poured into cold aqueous NH₄OH solution, and this was extracted three times with chloroform. The combined extract was washed with brine, dried over MgSO₄, and evaporated to give a residue that was purified by pre-packed amino-silica gel column chromatography (ethyl acetate/n-hexane=30:70-50:50) to give 10.3 mg (96%) of 19 as a colorless amorphous powder. Compound 19; UV (MeOH) $\lambda_{max}$ nm (log ε): 279 (3.67), 231 (4.47), 210 (4.21). IR (KBr) $v_{max}$ cm$^{-1}$: 2954, 1699, 1636, 1458, 1246. ¹H-NMR (400 MHz, CDCl₃) δ ppm: 7.90 (1H, br. s, N$_a$—H), 7.44 (1H, s, H-17), 7.18 (1H, d, J=8.4 Hz, H-11), 6.95 (1H, d, J=8.4 Hz, H-12), 3.92 (3H, s, 9-OCH₃), 3.74 (3H, s, 17-OCH₃), 3.71 (3H, s, 22-OCH₃), 3.15 (1H, d, J=11.5 Hz, H-3), 3.10 (1H, m, H-6), 3.03 (2H, m, H-15 and H-21), 2.95 (2H, m, H-5 and H-6), 2.56 (1H, m, H-5), 2.51 (1H, m, H-14), 2.46 (1H, dd, J=11.6, 2.7 Hz, H-21), 1.81 (1H, d, J=12.4 Hz, H-14), 1.75 (1H, m, H-19), 1.64 (1H, br. d, J=11.0 Hz, H-20), 1.22 (1H, m, H-19), 0.87 (3H, dd, J=7.3, 7.3 Hz, H₃-18). ¹³C-NMR (100 MHz, CDCl₃) δ ppm: 169.1 (C-22), 160.5 (C-17), 150.1 (C-9), 137.1 (C-13), 136.0 (C-2), 125.2 (C-11), 122.6 (C-8), 111.3 (C-16), 108.4 (C-12), 107.1 (C-7), 106.0 (C-10), 62.1 (9-OCH₃), 61.6 (17-OCH₃), 61.2 (C-3), 57.7 (C-21), 53.6 (C-5), 51.4 (22-OCH₃), 40.6 (C-20), 39.9 (C-15), 29.7 (C-14), 23.2 (C-6), 19.1 (C-19), 12.8 (C-18). CD (c=0.28 mM, MeOH, 24° C.), Δε (λ nm): 0 (324), +0.9 (275), 0 (263), −7.3 (243), 0 (234), +2.0 (230), 0 (224), −3.8 (213), 0 (205), +3.6 (200). FAB-MS (NBA) m/z: 479 [M+2+H]⁺, 477 [M+H]⁺. HR-FAB-MS (NBA/PEG): calcd. for C₂₃N₃₀N₂O₄⁷⁹Br: 477.1389. found: 477.1393, calcd. for C₂₃H₃₀N₂O₄⁸¹Br: 479.1372. found: 479.1377.

Preparation of 10-Nitromitragynine (19) via Indolenine 16

To a solution of 14a (56.8 mg, 0.11 mmol) in dry DCM (1.0 mL) were added 2,6-lutidine (66 μL, 0.57 mmol) and tert-butyldimethylsilyl trifluoromethanesulfonate (66 μL, 0.28 mmol) and the mixture was stirred for 23 h at room temperature under

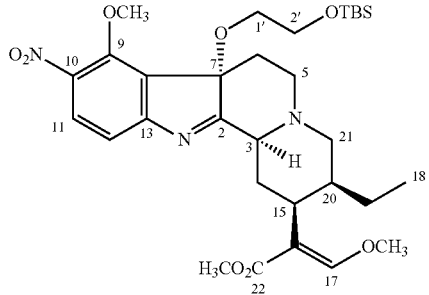

argon atmosphere. The reaction mixture was poured into cold saturated aqueous NaHCO₃ solution, and this was extracted three times with chloroform. The combined extract was washed with brine, dried over MgSO₄, and evaporated to give a residue that was purified by pre-packed silica gel column chromatography (ethyl acetate/n-hexane=25:75) and then amino-silica gel column chromatography (CHCl₃/n-hexane=30:70) to give 60.6 mg (87%) of 16 as an amorphous powder. Compound 16; UV (MeOH) $\lambda_{max}$ nm: 284, 275, 243 (sh), 214, 201. ¹H-NMR (400 MHz, CDCl₃) δ ppm: 7.94 (1H, d, J=8.4 Hz, H-11), 7.45 (1H, s, H-17), 7.41 (1H, d, J=8.4 Hz, H-12), 4.04 (3H, s, 9-OCH₃), 3.83 (3H, s, 17-OCH₃), 3.71 (3H, s, 22-OCH₃), 3.68 (2H, m), 3.05 (4H, m), 2.87 (3H, m), 2.76 (1H, d, J=13.9 Hz), 2.63 (1H, d, J=11.5 Hz), 2.48 (1H, d, J=11.5 Hz), 1.84 (1H, d, J=13.7 Hz), 1.64 (3H, m), 1.25 (1H, m, H-19), 0.89 (9H, s, —OSi(CH₃)₂C(CH₃)₃), 0.83 (3H, dd, J=7.3, 7.3 Hz, H₃-18), 0.07 (3H, s, —OSi(CH₃)₂C(CH₃)₃), 0.05 (3H, s, —OSi(CH₃)₂C(CH₃)₃). ¹³C-NMR (125 MHz, CDCl₃) δ ppm: 188.8 (C-2), 169.1 (C-22), 160.7 (C-17), 159.2 (C-13), 150.9 (C-9), 141.9 (C-10), 130.8 (C-8), 128.3 (C-11), 116.8 (C-12), 111.5 (C-16), 86.6 (C-7), 66.1 (C-1'), 62.6 (9-OCH₃), 62.2 (C-2'), 62.0 (C-3), 61.8 (17-OCH₃), 58.1 (C-21), 51.3 (22-OCH₃), 50.0 (C-5), 40.4 (C-20), 39.0 (C-15), 35.6 (C-6), 25.9 (—OSi(CH₃)₂C(CH₃)₃), 25.8 (C-14), 18.9 (C-19), 18.4 (—OSi(CH₃)₂C(CH₃)₃), 12.8 (C-18), −5.2 (—OSi(CH₃)₂C(CH₃)₃), −5.4 (—OSi(CH₃)₂C(CH₃)₃). FAB-MS (NBA) m/z: 618 [M+H]⁺.

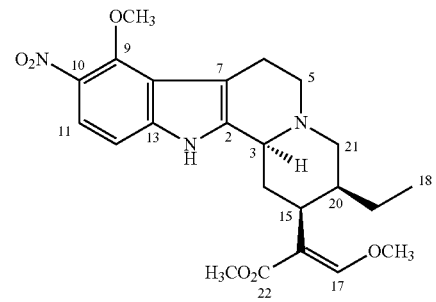

To a stirred solution of 16 (95.9 mg, 0.16 mmol) in dry AcOH (2.0 mL) was added NaCNBH₃ (19.9 mg, 0.30 mmol) at room temperature. After 10 min, another portion of NaCNBH₃ (19.9 mg, 0.30 mmol) was added to the reaction mixture, and this was stirred for 30 min at room temperature under argon atmosphere. MeOH (20 μL) was added to the reaction mixture, which was then heated under reflux at 90° C. for 13 h. The reaction mixture was poured into cold aqueous NH₄OH solution, and this was extracted three times with chloroform. The combined extract was washed with brine, dried over MgSO₄, and evaporated to give a residue that was purified by silica gel column chromatography (ethyl acetate/n-hexane=40:60-100:0) to give 65.0 mg (94%) of 20 as a colorless amorphous powder. Compound 20; UV (MeOH) $\lambda_{max}$ nm (log ε): 327 (3.71), 306 (3.60), 260 (4.23), 239 (4.21), 217 (5.36). IR (KBr) $v_{max}$ cm$^{-1}$: 3387, 2952, 1701, 1620, 1520, 1330, 1245. ¹H-NMR (400 MHz, CDCl₃) δ ppm: 8.07 (1H, br. s, N$_a$—H), 7.77 (1H, d, J=9.0 Hz, H-11), 7.44 (1H, s, H-17), 7.05 (1H, d, J=8.8 Hz, H-12), 4.02 (3H, s, 9-OCH₃), 3.75 (3H, s, 17-OCH₃), 3.71 (3H, s, 22-OCH₃), 3.18 (1H, d, J=13.9 Hz, H-3), 3.16 (1H, m, H-6), 3.05 (2H, m, H-15 and H-21), 2.98 (2H, m, H-5 and H-6), 2.56 (2H, m, H-5 and H-14), 2.48 (1H, d, J=9.2 Hz, H-21), 1.82 (1H, d, J=12.8 Hz, H-14), 1.75 (1H, m, H-19), 1.65 (1H, br. d, J=13.2 Hz, H-20), 1.24 (1H, m, H-19), 0.88 (3H, dd, J=7.3, 7.3 Hz, H₃-18). ¹³C-NMR (125 MHz, CDCl₃) δ ppm: 169.0 (C-22), 160.6 (C-17), 149.9 (C-9), 139.9 (C-13), 137.5 (C-2), 135.4 (C-10), 122.0 (C-8), 119.2 (C-11), 111.2 (C-16), 109.9 (C-7), 106.8 (C-12), 107.1 (C-7), 63.5 (9-OCH₃), 61.6 (17-OCH₃), 61.0 (C-3), 57.7 (C-21), 53.3 (C-5), 51.4 (22-OCH₃), 40.5 (C-20), 39.7 (C-15), 29.7 (C-14), 23.3 (C-6), 19.1 (C-19), 12.8 (C-18). CD (c=0.28 mM, MeOH, 24° C.), Δε (λ nm): 0 (410), −1.4 (357), 0 (325), +5.3 (273), 0 (261), −6.9 (237), +0.1 (226), +2.6 (221), −0.1 (217), −7.8 (206), −5.3 (200). FAB-MS (NBA) m/z: 444 [M+H]⁺. HR-FAB-MS (NBA/PEG): calcd. for C₂₃H₃₀N₃O₆: 444.2135, found: 444.2104.

Preparation of 10-Methoxymitragynine (21)

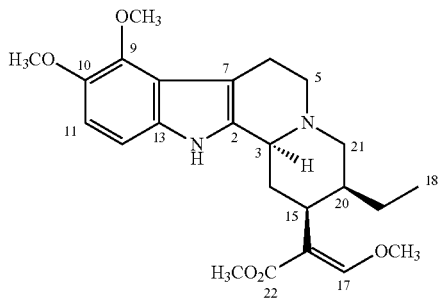

To a stirred solution of 15 (41.2 mg, 0.084 mmol) in dry AcOH (1.0 mL) was added NaCNBH$_3$ (11.2 mg, 0.17 mmol) at room temperature. After 15 min, another portion of NaCNBH$_3$ (11.2 mg, 0.17 mmol) was added to the reaction mixture, and this was stirred for 1 h at room temperature under argon atmosphere. MeOH (40 μL) was added to the reaction mixture, which was then heated under reflux at 90° C. for 5 h. The reaction mixture was poured into cold aqueous NH$_4$OH solution, and this was extracted three times with chloroform. The combined extract was washed with brine, dried over MgSO$_4$, and evaporated to give a residue that was purified by pre-packed amino-silica gel column chromatography (ethyl acetate/n-hexane=30:70) and then by silica gel column chromatography (ethyl acetate/n-hexane=40:60) to give 23.2 mg (64%) of 21 as a colorless amorphous powder. Compound 21; UV (MeOH) λ$_{max}$ nm (log ε): 276 (3.76), 229 (4.40), 208 (4.27). IR (KBr) ν$_{max}$ cm$^{-1}$: 3358, 2936, 1702, 1643, 1502, 1435, 1244. $^1$H-NMR (400 MHz, CDCl$_3$) δ ppm: 7.58 (1H, br. s, N$_a$—H), 7.43 (1H, s, H-17), 6.95 (1H, d, J=8.6 Hz, H-11), 6.81 (1H, d, J=8.8 Hz, H-12), 3.92 (3H, s, 9-OCH$_3$), 3.88 (3H, s, 10-OCH$_3$), 3.73 (3H, s, 17-OCH$_3$), 3.71 (3H, s, 22-OCH$_3$), 3.15 (1H, m, H-3), 3.13 (1H, m, H-6), 3.02 (2H, m, H-15 and H-21), 2.95 (1H, m, H-5 and H-6), 2.55 (1H, m, H-5), 2.50 (1H, m, H-14), 2.45 (1H, m, H-21), 1.79 (1H, d, J=14.6 Hz, H-14), 1.75 (1H, m, H-19), 1.63 (1H, br. d, J=10.6 Hz, H-20), 1.21 (1H, m, H-19), 0.87 (3H, dd, J=7.3, 7.3 Hz, H$_3$-18). $^{13}$C-NMR (100 MHz, CDCl$_3$) δ ppm: 169.2 (C-22), 160.5 (C-17), 145.5 (C-10), 142.6 (C-9), 136.1 (C-2), 133.2 (C-13), 122.3 (C-8), 111.5 (C-16), 110.6 (C-11), 107.1 (C-7), 106.0 (C-12), 61.7 (17-OCH$_3$), 61.5 (9-OCH$_3$), 61.3 (C-3), 58.2 (10-OCH$_3$), 57.8 (C-21), 53.7 (C-5), 51.3 (22-OCH$_3$), 40.6 (C-20), 39.9 (C-15), 29.8 (C-14), 23.4 (C-6), 19.1 (C-19), 12.8 (C-18). CD (c=0.31 mM, MeOH, 24° C.), Δε (λ nm): 0 (323), +0.1 (318), 0 (315), −0.1 (307), 0 (304), +2.2 (274), 0 (260), −6.3 (243), −2.6 (229), −5.9 (218), −5.8 (216), −6.3 (212), 0 (204), +0.8 (200). FAB-MS (NBA) m/z: 429 [M+H]$^+$. HR-FAB-MS (NBA/PEG): calcd. for C$_{24}$H$_{33}$N$_2$O$_5$: 429.2389, found: 429.2376.

Preparation of 7-Hydroxy-10-fluoromitragynine (22)

A solution of PIFA (56.0 mg, 0.13 mmol) in MeCN (0.5 mL) was added dropwise to a

Figure 10A:
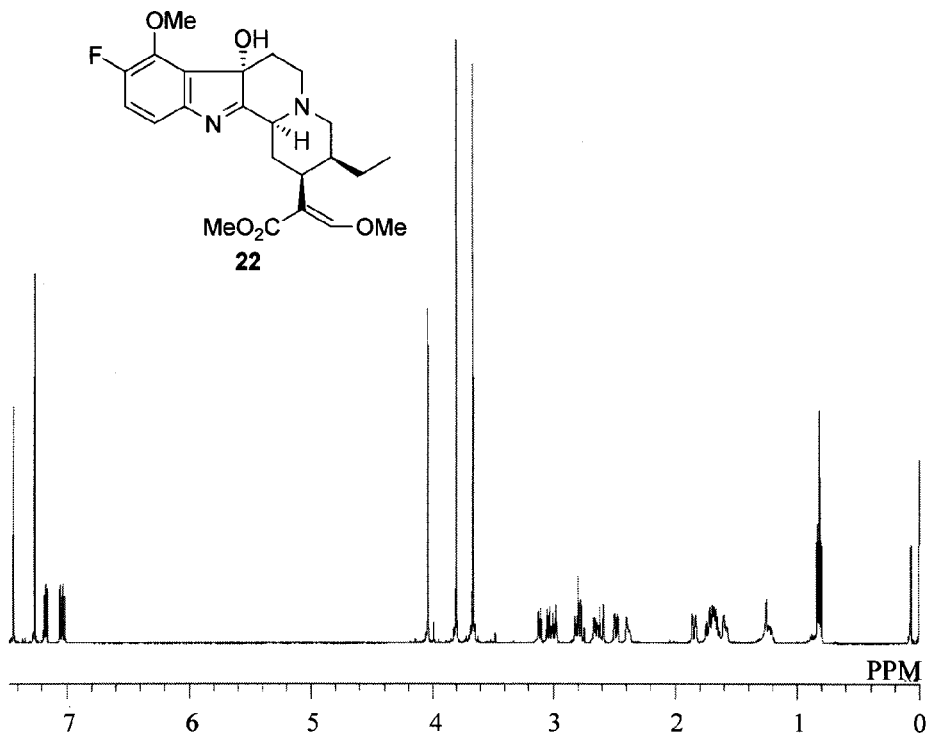
FIG. 10a is the 1H-NMR for Compound 22 and FIG. 10b is the 13C-NMR for Compound 22.
Figure 10B:
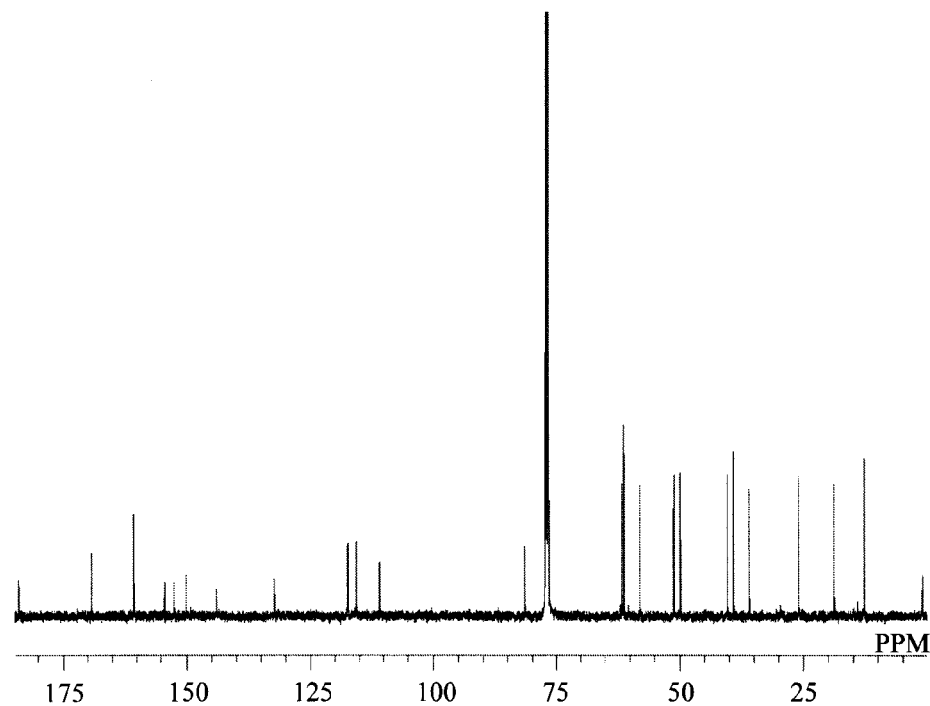

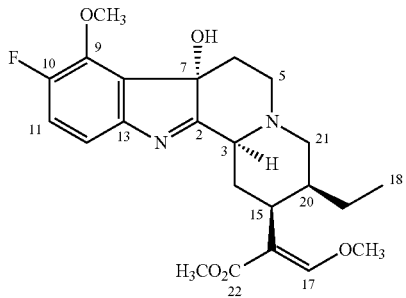

stirred solution of 17 (51.8 mg, 0.12 mmol) in MeCN (1.7 mL) and H$_2$O (0.6 mL) at 0° C. and the mixture was stirred for 2 h at the same temperature under argon atmosphere. The reaction mixture was poured into cold saturated aqueous NaHCO$_3$ solution, and this was extracted three times with chloroform. The combined extract was washed with brine, dried over MgSO$_4$, and concentrated to give a residue that was purified by pre-packed amino-silica gel column chromatography (ethyl acetate/n-hexane=30:70-50:50) to give 30.2 mg (56%) of 22 as a colorless amorphous powder. Compound 22; UV (MeOH) λ$_{max}$ nm (log ε): 295 (3.37), 287 (3.37), 245 (sh, 4.03), 221 (4.22), 207 (4.13), 201 (4.15). IR (KBr) ν$_{max}$ cm$^{-1}$: 3395, 2952, 1702, 1645, 1488, 1250. $^1$H-NMR (500 MHz, CDCl$_3$) δ ppm: 7.43 (1H, s, H-17), 7.18 (1H, dd, J=8.4, 3.6 Hz, H-12), 7.04 (1H, dd, J=12.5, 8.2 Hz, H-11), 4.04 (3H, d, J=2.7 Hz, 9-OCH$_3$), 3.80 (3H, s, 17-OCH$_3$), 3.67 (3H, s, 22-OCH$_3$), 3.12 (1H, dd, J=11.0, 2.4 Hz, H-3), 3.04 (1H, dd, J11.4, 3.1 Hz, H-21), 3.00 (1H, ddd, J=14.0, 3.6, 3.6 Hz, H-15), 2.80 (2H, m, H-5 and H-14), 2.65 (1H, m, H-5), 2.60 (1H, m, H-6), 2.49 (1H, dd, J=11.6, 2.7 Hz, H-21), 1.85 (1H, d, J=13.7 Hz, H-14), 1.70 (2H, m, H-6 and H-19), 1.59 (1H, br.d, J=11.0 Hz, H-20), 1.24 (1H, m, H-19), 0.82 (3H, dd, J=7.3, 7.3 Hz, H$_3$-18). $^{13}$C-NMR (125 MHz, CDCl$_3$) δ ppm: 183.9 (C-2), 169.3 (C-22), 160.8 (C-17), 153.6 (d, J=247.0 Hz, C-10), 150.2 (C-13), 144.0 (d, J=12.8 Hz, C-9), 132.3 (d, J=3.7 Hz, C-8), 117.5 (d, J21.5 Hz, C-11), 115.8 (d, J=7.3 Hz, C-12), 111.1 (C-16), 81.4 (C-7), 61.8 (17-OCH$_3$), 61.5 (d, J=4.6 Hz, 9-OCH$_3$), 61.5 (C-3), 58.1 (C-21), 51.3 (22-OCH$_3$), 49.9 (C-5), 40.4 (C-20), 39.2 (C-15), 35.9 (C-6), 26.0 (C-14), 18.9 (C-19), 12.8 (C-18). CD (c=0.27 mM, MeOH, 24° C.), Δε (λ nm): 0 (341), +3.6 (299), +1.4 (280), +9.0 (254), −0.1 (239), −11.8 (225), 0 (210), +9.0 (200). FAB-MS (NBA) m/z: 433 [M+H]$^+$. HR-FAB-MS (NBA/PEG): calcd. for C$_{23}$H$_{30}$N$_2$O$_5$F: 433.2139. found: 433.2140. FIG. 10$a$ is the 1H-NMR for Compound 22 and FIG. 10$b$ is the 13C-NMR for Compound 22.

Preparation of 7-Hydroxy-10-chloromitragynine (23)

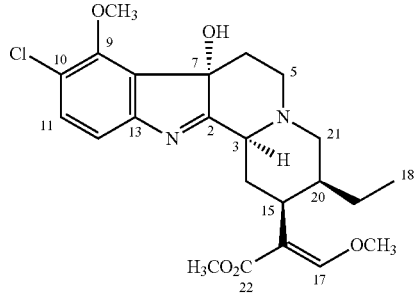

A solution of PIFA (26.1 mg, 0.059 mmol) in MeCN (0.2 mL) was added dropwise to a stirred solution of 18 (23.1 mg, 0.053 mmol) in MeCN (0.9 mL) and H$_2$O (0.3 mL) at 0° C. and the mixture was stirred at the same temperature under argon atmosphere. After 1 h, another portion of PIFA (2.3 mg, 0.005 mmol) was added to the reaction mixture, and this was further stirred for 3.5 h at 0° C. The reaction mixture was poured into cold saturated aqueous NaHCO$_3$ solution, and this was extracted three times with chloroform. The combined extract was washed with brine, dried over MgSO$_4$, and evaporated to give a residue that was purified by silica gel column chromatography (ethyl acetate/n-hexane=40:60) to give 12.8 mg (54%) of 23 as a colorless amorphous powder. Compound 23; UV (MeOH) λ$_{max}$ nm (log ε): 303 (3.49), 244 (sh, 4.09), 224 (4.25), 209 (4.20), 202 (4.22). IR (KBr) ν$_{max}$ cm$^{-1}$: 3410, 2930, 1682, 1642, 1592, 1464, 1247. $^1$H-NMR (500 MHz, CDCl$_3$) δ ppm: 7.44 (1H, s, H-17), 7.35 (1H, d, J=7.9 Hz, H-11), 7.26 (1H, d, J=7.9 Hz, H-12), 3.99 (3H, s, 9-OCH$_3$), 3.81 (3H, s, 17-OCH$_3$), 3.66 (3H, s, 22-OCH$_3$), 3.13 (1H, dd, J=11.0, 2.4 Hz, H-3), 3.05 (1H, dd, J=11.3, 2.1

Hz, H-21), 3.00 (1H, ddd, J=14.0, 3.7, 3.7 Hz, H-15), 2.79 (2H, m, H-5 and H-14), 2.67 (1H, m, H-5), 2.63 (1H, m, H-6), 2.49 (1H, dd, J=11.1, 2.3 Hz, H-21), 1.85 (1H, d, J=13.7 Hz, H-14), 1.69 (2H, m, H-6 and H-19), 1.59 (1H, br. d, J=11.0 Hz, H-20), 1.24 (1H, m, H-19), 0.82 (3H, dd, J=7.3, 7.3 Hz, $H_3$-18). $^{13}$C-NMR (125 MHz, $CDCl_3$) δ ppm: 184.4 (C-2), 169.3 (C-22), 160.8 (C-17), 153.9 (C-9), 152.5 (C-13), 133.7 (C-8), 131.5 (C-11), 125.5 (C-10), 117.8 (C-12), 111.1 (C-16), 81.4 (C-7), 62.1 (9-$OCH_3$), 61.8 (17-$OCH_3$), 61.5 (C-3), 58.1 (C-21), 51.3 (22-$OCH_3$), 50.0 (C-5), 40.4 (C-20), 39.2 (C-15), 36.0 (C-6), 26.0 (C-14), 18.9 (C-19), 12.8 (C-18). CD (c=0.32 mM, MeOH, 24° C.), Δε (λ nm): 0 (346), +3.8 (303), +1.4 (282), +9.7 (257), −0.1 (241), −13.2 (227), −0.1 (212), +8.5 (204), +5.9 (200). FAB-MS (NBA) m/z: 451 $[M+2H]^+$, 449 $[M+H]^+$. HR-FAB-MS (NBA/PEG): calcd. for $C_{23}H_{30}N_2O_5{}^{35}Cl$: 449.1843. found: 449.1853, calcd. for $C_{23}H_{30}N_2O_5{}^{37}Cl$: 451.1825. found: 451.1775.

Preparation of 7-Hydroxy-10-bromomitragynine (24)

A solution of PIFA (12.9 mg, 0.029 mmol) in MeCN (0.2 mL) was added dropwise to a stirred solution of 19 (13.9 mg, 0.029 mmol) in MeCN (0.5 mL) and $H_2O$ (0.2 mL) at 0° C. and the mixture was stirred at the same temperature under argon atmosphere. After 1.5 h, another portion of PIFA (1.3 mg, 0.003 mmol) was added to the reaction mixture, and this was further stirred for 3.5 h at 0° C. The reaction mixture was poured into cold saturated aqueous $NaHCO_3$ solution, and this was extracted three times with chloroform. The combined extract was washed with brine, dried over $MgSO_4$, and evaporated to

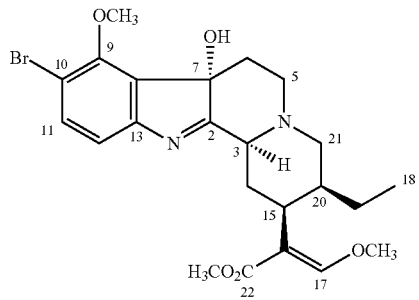

give a residue that was purified by pre-packed silica gel column chromatography (ethyl acetate/n-hexane=40:60) to give 4.8 mg (33%) of 24 as a colorless amorphous powder, together with 0.6 mg (6%) of recovered starting material 19. Compound 24; UV (MeOH) $λ_{max}$ nm (log ε): 306 (3.54), 248 (sh, 4.09), 221 (4.26), 208 (4.21), 201 (4.25). IR (KBr) $ν_{max}$ $cm^{-1}$: 3393, 2935, 1670, 1646, 1459, 1249. $^1$H-NMR (400 MHz, $CDCl_3$) δ ppm: 7.44 (1H, s, H-17), 7.53 (1H, d, J=8.2 Hz, H-11), 7.21 (1H, d, J=8.2 Hz, H-12), 3.99 (3H, s, 9-$OCH_3$), 3.81 (3H, s, 17-$OCH_3$), 3.65 (3H, s, 22-$OCH_3$), 3.12 (1H, dd, J=11.2, 2.4 Hz, H-3), 3.05 (1H, dd, J=11.5, 2.0 Hz, H-21), 2.99 (1H, ddd, J=13.9, 3.5, 3.5 Hz, H-15), 2.79 (2H, m, H-5 and H-14), 2.66 (1H, m, H-5), 2.63 (1H, d, J=15.2 Hz, H-6), 2.49 (1H, dd, J=11.4, 3.0 Hz, H-21), 1.87 (1H, d, J=13.7 Hz, H-14), 1.69 (2H, m, H-6 and H-19), 1.59 (1H, br. d, J=11.5 Hz, H-20), 1.24 (1H, m, H-19), 0.82 (3H, dd, J=7.3, 7.3 Hz, $H_3$-18). $^{13}$C-NMR (125 MHz, $CDCl_3$) δ ppm: 184.3 (C-2), 169.3 (C-22), 160.8 (C-17), 154.8 (C-9), 153.6 (C-13), 133.8 (C-8), 134.6 (C-11), 118.4 (C-12), 114.8 (C-10), 111.1 (C-16), 81.5 (C-7), 62.3 (9-$OCH_3$), 61.8 (17-$OCH_3$), 61.5 (C-3), 58.1 (C-21), 51.3 (22-$OCH_3$), 50.0 (C-5), 40.4 (C-20), 39.2 (C-15), 36.0 (C-6), 26.0 (C-14), 18.9 (C-19), 12.8 (C-18). CD (c=0.21 mM, MeOH, 24° C.), Δε (λ nm): 0 (346), +4.2 (304), +1.4 (282), +10.9 (258), 0 (242), −14.0 (228), 0 (214), +9.1 (205), +8.5 (200). FAB-MS (NBA) m/z: 495 $[M+2H]^+$, 493 $[M+H]^+$. HR-FAB-MS (NBA/PEG): calcd. for $C_{23}H_{30}N_2O_5{}^{79}Br$: 493.1338. found: 493.1317, calcd. for $C_{23}H_{30}N_2O_5{}^{81}Br$: 495.1321. found: 495.1375.

Preparation of 7-Hydroxy-10-methoxymitragynine (25)

A solution of PIFA (22.7 mg, 0.051 mmol) in MeCN (1.0 mL) was added dropwise to a stirred solution of 21 (21.5 mg, 0.050 mmol) in MeCN (3.0 mL) and $H_2O$ (1.0 mL) at 0° C. and the mixture was stirred for 1 h at the same temperature under argon atmosphere. The reaction mixture was poured into cold saturated aqueous $NaHCO_3$ solution, and this was extracted three times with chloroform. The combined extract was washed with brine, dried over $MgSO_4$, and concentrated to give a residue that was purified by amino-silica gel column chromatography (ethyl acetate/n-hexane=30:70) to give 4.4 mg (20%) of 25 as a colorless amorphous powder. Compound 25; UV (MeOH)

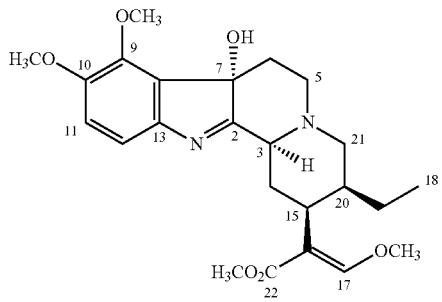

$λ_{max}$ nm (log ε): 311 (3.48), 297 (3.43), 236 (4.08), 215 (4.04), 202 (4.12). IR (KBr) $ν_{max}$ $cm^{-1}$: 3410, 2952, 1702, 1644, 1488, 1433, 1259. $^1$H-NMR (400 MHz, $CDCl_3$) δ ppm: 7.44 (1H, s, H-17), 7.24 (1H, d, J=8.2 Hz, H-12*), 6.84 (1H, d, J=8.4 Hz, H-11*), 3.95 (3H, s, 9-$OCH_3$), 3.86 (3H, s, 10-$OCH_3$), 3.80 (3H, s, 17-$OCH_3$), 3.69 (3H, s, 22-$OCH_3$), 3.11 (1H, dd, J=11.2, 2.6 Hz, H-3), 3.02 (2H, m, H-15 and H-21), 2.79 (2H, m, H-5 and H-14), 2.62 (2H, m, H-5 and H-6), 2.47 (1H, dd, J=11.5, 2.7 Hz, H-21), 2.22 (1H, br. s, 7-OH), 1.86 (1H, d, J=13.7 Hz, H-14), 1.75 (1H, ddd, J=13.5, 13.5, 4.6 Hz, H-6), 1.71 (1H, m, H-19), 1.59 (1H, br. d, J=11.4 Hz, H-20), 1.25 (1H, m, H-19), 0.82 (3H, dd, J=7.3, 7.3 Hz, $H_3$-18), *: interchangeable. $^{13}$C-NMR (125 MHz, $CDCl_3$) δ ppm: 182.0 (C-2), 169.3 (C-22), 160.7 (C-17), 151.5 (C-13), 147.9 (C-9), 145.9 (C-10), 132.6 (C-8), 116.3 (C-11), 112.7 (C-12), 111.3 (C-16), 81.2 (C-7), 61.8 (17-$OCH_3$), 61.5 (C-3 and 9-$OCH_3$), 58.2 (C-21), 56.2 (10-$OCH_3$), 51.3 (22-$OCH_3$), 50.1 (C-5), 40.5 (C-20), 39.3 (C-15), 36.3 (C-6), 26.1 (C-14), 19.0 (C-19), 12.8 (C-18). CD (c=0.25 mM, MeOH, 24° C.), Δε (λ nm): 0 (334), +2.3 (316), +2.4 (306), 0 (289), −0.3 (285), 0 (281), +6.4 (264), +7.6 (256), 0 (244), −9.6 (233), −9.3 (228), 0 (211), +4.0 (200). FAB-MS (NBA) m/z: 445 $[M+H]^+$. HR-FAB-MS (NBA/PEG): calcd. for $C_{24}H_{33}N_2O_6$: 445.2339, found: 445.2314.

Magnus Assay Using Guinea Pig Ileum Preparations

Male albino guinea pigs (Japan SLC) weighing 320-550 g were used. Animals were housed in a temperature-controlled room at 24° C. with lights on from 07:00-19:00 and had free access to food and water. The guinea-pig ileum was dissected and placed in Krebs-Henseleit solution (in mM: NaCl, 112.08; KCl, 5.90; $CaCl_2$, 1.97; $MgCl_2$, 1.18; $NaH_2PO_4$, 1.22; $NaHCO_3$, 25.00, and glucose, 11.49). The ileum was set up under 1 g of tension in 5 mL of an organ bath containing the nutrient solution. The bath was maintained at 37° C. and continuously bubbled with a gas mixture of 95% $O_2$ and 5% $CO_2$. At the start of each experiment, the maximum response to acetylcholine (3 μM) was obtained for each tissue to check its suitability. Tissues were stimulated through platinum needle-ring (a ring was placed 20 mm above the base of a needle 5 mm in length) electrodes using square wave pulses of supramaximal voltage. The ileum was transmurally stimulated with monophasic pulses (0.2 Hz) at 0.3 ms duration by a stimulator (SEN-7203, Nihon Kohden, Tokyo, Japan). Contractions were isotonically recorded with a displacement transducer (NEC, San-ei Instruments Ltd., Type 45347), a DC strain amplifier (San-ei 6M92), and a DC recorder (Hitachi, Mod 056, Tokyo, Japan). All concentration-response curves were constructed in a cumulative manner. The height of the twitch response to transmural stimulation was measured before and after drug challenge. The twitch response remaining after each sample addition was determined by dividing the height after its addition by the height before addition multiplied by 100. To obtain the percentage inhibition, this value was subtracted from 100. Agonist activity was expressed as $pD_2$ value, which is the negative logarithm of the molar concentration required to produce 50% of the maximum response to the drug ($EC_{50}$). To investigate the involvement of opioid receptors in the inhibitory effect of the samples, the antagonistic effect of the opioid receptor antagonist naloxone was examined. The inhibitory effects of samples on electrically stimulated contraction were regarded as opioid activities when the antagonistic effect of naloxone was observed.

What is claimed is:

1. A compound having the formula:

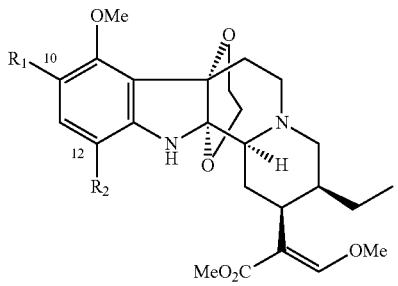

wherein $R_1$ is a halogen atom, hydrogen atom, or a nitro group or alkoxy group and $R_2$ is a hydrogen atom or halogen atom or nitro group.

2. A compound having the formula:

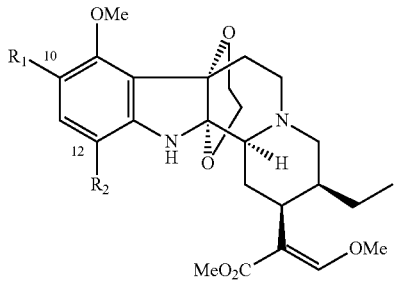

wherein $R_1$=F, $R_2$=H; $R_1$=Cl, $R_2$=H; $R_1$=H, $R_2$=Cl; $R_1$=Br, $R_2$=H; $R_1$=H, $R_2$=Br; $R_1$=NO_2$, $R_2$=H; $R_1$=H, $R_2$=NO_2$; or $R_1$=OMe, $R_2$=H.

3. A pharmaceutical composition comprising a therapeutic amount of a compound of claim 1 or a pharmaceutically acceptable salt thereof.

4. The pharmaceutical composition of claim 3 in a pharmaceutically deliverable form selected from the group consisting of solutions, suspensions, emulsions, tablets, pills, pellets, granules, lozenges, capsules, capsules containing liquids, powders, sustained-release formulations, syrups, elixirs, creams, gels, suppositories, emulsions, aerosols, and sprays.

5. A pharmaceutical composition containing 0.1% to 100% of said compound of claim 1 or a pharmaceutically acceptable salt thereof.

6. A method for eliciting a therapeutic effect in a patient in need thereof, comprising the step of administering to said patient an effective dose of the 2,3-ethylene glycol bridged indoline adduct compound of claim 1 or a pharmaceutically acceptable salt thereof, wherein said therapeutic effect is an analgesic effect.

7. The method of claim 6 wherein said step of administering is performed by a delivery route selected from the group consisting of oral, transdermal, inhalation, injection, infusion, and suppository.

8. The method of claim 6 wherein said patient is an animal.

9. The method of claim 6 wherein said patient is a mammal.

10. The method of claim 6 wherein said patient is a human.

11. The method of claim 6 wherein patient is a human and the therapeutic effect is pain treatment, where an effective total daily dosage of said compound ranges from about 0.1 mg to about 1,000 mg active compound/kg body weight of said patient.

12. A method for making the 2,3-ethylene glycol bridged indoline adduct compound of claim 1, comprising the steps of:
reacting a Corynanthe-type indole alkaloid with hypervalent iodine in the presence of ethylene glycol effective to provide a 2,3-ethylene glycol bridged indoline adduct, effective to mask a 2,3-n bond of an indole nucleus of said adduct.

13. The method of claim 12 further comprising introducing a halogen atom at a C10 position of the adduct via electrophilic aromatic substitution, providing a C10-halogenated adduct derivative.

* * * * *